United States Patent
Albrecht et al.

(10) Patent No.: US 10,150,767 B2
(45) Date of Patent: *Dec. 11, 2018

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); Steven F. Bellon, Cambridge, MA (US); Daniel J. Burdick, South San Francisco, CA (US); Alexandre Cote, Cambridge, MA (US); Terry Crawford, South San Francisco, CA (US); Les A. Dakin, Cambridge, MA (US); Vickie Hsiao-Wei Tsui, South San Francisco, CA (US); Michael Charles Hewitt, Cambridge, MA (US); Yves LeBlanc, Cambridge, MA (US); Steven R. Magnuson, South San Francisco, CA (US); Christopher G. Nasveschuk, Cambridge, MA (US); Anthony F. Romero, South San Francisco, CA (US); Yong Tang, Cambridge, MA (US); Alexander M. Taylor, Cambridge, MA (US); Shumei Wang, South San Francisco, CA (US)

(73) Assignees: Genentech, Inc., South San Francisco, CA (US); Constellation Pharmaceuticals Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/592,017

(22) Filed: May 10, 2017

(65) Prior Publication Data

US 2017/0342067 A1 Nov. 30, 2017

Related U.S. Application Data

(63) Continuation of application No. PCT/US2015/060007, filed on Nov. 10, 2015.

(60) Provisional application No. 62/077,707, filed on Nov. 10, 2014.

(51) Int. Cl.

| C07D 471/04 | (2006.01) |
| A61K 31/437 | (2006.01) |
| C07D 519/00 | (2006.01) |
| A61K 31/4985 | (2006.01) |
| A61K 31/496 | (2006.01) |
| A61K 31/4545 | (2006.01) |
| A61K 45/06 | (2006.01) |

(52) U.S. Cl.
CPC .......... *C07D 471/04* (2013.01); *A61K 31/437* (2013.01); *A61K 31/4545* (2013.01); *A61K 31/496* (2013.01); *A61K 31/4985* (2013.01); *A61K 45/06* (2013.01); *C07D 519/00* (2013.01)

(58) Field of Classification Search
CPC ............................ C07D 471/04; A61K 31/437
See application file for complete search history.

(56) References Cited

U.S. PATENT DOCUMENTS

| 9,359,379 B2 | 6/2016 | Seiwert et al. |
| 9,675,593 B2 | 6/2017 | Ramphal et al. |
| 9,695,200 B2 | 7/2017 | Jacobsen et al. |
| 9,763,922 B2 * | 9/2017 | Adler ..................... A61K 45/06 |
| 2014/0094456 A1 | 4/2014 | Buckman et al. |
| 2014/0107110 A1 | 4/2014 | Buckman et al. |

(Continued)

FOREIGN PATENT DOCUMENTS

| EP | 1953147 A1 | 8/2008 |
| WO | 2007058392 A1 | 5/2007 |

(Continued)

OTHER PUBLICATIONS

Brunton, et al., "Chemotherapy of Neoplastic Diseases", Goodman & Gilman's: The Pharmacological Basis of Therapeutics 11th ed., 853-908 (2008).

(Continued)

*Primary Examiner* — Golam M Shameem
(74) *Attorney, Agent, or Firm* — Viksnins Harris Padys Malen LLP

(57) ABSTRACT

The present invention relates to compounds of formula (I):

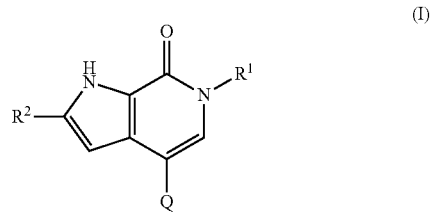

and to salts thereof, wherein $R^1$, $R^2$, and Q have any of the values defined in the specification, and compositions and uses thereof. The compounds are useful as inhibitors of bromodomains. Also included are pharmaceutical compositions comprising a compound of formula (I) or a pharmaceutically acceptable salt thereof, and methods of using such compounds and salts in the treatment of various bromodomain-mediated disorders.

14 Claims, No Drawings

(56) References Cited

U.S. PATENT DOCUMENTS

| | | |
|---|---|---|
| 2014/0162971 A1 | 6/2014 | Wang et al. |
| 2014/0256710 A1 | 9/2014 | Liu et al. |
| 2015/0266899 A1 | 9/2015 | Buckman et al. |
| 2016/0213653 A1 | 7/2016 | Jacobsen et al. |
| 2016/0263090 A1 | 9/2016 | Buckman et al. |
| 2017/0121345 A1 | 5/2017 | Ramphal et al. |
| 2017/0260211 A1 | 9/2017 | Jacobsen et al. |
| 2017/0340604 A1 | 11/2017 | Albrecht et al. |
| 2017/0340605 A1 | 11/2017 | Albrecht et al. |
| 2018/0009805 A1 | 1/2018 | Adler et al. |

FOREIGN PATENT DOCUMENTS

| | | |
|---|---|---|
| WO | 2013097052 A1 | 7/2013 |
| WO | 2013097601 A1 | 7/2013 |
| WO | 2014055548 A1 | 4/2014 |
| WO | 2014125408 A2 | 8/2014 |
| WO | 2014139324 A1 | 9/2014 |
| WO | 2014194667 A1 | 12/2014 |
| WO | 2014201161 A1 | 12/2014 |
| WO | 2014206150 A1 | 12/2014 |
| WO | 2014206345 A1 | 12/2014 |
| WO | 2015081203 A1 | 6/2015 |
| WO | 2015081246 A1 | 6/2015 |
| WO | 2015081280 A1 | 6/2015 |
| WO | 2015153683 A1 | 10/2015 |
| WO | 2015164480 A1 | 10/2015 |

OTHER PUBLICATIONS

CAS Abstract, of US 2014/094456, accession No. 2014:531372, 5 pages (2014).
CAS Abstract, of WO 2014/125408, accession No. 2014:1387149, 3 pages (2014).
U.S. Appl. No. 15/592,012, 2017/0340604.
U.S. Appl. No. 15/592,013, 2017/0340605.
U.S. Appl. No. 15/658,213, 2018/0009805.
Ember, et al., "Acetyl-lysine Binding Site of Bromodomain-Containing Protein 4 (BRD4) Interacts with Diverse Kinase Inhibitors", ACS Chem Biol 9, 1160-1171 (2014).
Filippakopoulos, et al., "Selective inhibition of BET bromodomains", Nature vol. 468 (7327), 1067-1073 (2010).
Filippakopoulos, et al., "Targeting bromodomains: epigenetic readers of lysine acetylation", Nature Reviews 13, 337-356 (2014).
Marelli, et al., "Tumor targeting via integrin ligands", Frontiers in Oncology 3(222), 12 pages (2013).
MedicineNet, "Definition of Cancer", MedicineNet.com, 1 page (Sep. 18, 2004).
National Cancer Institute, "Prostate Cancer Preventions (PDQ®)", http://www.cancer.gov/>, 2 pages (2010).
Shi, et al., "The Mechanisms behind the Therapeutic Activity of BET Bromodomain Inhibition", Molecular Cell Review 54, 728-736 (2014).
Wang, et al., "Mathematical modeling in cancer drug discovery", Drug Discovery Today 19(2), 145-150 (2014).
Gallenkamp, et al., "Bromodomains and their pharmacological inhibitors", ChemMedChem 9(3), 438-464 (2014).
Garnier, et al., "BET bromodomain inhibitors: a patent review", Expert Opin Ther Patents 24(2), 185-199 (2014).
Jeanmougin, "The bromodomain revisited", Trends Biochem Sci 22(5), 151-153 (1997).
Kloet, et al., "Phosphorylation-Dependent Regulation of Cydin D1 and Cyclin A Gene Transcription by TFIID Subunits TAF1 and TAF7", Mol Cell Biol 32(16), 3358-3369 (2012).
Muller, et al., "Bromodomains as therapeutic targets", Expert Rev Mol Med 13 (29), 1-21 (2011).
Papai, "New insights into the function of transcription factor TFIID from recent structural studies", Current Opinion in Genetics & Development 21(2), 219-224 (2011).
Patent Cooperation Treaty, International Searching Authority, Search Report and Written Opinion for PCT/US2015/060007, 13 pages, dated Dec. 21, 2015.
Prinjha, et al., "Place your BETs: the therapeutic potential of bromodomains", Trends Pharm Sci 33(3), 146-153 (2012).
Struhl, "Histone acetylation and transcriptional regulatory mechanisms", Genes Dev 12 (5), 599-606 (1989).
Tamkun, et al., "brahma: a regulator of *Drosophila* homeotic genes structurally related to the yeast transcriptional activator SNF2/SWI2", Cell 68, 561-572 (1992).

* cited by examiner

THERAPEUTIC COMPOUNDS AND USES THEREOF

CROSS-REFERENCE TO RELATED APPLICATION(S)

This patent application is a continuation of International Application No. PCT/US2015/060007, filed Nov. 10, 2015, which claims the benefit of priority of U.S. application Ser. No. 62/077,707, filed Nov. 10, 2014, which applications are herein incorporated by reference.

TECHNICAL FIELD OF THE INVENTION

The present invention relates to compounds useful as inhibitors of bromodomains.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.*, 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., *Trends Biochem. Sci.*, 1997, 22, 5, 151-153; and Tamkun J. W., et al., *Cell*, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.*, 33(3):146-153 (2012) and Muller et al., *Expert Rev.*, 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Moreover, recent findings have demonstrated that small molecule inhibition of the bromodomains of BRD4 may have clinical utility in diverse human diseases, ranging from auto-immunity to cardiac hypertrophy. This is possible because the underlying mechanism resides in transcriptional regulation. Hence, the selective inhibition of bromodomains across the family creates varied opportunities as novel therapeutic agents in human dysfunction.

There is a need for treatments for cancer, immunological disorders, and other bromodomain related diseases.

SUMMARY OF THE INVENTION

One aspect includes a compound of formula (I):

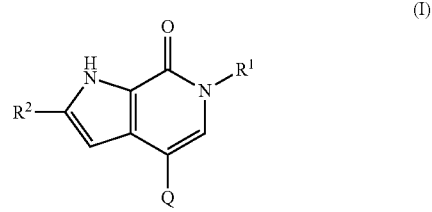

or a salt thereof, wherein:
$R^1$ is H, methyl, or ethyl;
$R^2$ is H, $C_{1-12}$alkyl, $C_{2-12}$alkenyl, $C_{2-12}$alkynyl, carbocyclyl, or heterocyclyl, wherein each $C_{1-12}$alkyl, $C_{2-12}$alkenyl, $C_{2-12}$alkynyl, carbocyclyl, or heterocyclyl of $R^2$ is optionally substituted with one or more groups $R^b$; and
Q is a 5-membered heteroaryl that is optionally substituted with one or more groups $R^c$, or Q is:

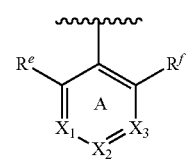

wherein ring A is optionally substituted with one or more groups $R^c$, or ring A is optionally fused with a carbocyclyl or a heterocyclyl to form a polycyclyl that is optionally substituted with one or more groups $R^g$;
$X_1$, $X_2$, and $X_3$ are each independently selected from $CR^c$ and N, provided that at least one of $X_1$, $X_2$, and $X_3$ is not N; and when A is optionally fused with a carbocyclyl or a heterocyclyl to form a polycyclyl, each of $X_1$, $X_2$, and $X_3$ can be C and can be a site of fusion;
each $R^b$ is independently selected from oxo, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —O—C(O)—O—R$^w$, —C(O)—R$^w$, —C(O)—O—R$^w$, —S(O)—R$^w$, —S(O)$_2$—R$^w$, —O—C(O)—N(R$^w$)$_2$, —N(R$^w$)—C(O)—OR$^w$, —N(R$^w$)—C(O)—N(R$^w$)$_2$, —N(R$^w$)—C(O)—R$^w$, —N(R$^w$)—S(O)—R$^w$, —N(R$^w$)—S(O)$_2$—R$^w$, —N(R$^w$)—S(O)—N(R$^w$)$_2$, and —N(R$^w$)—S(O)$_2$—N(R$^w$)$_2$, wherein any C$_{1-6}$alkyl, C$_{2-6}$alkenyl, C$_{2-6}$alkynyl, C$_{1-6}$haloalkyl, carbocyclyl, or heterocyclyl is optionally substituted with one or more groups independently selected from oxo, halo, —NO$_2$, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —C(O)—R$^w$, —C(O)—O—R$^w$, —S(O)—R$^w$, —S(O)$_2$—R$^w$, —C(O)—N(R$^w$)$_2$, —N(R$^w$)—C(O)—R$^w$, —N(R$^w$)—S(O)—R$^w$, —N(R$^w$)—S(O)$_2$—R$^w$ and C$_{1-6}$alkyl that is optionally substituted with one or more groups independently selected from oxo and halo;

each R$^c$ is independently selected from hydrogen, C$_{1-6}$alkyl, C$_{2-6}$alkenyl, C$_{2-6}$alkynyl, C$_{1-6}$haloalkyl, carbocyclyl, heterocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any C$_{1-6}$alkyl, C$_{2-6}$alkenyl, C$_{2-6}$alkynyl, C$_{1-6}$haloalkyl, carbocyclyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$, 6-membered monocyclic heterocyclyl and C$_{1-6}$alkyl that is optionally substituted with one or more groups independently selected from oxo and halo, wherein the 6-membered monocyclic heterocyclyl is optionally substituted with one or more C$_{1-6}$alkyl;

R$^e$ is hydrogen, —F, —Cl, —Br, —I, —CN, —O—R$^x$, C$_{1-6}$alkyl, C$_{2-6}$alkenyl, or C$_{2-6}$alkynyl, wherein each C$_{1-6}$alkyl, C$_{2-6}$alkenyl, or C$_{2-6}$alkynyl is optionally substituted with one or more groups independently selected from oxo, —F, —Cl, —Br, —I, —NO$_2$, —N(R$^x$)$_2$, —CN, —C(O)—N(R$^x$)$_2$, —S(O)—N(R$^x$)$_2$, —S(O)$_2$—N(R$^x$)$_2$, —O—R$^x$, —S—R$^x$, —O—C(O)—R$^x$, —O—C(O)—O—R$^x$, —C(O)—R$^x$, —C(O)—O—R$^x$, —S(O)—R$^x$, —S(O)$_2$—R$^x$, —O—C(O)—N(R$^x$)$_2$, —N(R$^x$)—C(O)—OR$^x$, —N(R$^x$)—C(O)—N(R$^x$)$_2$, —N(R$^x$)—C(O)—R$^x$, —N(R$^x$)—S(O)—R$^x$, —N(R$^x$)—S(O)$_2$—R$^x$, —N(R$^x$)—S(O)—N(R$^x$)$_2$, and —N(R$^x$)—S(O)$_2$—N(R$^x$)$_2$;

R$^f$ is hydrogen, —F, —Cl, —Br, —I, —CN, —O—R$^y$, C$_{1-6}$alkyl, C$_{2-6}$alkenyl, or C$_{2-6}$alkynyl, wherein each C$_{1-6}$alkyl, C$_{2-6}$alkenyl, or C$_{2-6}$alkynyl is optionally substituted with one or more groups independently selected from oxo, —F, —Cl, —Br, —I, —NO$_2$, —N(R$^y$)$_2$, —CN, —C(O)—N(R$^y$)$_2$, —S(O)—N(R$^y$)$_2$, —S(O)$_2$—N(R$^y$)$_2$, —O—R$^y$, —S—R$^y$, —O—C(O)—R$^y$, —O—C(O)—O—R$^y$, —C(O)—R$^y$, —C(O)—O—R$^y$, —S(O)—R$^y$, —S(O)$_2$—R$^y$, —O—C(O)—N(R$^y$)$_2$, —N(R$^y$)—C(O)—OR$^y$, —N(R$^y$)—C(O)—N(R$^y$)$_2$, —N(R$^y$)—C(O)—R$^y$, —N(R$^y$)—S(O)—R$^y$, —N(R$^y$)—S(O)$_2$—R$^y$, —N(R$^y$)—S(O)—N(R$^y$)$_2$, and —N(R$^y$)—S(O)$_2$—N(R$^y$)$_2$;

each R$^g$ is independently selected from oxo, C$_{1-6}$alkyl, C$_{2-6}$alkenyl, C$_{2-6}$alkynyl, C$_{1-6}$haloalkyl, carbocyclyl, heterocyclyl, —F, —Cl, —Br, —I, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —O—C(O)—O—R$^z$, —C(O)—R$^z$, —C(O)—O—R$^z$, —S(O)—R$^z$, —S(O)$_2$—R$^z$, —O—C(O)—N(R$^z$)$_2$, —N(R$^z$)—C(O)—OR$^z$, —N(R$^z$)—C(O)—N(R$^z$)$_2$, —N(R$^z$)—C(O)—R$^z$, —N(R$^z$)—S(O)—R$^z$, —N(R$^z$)—S(O)$_2$—R$^z$, —N(R$^z$)—S(O)—N(R$^z$)$_2$, and —N(R$^z$)—S(O)$_2$—N(R$^z$)$_2$, wherein any C$_{1-6}$alkyl, C$_{2-6}$alkenyl, C$_{2-6}$alkynyl, C$_{1-6}$haloalkyl, carbocyclyl, or heterocyclyl is optionally substituted with one or more groups independently selected from oxo, halo, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —C(O)—R$^z$, —C(O)—O—R$^z$, —S(O)—R$^z$, —S(O)$_2$—R$^z$, —C(O)—N(R$^z$)$_2$, —N(R$^z$)—C(O)—R$^z$, —N(R$^z$)—S(O)—R$^z$, —N(R$^z$)—S(O)$_2$—R$^z$, C$_{1-6}$alkyl that is optionally substituted with one or more groups independently selected from oxo and halo, and heterocyclyl that is optionally substituted with one or more groups independently selected from oxo, halo, and C$_{1-6}$alkyl;

each R$^v$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, —N(R$^{va}$)$_2$, hydroxyl, cyano, C$_1$-C$_6$alkoxy, carbocyclyl, heterocyclyl, and C$_1$-C$_6$ alkyl that is optionally substituted with one or more groups independently selected from oxo and halo; or two R$^v$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo, —N(R$^{va}$)$_2$ and halo;

each R$^w$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, —N(R$^{wa}$)$_2$, hydroxyl, and C$_1$-C$_6$ alkyl that is optionally substituted with one or more groups independently selected from oxo and halo; or two R$^w$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^x$ is independently selected from hydrogen, C$_{1-6}$alkyl, C$_{2-6}$alkenyl, and C$_{2-6}$alkynyl, wherein each C$_{1-6}$alkyl, C$_{2-6}$alkenyl, or C$_{2-6}$alkynyl is optionally substituted with one or more groups independently selected from oxo, halo, amino, hydroxyl, and C$_1$-C$_6$ alkyl;

each R$^y$ is independently selected from hydrogen, C$_{1-6}$alkyl, C$_{2-6}$alkenyl, and C$_{2-6}$alkynyl, wherein each C$_{1-6}$alkyl, C$_{2-6}$alkenyl, or C$_{2-6}$alkynyl is optionally substituted with one or more groups independently selected from oxo, halo, amino, hydroxyl, and C$_1$-C$_6$ alkyl;

each R$^z$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, cyano, —N(R$^{za}$)$_2$, C$_1$-C$_6$alkoxy, carbocyclyl, —N(R$^{za}$)$_2$, —C(O)—N(R$^{za}$)$_2$, —O—R$^{za}$, —O—C(O)—R$^{za}$, —C(O)—O—R$^{za}$, —N(R$^{za}$)—C(O)—R$^{za}$, and C$_1$-C$_6$ alkyl that is optionally substituted with one or more groups independently selected from oxo and halo; or two R$^z$ are taken together with the nitrogen to which they are attached to form a heterocyclyl that is optionally substituted with one or more groups independently selected from oxo, halo, —N(R$^{za}$)$_2$, —C(O)—N(R$^{za}$)$_2$, —O—R$^{za}$, —O—C(O)—R$^{za}$, —C(O)—O—R$^{za}$, —N(R$^{za}$)—C(O)—R$^{za}$, and C$_{1-3}$alkyl that is optionally substituted with one or more groups independently selected from oxo and halo;

each R$^{va}$ is independently hydrogen or C$_{1-6}$alkyl, or two R$^{va}$ are taken together with a nitrogen to which they are attached to form a heterocyclyl;

each R$^{wa}$ is independently hydrogen or C$_{1-6}$alkyl, or two R$^{wa}$ are taken together with a nitrogen to which they are attached to form a heterocyclyl; and each R$^{za}$ is independently hydrogen or C$_{1-6}$alkyl, or two R$^{za}$ are taken together with a nitrogen to which they are attached to form a heterocyclyl;

Another aspect includes a composition comprising a compound of formula (I) or a pharmaceutically acceptable salt thereof, and a pharmaceutically acceptable adjuvant, carrier, or vehicle.

Another aspect includes a method for treating a bromodomain-mediated disorder in an animal comprising administering a compound of formula (I) or a pharmaceutically acceptable salt thereof to the animal.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a bromodomain-mediated disorder.

Another aspect includes the use of a compound of formula (I) or a pharmaceutically acceptable salt thereof to prepare a medicament for treating a bromodomain-mediated disorder in an animal (e.g. a mammal such as a human).

Another aspect includes compounds for the study of bromodomains.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O or (=O)$_2$.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms (C$_3$-C$_{12}$). In another embodiment, carbocyclyl includes C$_3$-C$_8$, C$_3$-C$_{10}$ or C$_5$-C$_{10}$. In other embodiment, carbocyclyl, as a monocycle, includes C$_3$-C$_8$, C$_3$-C$_6$ or C$_5$-C$_6$. In another embodiment, carbocyclyl, as a bicycle, includes C$_7$-C$_{12}$. In another embodiment, carbocyclyl, as a spiro system, includes C$_5$-C$_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain monovalent hydrocarbon radical. In one embodiment, the alkyl radical is one to eighteen carbon atoms (C$_1$-C$_{18}$). In other embodiments, the alkyl radical is C$_0$-C$_6$, C$_0$-C$_5$, C$_0$-C$_3$, C$_1$-C$_{12}$, C$_1$-C$_{10}$, C$_1$-C$_8$, $C_1$-$C_6$, $C_1$-$C_5$, $C_1$-$C_4$ or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), heptyl, octyl, nonyl, decyl, undecyl and dodecyl.

The term "alkenyl," as used herein, denotes a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched monovalent hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

The term "alkoxy" refers to a linear or branched monovalent radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein. The term heterocyclyl also includes $C_3$-$C_8$heterocycloalkyl, which is a saturated or partially unsaturated mono-, bi-, or spiro-ring system comprising 3-8 carbons and one or more (1, 2, 3, or 4) heteroatoms.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, $SO_2$), and any nitrogen heteroatom may optionally be quatemized (e.g. [NR$_4$]$^+$Cl$^-$, [NR$_4$]$^-$OH$^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomotpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6, 7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-wabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "polycycle" refers to a ring system with two or more (e.g. 2, 3, 4, or 5) rings that may be fused, bridged, or in a spiro relationship.

As used herein, the term "inhibitor" refers to a compound that binds to and inhibits a bromodomain with measurable affinity and activity. In certain embodiments, an inhibitor has an IC$_{50}$ or binding constant of less about 50 µM, less than about 1 µM, less than about 500 nM, less than about 100 nM, or less than about 10 nM.

The terms "measurable affinity" and "measurably inhibit," as used herein, refer to a measurable reduction in activity of a bromodomain between: (i) a sample comprising a compound of formula I or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extert and preferably stop) cancer cell infiltration into peripheral organs; inhibit (i.e., slow to some extert and preferably stop) tumor metastasis; inhibit to some extert, tumor growth; and/or relieve to some extert one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

As used herein, "a" or "an" means one or more, unless clearly indicated otherwise. As used herein, "another" means at least a second or more.

Exemplary Values

One embodiment provides a compound of formula (I) or a salt thereof, wherein:

$R^1$ is H, methyl, or ethyl;

$R^2$ is H, $C_{1-12}$alkyl, $C_{2-12}$alkenyl, $C_{2-12}$alkynyl, carbocyclyl, or heterocyclyl, wherein each $C_{1-12}$alkyl, $C_{2-12}$alkenyl, $C_{2-12}$alkynyl, carbocyclyl, or heterocyclyl of $R^2$ is optionally substituted with one or more groups $R^b$; and Q is a 5-membered heteroaryl that is optionally substituted with one or more groups $R^c$, or Q is:

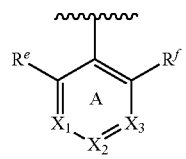

wherein ring A is optionally substituted with one or more groups $R^c$, or ring A is optionally fused with a carbocyclyl or a heterocyclyl to form a polycyclyl that is optionally substituted with one or more groups $R^g$;

$X_1$, $X_2$, and $X_3$ are each independently selected from $CR^c$ and N, provided that at least one of $X_1$, $X_2$, and $X_3$ is not N; and when A is optionally fused with a carbocyclyl or a heterocyclyl to form a polycyclyl, each of $X_1$, $X_2$, and $X_3$ can be C and can be a site of fusion;

each $R^b$ is independently selected from oxo, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —O—C(O)—O—R$^w$, —C(O)—R$^w$, —C(O)—O—R$^w$, —S(O)—R$^w$, —S(O)$_2$—R$^w$, —O—C(O)—N(R$^w$)$_2$, —N(R$^w$)—C(O)—OR$^w$, —N(R$^w$)—C(O)—N(R$^w$)$_2$, —N(R$^w$)—C(O)—R$^w$, —N(R$^w$)—S(O)—R$^w$, —N(R$^w$)—S(O)$_2$—R$^w$, —N(R$^w$)—S(O)—N(R$^w$)$_2$, and —N(R$^w$)—S(O)$_2$—N(R$^w$)$_2$, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO$_2$, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —C(O)—R$^w$, —C(O)—O—R$^w$, —S(O)—R$^w$, —S(O)$_2$—R$^w$, —C(O)—N(R$^w$)$_2$, —N(R$^w$)—C(O)—R$^w$, —N(R$^w$)—S(O)—R$^w$, —N(R$^w$)—S(O)$_2$—R$^w$ and $C_{1-6}$alkyl that is optionally substituted with one or more groups independently selected from oxo and halo;

each $R^c$ is independently selected from hydrogen, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—S(O)—R$^v$, —N(R$^v$)—S(O)$_2$—R$^v$, 6-membered monocyclic heterocyclyl and $C_{1-6}$alkyl that is optionally substituted with one or more groups independently selected from oxo and halo, wherein the 6-membered monocyclic heterocyclyl is optionally substituted with one or more $C_{1-6}$alkyl;

$R^e$ is hydrogen, —F, —Cl, —Br, —I, —CN, —O—R$^x$, $C_{1-6}$alkyl, $C_{2-6}$alkenyl, or $C_{2-6}$alkynyl, wherein each $C_{1-6}$alkyl, $C_{2-6}$alkenyl, or $C_{2-6}$alkynyl is optionally substituted with one or more groups independently selected from oxo, —F, —Cl, —Br, —I, —NO$_2$, —N(R$^x$)$_2$, —CN, —C(O)—N(R$^x$)$_2$, —S(O)—N(R$^x$)$_2$, —S(O)$_2$—N(R$^x$)$_2$, —O—R$^x$, —S—R$^x$, —O—C(O)—R$^x$, —O—C(O)—O—R$^x$, —C(O)—R$^x$, —C(O)—O—R$^x$, —S(O)—R$^x$, —S(O)$_2$—R$^x$, —O—C(O)—N(R$^x$)$_2$, —N(R$^x$)—C(O)—OR$^x$, —N(R$^x$)—C(O)—N(R$^x$)$_2$, —N(R$^x$)—C(O)—R$^x$, —N(R$^x$)—S(O)—R$^x$, —N(R$^x$)—S(O)$_2$—R$^x$, —N(R$^x$)—S(O)—N(R$^x$)$_2$, and —N(R$^x$)—S(O)$_2$—N(R$^x$)$_2$;

$R^f$ is hydrogen, —F, —Cl, —Br, —I, —CN, —O—R$^y$, $C_{1-6}$alkyl, $C_{2-6}$alkenyl, or $C_{2-6}$alkynyl, wherein each $C_{1-6}$alkyl, $C_{2-6}$alkenyl, or $C_{2-6}$alkynyl is optionally substituted with one or more groups independently selected from oxo, —F, —Cl, —Br, —I, —NO₂, —N(R^y)₂, —CN, —C(O)—N(R^y)₂, —S(O)—N(R^y)₂, —S(O)₂—N(R^y)₂, —O—R^y, —S—R^y, —O—C(O)—R^y, —O—C(O)—O—R^y, —C(O)—R^y, —C(O)—O—R^y, —S(O)—R^y, —S(O)₂—R^y, —O—C(O)—N(R^y)₂, —N(R^y)—C(O)—OR^y, —N(R^y)—C(O)—N(R^y)₂, —N(R^y)—C(O)—R^y, —N(R^y)—S(O)—R^y, —N(R^y)—S(O)₂—R^y, —N(R^y)—S(O)—N(R^y)₂, and —N(R^y)—S(O)₂—N(R^y)₂;

each $R^g$ is independently selected from oxo, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO₂, —N(R^z)₂, —CN, —C(O)—N(R^z)₂, —S(O)—N(R^z)₂, —S(O)₂—N(R^z)₂, —O—R^z, —S—R^z, —O—C(O)—R^z, —O—C(O)—O—R^z, —C(O)—R^z, —C(O)—O—R^z, —S(O)—R^z, —S(O)₂—R^z, —O—C(O)—N(R^z)₂, —N(R^z)—C(O)—OR^z, —N(R^z)—C(O)—N(R^z)₂, —N(R^z)—C(O)—R^z, —N(R^z)—S(O)—R^z, —N(R^z)—S(O)₂—R^z, —N(R^z)—S(O)—N(R^z)₂, and —N(R^z)—S(O)₂—N(R^z)₂, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO₂, —N(R^z)₂, —CN, —C(O)—N(R^z)₂, —S(O)—N(R^z)₂, —S(O)₂—N(R^z)₂, —O—R^z, —S—R^z, —O—C(O)—R^z, —C(O)—R^z, —C(O)—O—R^z, —S(O)—R^z, —S(O)₂—R^z, —C(O)—N(R^z)₂, —N(R^z)—C(O)—R^z, —N(R^z)—S(O)—R^z, —N(R^z)—S(O)₂—R^z, $C_{1-6}$alkyl that is optionally substituted with one or more groups independently selected from oxo and halo, and heterocyclyl that is optionally substituted with one or more groups independently selected from oxo, halo, and $C_{1-6}$alkyl;

each $R^v$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, or heterocyclyl is optionally substituted with one or more groups independently selected from oxo, halo, —N(R^{va})₂, hydroxyl, cyano, $C_1$-$C_6$alkoxy, carbocyclyl, heterocyclyl, and $C_1$-$C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo, —N(R^{va})₂ and halo;

each $R^w$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, or heterocyclyl is optionally substituted with one or more groups independently selected from oxo, halo, —N(R^{wa})₂, hydroxyl, and $C_1$-$C_6$ alkyl that is optionally substituted with one or more groups independently selected from oxo and halo; or two $R^w$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^x$ is independently selected from hydrogen, $C_{1-6}$alkyl, $C_{2-6}$alkenyl, and $C_{2-6}$alkynyl, wherein each $C_{1-6}$alkyl, $C_{2-6}$alkenyl, or $C_{2-6}$alkynyl is optionally substituted with one or more groups independently selected from oxo, halo, amino, hydroxyl, and $C_1$-$C_6$ alkyl;

each $R^y$ is independently selected from hydrogen, $C_{1-6}$alkyl, $C_{2-6}$alkenyl, and $C_{2-6}$alkynyl, wherein each $C_{1-6}$alkyl, $C_{2-6}$alkenyl, or $C_{2-6}$alkynyl is optionally substituted with one or more groups independently selected from oxo, halo, amino, hydroxyl, and $C_1$-$C_6$ alkyl;

each $R^z$ is independently selected from hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, or heterocyclyl is optionally substituted with one or more groups independently selected from oxo, halo, cyano, —N(R^{za})₂, $C_1$-$C_6$alkoxy, carbocyclyl, —N(R^{za})₂, —C(O)—N(R^{za})₂, —O—R^{za}, —O—C(O)—R^{za}, —C(O)—O—R^{za}, —N(R^{za})—C(O)—R^{za}, and $C_1$-$C_6$ alkyl that is optionally substituted with one or more groups independently selected from oxo and halo; or two $R^z$ are taken together with the nitrogen to which they are attached to form a heterocyclyl that is optionally substituted with one or more groups independently selected from oxo, halo, —N(R^{za})₂, —C(O)—N(R^{za})₂, —O—R^{za}, —O—C(O)—R^{za}, —C(O)—O—R^{za}, —N(R^{za})—C(O)—R^{za}, and $C_{1-3}$alkyl that is optionally substituted with one or more groups independently selected from oxo and halo;

each $R^{va}$ is independently hydrogen or $C_{1-6}$alkyl, or two $R^{va}$ are taken together with a nitrogen to which they are attached to form a heterocyclyl;

each $R^{wa}$ is independently hydrogen or $C_{1-6}$alkyl, or two $R^{wa}$ are taken together with a nitrogen to which they are attached to form a heterocyclyl; and each $R^{za}$ is independently hydrogen or $C_{1-6}$alkyl, or two $R^{za}$ are taken together with a nitrogen to which they are attached to form a heterocyclyl;

One embodiment provides a compound of formula (I) or a salt thereof, wherein:

$R^1$ is H, methyl, or ethyl;

$R^2$ is H, $C_{1-12}$alkyl, $C_{2-12}$alkenyl, $C_{2-12}$alkynyl, carbocyclyl, or heterocyclyl, wherein each $C_{1-12}$alkyl, $C_{2-12}$alkenyl, $C_{2-12}$alkynyl, carbocyclyl, or heterocyclyl of $R^2$ is optionally substituted with one or more groups $R^b$; and Q is a 5-membered heteroaryl that is optionally substituted with one or more groups $R^c$, or Q is:

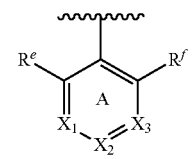

wherein ring A is optionally substituted with one or more groups $R^c$, or ring A is optionally fused with a carbocyclyl or a heterocyclyl to form a polycyclyl that is optionally substituted with one or more groups $R^g$;

$X_1$, $X_2$, and $X_3$ are each independently selected from $CR^c$ and N, provided that at least one of $X_1$, $X_2$, and $X_3$ is not N; and when A is optionally fused with a carbocyclyl or a heterocyclyl to form a polycyclyl, each of $X_1$, $X_2$, and $X_3$ can be C and can be a site of fusion;

each $R^b$ is independently selected from oxo, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO₂, —N(R^w)₂, —CN, —C(O)—N(R^w)₂, —S(O)—N(R^w)₂, —S(O)₂—N(R^w)₂, —O—R^w, —S—R^w, —O—C(O)—R^w, —O—C(O)—O—R^w, —C(O)—R^w, —C(O)—O—R^w, —S(O)—R^w, —S(O)₂—R^w, —O—C(O)—N(R^w)₂, —N(R^w)—C(O)—OR^w, —N(R^w)—C(O)—N(R^w)₂, —N(R^w)—C(O)—R^w, —N(R^w)—S(O)—R^w, —N(R^w)—S(O)₂—R^w, —N(R^w)—S(O)—N(R^w)₂, and —N(R^w)—S(O)₂—N(R^w)₂, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO₂, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —C(O)—R$^w$, —C(O)—O—R$^w$, —S(O)—R$^w$, —S(O)$_2$—R$^w$, —C(O)—N(R$^w$)$_2$, —N(R$^w$)—C(O)—R$^w$, —N(R$^w$)—S(O)—R$^w$, —N(R$^w$)—S(O)$_2$—R$^w$ and C$_{1-6}$alkyl that is optionally substituted with one or more groups independently selected from oxo and halo;

each R$^c$ is independently selected from hydrogen, C$_{1-6}$alkyl, C$_{2-6}$alkenyl, C$_{2-6}$alkynyl, C$_{1-6}$haloalkyl, carbocyclyl, heterocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any C$_{1-6}$alkyl, C$_{2-6}$alkenyl, C$_{2-6}$alkynyl, C$_{1-6}$haloalkyl, carbocyclyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$ and C$_{1-6}$alkyl that is optionally substituted with one or more groups independently selected from oxo and halo;

R$^e$ is hydrogen, —F, —Cl, —Br, —I, —CN, —O—R$^x$, C$_{1-6}$alkyl, C$_{2-6}$alkenyl, or C$_{2-6}$alkynyl, wherein each C$_{1-6}$alkyl, C$_{2-6}$alkenyl, or C$_{2-6}$alkynyl is optionally substituted with one or more groups independently selected from oxo, —F, —Cl, —Br, —I, —NO$_2$, —N(R$^x$)$_2$, —CN, —C(O)—N(R$^x$)$_2$, —S(O)—N(R$^x$)$_2$, —S(O)$_2$—N(R$^x$)$_2$, —O—R$^x$, —S—R$^x$, —O—C(O)—R$^x$, —O—C(O)—O—R$^x$, —C(O)—R$^x$, —C(O)—O—R$^x$, —S(O)—R$^x$, —S(O)$_2$—R$^x$, —O—C(O)—N(R$^x$)$_2$, —N(R$^x$)—C(O)—OR$^x$, —N(R$^x$)—C(O)—N(R$^x$)$_2$—N(R$^x$)—C(O)—R$^x$, —N(R$^x$)—S(O)—R$^x$, —N(R$^x$)—S(O)$_2$—R$^x$, —N(R$^x$)—S(O)—N(R$^x$)$_2$, and —N(R$^x$)—S(O)$_2$—N(R$^x$)$_2$;

R$^f$ is hydrogen, —F, —Cl, —Br, —I, —CN, —O—R$^y$, C$_{1-6}$alkyl, C$_{2-6}$alkenyl, or C$_{2-6}$alkynyl, wherein each C$_{1-6}$alkyl, C$_{2-6}$alkenyl, or C$_{2-6}$alkynyl is optionally substituted with one or more groups independently selected from oxo, —F, —Cl, —Br, —I, —NO$_2$, —N(R$^y$)$_2$, —CN, —C(O)—N(R$^y$)$_2$, —S(O)—N(R$^y$)$_2$, —S(O)$_2$—N(R$^y$)$_2$, —O—R$^y$, —S—R$^y$, —O—C(O)—R$^y$, —C(O)—R$^y$, —C(O)—O—R$^y$, —S(O)—R$^y$, —S(O)$_2$—R$^y$, —O—C(O)—N(R$^y$)$_2$, —N(R$^y$)—C(O)—OR$^y$, —N(R$^y$)—C(O)—N(R$^y$)$_2$, —N(R$^y$)—C(O)—R$^y$, —N(R$^y$)—S(O)—R$^y$, —N(R$^y$)—S(O)$_2$—R$^y$, —N(R$^y$)—S(O)—N(R$^y$)$_2$, and —N(R$^y$)—S(O)$_2$—N(R$^y$)$_2$;

each R$^g$ is independently selected from oxo, C$_{1-6}$alkyl, C$_{2-6}$alkenyl, C$_{2-6}$alkynyl, C$_{1-6}$haloalkyl, carbocyclyl, heterocyclyl, —F, —Cl, —Br, —I, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —O—C(O)—O—R$^z$, —C(O)—R$^z$, —C(O)—O—R$^z$, —S(O)—R$^z$, —S(O)$_2$—R$^z$, —O—C(O)—N(R$^z$)$_2$, —N(R$^z$)—C(O)—OR$^z$, —N(R$^z$)—C(O)—N(R$^z$)$_2$, —N(R$^z$)—C(O)—R$^z$, —N(R$^z$)—S(O)—R$^z$, —N(R$^z$)—S(O)$_2$—R$^z$, —N(R$^z$)—S(O)—N(R$^z$)$_2$, and —N(R$^z$)—S(O)$_2$—N(R$^z$)$_2$, wherein any C$_{1-6}$alkyl, C$_{2-6}$alkenyl, C$_{2-6}$alkynyl, C$_{1-6}$haloalkyl, carbocyclyl, or heterocyclyl is optionally substituted with one or more groups independently selected from oxo, halo, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —C(O)—R$^z$, —C(O)—O—R$^z$, —S(O)—R$^z$, —S(O)$_2$—R$^z$, —C(O)—N(R$^z$)$_2$, —N(R$^z$)—C(O)—R$^z$, —N(R$^z$)—S(O)—R$^z$, —N(R$^z$)—S(O)$_2$—R$^z$, C$_{1-6}$alkyl that is optionally substituted with one or more groups independently selected from oxo and halo, and heterocyclyl that is optionally substituted with one or more groups independently selected from oxo, halo, and C$_{1-6}$alkyl;

each R$^v$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, —N(R$^{va}$)$_2$, hydroxyl, carbocyclyl, heterocyclyl, and C$_1$-C$_6$ alkyl that is optionally substituted with one or more groups independently selected from oxo and halo; or two R$^v$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^w$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, —N(R$^{wa}$)$_2$, hydroxyl, and C$_1$-C$_6$alkyl that is optionally substituted with one or more groups independently selected from oxo and halo; or two R$^w$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^x$ is independently selected from hydrogen, C$_{1-6}$alkyl, C$_{2-6}$alkenyl, and C$_{2-6}$alkynyl, wherein each C$_{1-6}$alkyl, C$_{2-6}$alkenyl, or C$_{2-6}$alkynyl is optionally substituted with one or more groups independently selected from oxo, halo, amino, hydroxyl, and C$_1$-C$_6$ alkyl;

each R$^y$ is independently selected from hydrogen, C$_{1-6}$alkyl, C$_{2-6}$alkenyl, and C$_{2-6}$alkynyl, wherein each C$_{1-6}$alkyl, C$_{2-6}$alkenyl, or C$_{2-6}$alkynyl is optionally substituted with one or more groups independently selected from oxo, halo, amino, hydroxyl, and C$_1$-C$_6$ alkyl;

each R$^z$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, cyano, —N(R$^{za}$)$_2$, C$_1$-C$_6$alkoxy, carbocyclyl, —N(R$^{za}$)$_2$, —C(O)—N(R$^{za}$)$_2$, —O—R$^{za}$, —O—C(O)—R$^{za}$, —C(O)—O—R$^{za}$, —N(R$^{za}$)—C(O)—R$^{za}$, and C$_1$-C$_6$ alkyl that is optionally substituted with one or more groups independently selected from oxo and halo; or two R$^z$ are taken together with the nitrogen to which they are attached to form a heterocyclyl that is optionally substituted with one or more groups independently selected from oxo, halo, —N(R$^{za}$)$_2$, —C(O)—N(R$^{za}$)$_2$, —O—R$^{za}$, —O—C(O)—R$^{za}$, —C(O)—O—R$^{za}$, —N(R$^{za}$)—C(O)—R$^{za}$, and C$_{1-3}$alkyl that is optionally substituted with one or more groups independently selected from oxo and halo;

each R$^{va}$ is independently hydrogen or C$_{1-6}$alkyl, or two R$^{va}$ are taken together with a nitrogen to which they are attached to form a heterocyclyl;

each R$^{wa}$ is independently hydrogen or C$_{1-6}$alkyl, or two R$^{va}$ are taken together with a nitrogen to which they are attached to form a heterocyclyl; and each $R^{za}$ is independently hydrogen or $C_{1-6}$alkyl, or two $R^{za}$ are taken together with a nitrogen to which they are attached to form a heterocyclyl.

With respect to the embodiments for formula (I) noted above, the following exemplary values are provided. It is to be understood that two or more embodiments provided herein may be combined.

In certain embodiments $R^1$ is H.
In certain embodiments $R^1$ is methyl.
In certain embodiments $R^1$ is ethyl.
In certain embodiments $R^2$ is H.
In certain embodiments $R^2$ is methyl.
In certain embodiments Q is a 5-membered heteroaryl that is optionally substituted with one or more groups $R^c$.
In certain embodiments Q is a phenyl that is optionally substituted with one or more groups $R^c$.
In certain embodiments Q is a phenyl that is optionally substituted with one or more groups $R^c$ at the 3, 4, 5 or 6 positions of the phenyl.
In certain embodiments Q is a phenyl that is optionally substituted with one or more groups $R^c$ at the 3, 4 or 5 positions of the phenyl.
In certain embodiments Q is a furyl, thienyl, pyrrolyl, imidazolyl, thiazolyl, oxazolyl, isoxazolyl, thiazolyl, isothiazolyl, or triazolyl that is optionally substituted with one or more groups $R^c$.
In certain embodiments Q is:

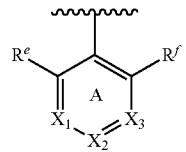

wherein ring A is optionally substituted with one or more groups $R^c$.

In certain embodiments Q is:

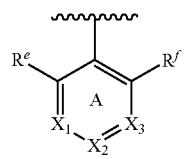

wherein ring A is substituted with one or more groups $R^c$ independently selected from $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$ and $C_{1-6}$alkyl that is optionally substituted with one or more groups independently selected from oxo and halo.

In certain embodiments Q is:

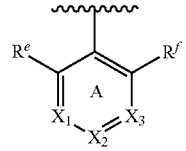

wherein ring A is fused with a carbocyclyl or a heterocyclyl to form a polycyclyl that is optionally substituted with one or more groups $R^g$.

In certain embodiments Q is:

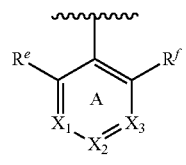

wherein ring A is optionally substituted with one or more groups $R^c$, or ring A is optionally fused with a carbocyclyl or a heterocyclyl to form a polycyclyl that is optionally substituted with one or more groups $R^g$.

In certain embodiments $X_1$ is $CR^c$, $X_2$ is $CR^c$, and $X_3$ is $CR^c$.
In certain embodiments $X_1$ is N, $X_2$ is $CR^c$, and $X_3$ is $CR^c$.
In certain embodiments $X_1$ is $CR^c$, $X_2$ is N, and $X_3$ is $CR^c$.
In certain embodiments $X_1$ is N, $X_2$ is N, and $X_3$ is $CR^c$.
In certain embodiments $X_1$ is N, $X_2$ is $CR^c$, and $X_3$ is N.
In certain embodiments $R^e$ is hydrogen.
In certain embodiments $R^e$ and $R^f$ are each hydrogen.
In certain embodiments ring A is fused with a carbocyclyl to form a polycyclyl that is optionally substituted with one or more groups $R^g$.
In certain embodiments ring A is fused with a heterocyclyl to form a polycyclyl that is optionally substituted with one or more groups $R^g$.
In certain embodiments each $R^c$ is independently selected from hydrogen, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$ and $C_{1-6}$alkyl that is optionally substituted with one or more groups independently selected from oxo and halo.

In certain embodiments each $R^c$ is independently selected from hydrogen, $C_{1-6}$alkyl, heterocyclyl, —F, —Cl, —N(R$^v$)$_2$, —CN, —C(O)—N(R$^v$)$_2$, —O—R$^v$, —C(O)—O—R$^v$, —N(R$^v$)—C(O)—OR$^v$ and —N(R$^v$)—C(O)—R$^v$, wherein any $C_{1-6}$alkyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$, 6-membered monocyclic heterocyclyl and $C_{1-6}$alkyl that is optionally substituted with one or more groups independently selected from oxo and halo, wherein the 6-membered monocyclic heterocyclyl is optionally substituted with $C_{1-6}$alkyl.

In certain embodiments each $R^c$ is independently selected from hydrogen, $C_{1-6}$alkyl, heterocyclyl, —CN, —C(O)—N (R$^v$)$_2$, —N(R$^v$)—C(O)—OR$^v$ and —N(R$^v$)—C(O)—R$^v$, wherein any $C_{1-6}$alkyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$, 6-membered monocyclic heterocyclyl and $C_{1-6}$alkyl that is optionally substituted with one or more groups independently selected from oxo and halo, wherein the 6-membered monocyclic heterocyclyl is optionally substituted with $C_{1-6}$alkyl.

In certain embodiments each $R^c$ is independently selected from hydrogen, $C_{1-6}$alkyl, heterocyclyl, —CN, —C(O)—N (R$^v$)$_2$, —N(R$^v$)—C(O)—OR$^v$ and —N(R$^v$)—C(O)—R$^v$, wherein any $C_{1-6}$alkyl, or heterocyclyl is optionally substituted with one or more groups independently selected from —O—R$^v$, 6-membered monocyclic heterocyclyl and $C_{1-6}$alkyl that is optionally substituted with one or more groups independently selected from oxo and halo, wherein the 6-membered monocyclic heterocyclyl is optionally substituted with $C_{1-6}$alkyl.

In certain embodiments each $R^g$ is independently selected from oxo, $C_{1-6}$alkyl, carbocyclyl, heterocyclyl, —F, —Cl, —N(R$^z$)$_2$, —CN, —C(O)—N(R$^z$)$_2$, —O—R$^z$, —C(O)—R$^z$, —C(O)—O—R$^z$, —N(R$^z$)—C(O)—OR$^z$ and —N(R$^z$)—C (O)—, wherein any $C_{1-6}$alkyl, carbocyclyl or heterocyclyl is optionally substituted with one or more groups independently selected from oxo, halo, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —C(O)—R$^z$, —C(O)—O—R$^z$, —S(O)—R$^z$, —S(O)$_2$—R$^z$, —C(O)—N (R$^z$)$_2$, —N(R$^z$)—C(O)—R$^z$, —N(R$^z$)—S(O)—R$^z$, —N(R$^z$)—S(O)$_2$—R$^z$, $C_{1-6}$alkyl that is optionally substituted with one or more groups independently selected from oxo and halo, and heterocyclyl that is optionally substituted with one or more groups independently selected from oxo, halo, and $C_{1-6}$alkyl.

In certain embodiments each $R^g$ is independently selected from oxo, $C_{1-6}$alkyl, carbocyclyl, heterocyclyl and —C(O)—O—R$^z$ wherein any $C_{1-6}$alkyl, carbocyclyl or heterocyclyl is optionally substituted with one or more groups independently selected from oxo, halo, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —C(O)—R$^z$, —C(O)—O—R$^z$, —S(O)—R$^z$, —S(O)$_2$—R$^z$, —C(O)—N (R$^z$)$_2$, —N(R$^z$)—C(O)—R$^z$, —N(R$^z$)—S(O)—R$^z$, —N(R$^z$)—S(O)$_2$—R$^z$, $C_{1-6}$alkyl that is optionally substituted with one or more groups independently selected from oxo and halo, and heterocyclyl that is optionally substituted with one or more groups independently selected from oxo, halo, and $C_{1-6}$alkyl.

In certain embodiments each $R^g$ is independently selected from oxo, $C_{1-6}$alkyl, carbocyclyl, heterocyclyl and —C(O)—O—R$^z$ wherein any $C_{1-6}$alkyl, carbocyclyl, or heterocyclyl is optionally substituted with one or more —O—R$^z$ groups.

In certain embodiments Q is selected from: phenyl, 2-oxoindolin-5-yl, 1-tert-butoxycarbonyl-3,4-dihydro-2H-quinolin-6-yl, 2,3,3a,5-tetrahydropyrrolo[1,2-a]quinoxaline-1,4-dione-8-yl, 3-methyl-3,4-dihydro-1H-quinoxalin-2-one-6-yl, 1,3,4,5-tetrahydro-4-methyl-1,5-benzodiazepin-2-one-7-yl, 5,7,7a,8,9,10-hexahydropyrrolo[2,1-d][1,5]benzodiazepin-6-one-2-yl, 4-(2-thienyl)-1,3,4,5-tetrahydro-1,5-benzodiazepin-2-one-7-yl, 3-aminocarbonylphenyl, 3-cyanophenyl, 4-hydroxymethylphenyl, 4-(3-fluoroazetidin-1-ylcarbonyl)phenyl, 4-(1-pyrrolidinylcarbonyl)phenyl, 4-(4-methylpiperidine-1-ylcarbonyl)phenyl, 4-(4-acetylpiperazine-1-ylcarbonyl)phenyl, 4-(4-(aminocarbonyl)piperidin-1-ylcarbonyl)phenyl, 4-(N-(pyrid-3-yl)aminocarbonyl)phenyl, 4-(2-phenylpropanooyl)phenyl, 4-(N-methyl-N-(cyanomethyl)aminocarbonyl)phenyl, 4-(N-(2-methoxyethyl)aminocarbonyl)phenyl, 1-tert-butoxycarbonyl-3,4-dihydro-2H-quinolin-7-yl, 4-(tert-butoxycarbonylamino)phenyl, 1,3,4,5-tetrahydro-1,5-benzodiazepin-2-one-7-yl, 3-(N,N-dimethylaminocarbonyl) phenyl, 4-(1-hydroxy-1-methylethyl)phenyl, 4-(1methylpiperidin-4-yl)phenyl, 4-(1methylpiperidin-4-ylmethyl)phenyl, 4-(N-(2-methoxyethylcarbonyl)amino)phenyl, 2-methyl-4H-1,4-benzoxazin-3-one-7-yl, 4-(N,N-dimethylaminocarbonyl)phenyl, 4-(4-methyl-3-oxo-piperazine-1-ylcarbonyl)phenyl, 4-(3,3-difluoroazetidin-1-ylcarbonyl) phenyl, 4-(N-phenylaminocarbonyl)phenyl, 4-(2-methyl-3,4-dihydro-1H-isoquinolin-6-yl, 3-(N-methylaminocarbonyl)phenyl, 4-(morpholinocarbonyl) phenyl, 3-(N-benzylaminocarbonyl)phenyl, 3-(1-methylpiperidin-4-yl)phenyl, 3-(1-methylpiperidin-4-ylmethyl)phenyl, and 3-(2-hydroxyethyl)-3-phenylindan-5-yl.

In certain embodiments the compound is selected from:
6-methyl-4-phenyl-1H-pyrrolo[2,3-c]pyridin-7(6H)-one;
6-methyl-4-(2-oxoindolin-5-yl)-1H-pyrrolo[2,3-c]pyridin-7-one;
N-(2-methoxyethyl)-4-(6-methyl-7-oxo-1H-pyrrolo[2,3-c]pyridin-4-yl)benzamide;
tert-butyl 6-(6-methyl-7-oxo-1H-pyrrolo[2,3-c]pyridin-4-yl)-3,4-dihydro-2H-quinoline-1-carboxylate;
tert-butyl 7-(6-methyl-7-oxo-1H-pyrrolo[2,3-c]pyridin-4-yl)-3,4-dihydro-2H-quinoline-1-carboxylate;
tert-butyl N-[4-(6-methyl-7-oxo-1H-pyrrolo[2,3-c]pyridin-4-yl)phenyl]carbamate;
3-methoxy-N-[4-(6-methyl-7-oxo-1H-pyrrolo[2,3-c]pyridin-4-yl)phenyl]propanamide;
4-(3-(2-hydroxyethyl)-3-phenyl-2,3-dihydro-1H-inden-5-yl)-6-methyl-1H-pyrrolo[2,3-c]pyridin-7(6H)-one;
8-(6-methyl-7-oxo-6,7-dihydro-1H-pyrrolo[2,3-c]pyridin-4-yl)-3,3a-dihydropyrrolo[1,2-a]quinoxaline-1,4(2H,5H)-dione;
3-methyl-6-(6-methyl-7-oxo-1H-pyrrolo[2,3-e]pyridin-4-yl)-3,4-dihydro-1H-quinoxalin-2-one;
3-methyl-7-(6-methyl-7-oxo-1H-pyrrolo[2,3-c]pyridin-4-yl)-1,3,4,5-tetrahydro-1,5-benzodiazepin-2-one;
7-(6-methyl-7-oxo-1H-pyrrolo[2,3-c]pyridin-4-yl)-1,3,4,5-tetrahydro-1,5-benzodiazepin-2-one;
4-methyl-7-(6-methyl-7-oxo-1H-pyrrolo[2,3-e]pyridin-4-yl)-1,3,4,5-tetrahydro-1,5-benzodiazepin-2-one;
3-isopropyl-6-(6-methyl-7-oxo-1H-pyrrolo[2,3-c]pyridin-4-yl)-1H-quinoxalin-2-one;
2-(6-methyl-7-oxo-1H-pyrrolo[2,3-c]pyridin-4-yl)-5,7,7a,8,9,10-hexahydropyrrolo[2,1-d][1,5]benzodiazepin-6-one;

2-methyl-7-(6-methyl-7-oxo-1H-pyrrolo[2,3-e]pyridin-4-yl)-4H-1,4-benzoxazin-3-one;
7-(6-methyl-7-oxo-1H-pyrrolo[2,3-c]pyridin-4-yl)-4-(2-thienyl)-1,3,4,5-tetrahydro-1,5-benzodiazepin-2-one;
N,N-dimethyl-4-(6-methyl-7-oxo-1H-pyrrolo[2,3-c]pyridin-4-yl)benzamide;
N,N-dimethyl-3-(7-oxo-6-propyl-1H-pyrrolo[2,3-c]pyridin-4-yl)benzamide;
3-(6-ethyl-7-oxo-1H-pyrrolo[2,3-c]pyridin-4-yl)-N,N-dimethyl-benzamide;
3-(6-methyl-7-oxo-1H-pyrrolo[2,3-c]pyridin-4-yl)benzamide;
N,N-dimethyl-3-(6-methyl-7-oxo-1H-pyrrolo[2,3-c]pyridin-4-yl)benzamide;
3-(6-methyl-7-oxo-1H-pyrrolo[2,3-c]pyridin-4-yl)benzonitrile;
N-methyl-3-(6-methyl-7-oxo-1H-pyrrolo[2,3-e]pyridin-4-yl)benzamide;
4-[4-(hydroxymethyl)phenyl]-6-methyl-1H-pyrrolo[2,3-e]pyridin-7-one;
6-methyl-4-(4-(4-methyl-3-oxopiperazine-1-carbonyl)phenyl)-1H-pyrrolo[2,3-c]pyridin-7(6H)-one;
4-[4-(3-fluoroazetidine-1-carbonyl)phenyl]-6-methyl-1H-pyrrolo[2,3-e]pyridin-7-one;
4-[4-(3,3-difluoroazetidine-1-carbonyl)phenyl]-6-methyl-1H-pyrrolo[2,3-c]pyridin-7-one;
6-methyl-4-[4-(pyrrolidine-1-carbonyl)phenyl]-1H-pyrrolo[2,3-c]pyridin-7-one;
6-methyl-4-[4-(morpholine-4-carbonyl)phenyl]-1H-pyrrolo[2,3-c]pyridin-7-one;
6-methyl-4-[4-(4-methylpiperidine-1-carbonyl)phenyl]-1H-pyrrolo[2,3-e]pyridin-7-one;
4-[4-(4-acetylpiperazine-1-carbonyl)phenyl]-6-methyl-1H-pyrrolo[2,3-c]pyridin-7-one,
1-[4-(6-methyl-7-oxo-1H-pyrrolo[2,3-c]pyridin-4-yl)benzoyl]piperidine-4-carboxamide;
4-(6-methyl-7-oxo-1H-pyrrolo[2,3-c]pyridin-4-yl)-N-(3-pyridyl)benzamide;
4-(6-methyl-7-oxo-1H-pyrrolo[2,3-c]pyridin-4-yl)-N-phenyl-benzamide;
N-methyl-4-(6-methyl-7-oxo-1H-pyrrolo[2,3-c]pyridin-4-yl)-N-phenyl-benzamide;
N-benzyl-4-(6-methyl-7-oxo-1H-pyrrolo[2,3-c]pyridin-4-yl)benzamide;
N-(cyanomethyl)-N-methyl-4-(6-methyl-7-oxo-1H-pyrrolo[2,3-c]pyridin-4-yl)benzamide;
4-[4-(1-hydroxy-1-methyl-ethyl)phenyl]-6-methyl-1H-pyrrolo[2,3-c]pyridin-7-one;
4-[4-(1-hydroxy-1-methyl-ethyl)phenyl]-6-isopropyl-1H-pyrrolo[2,3-c]pyridin-7-one;
6-cyclopropyl-4-(4-(2-hydroxypropan-2-yl)phenyl)-1H-pyrrolo[2,3-c]pyridin-7(6H)-one;
6-methyl-4-[4-(1-methyl-4-piperidyl)phenyl]-1H-pyrrolo[2,3-c]pyridin-7-one;
6-methyl-4-[3-(1-methyl-4-piperidyl)phenyl]-1H-pyrrolo[2,3-c]pyridin-7-one;
6-methyl-4-(2-methyl-3,4-dihydro-1H-isoquinolin-6-yl)-1H-pyrrolo[2,3-c]pyridin-7-one;
6-methyl-4-[4-[(1-methyl-4-piperidyl)methyl]phenyl]-1H-pyrrolo[2,3-c]pyridin-7-one;
6-methyl-4-[3-[(1-methyl-4-piperidyl)methyl]phenyl]-1H-pyrrolo[2,3-c]pyridin-7-one; and
3-(2,6-dimethyl-7-oxo-1H-pyrrolo[2,3-c]pyridin-4-yl)-N,N-dimethyl-benzamide
and salts thereof.

In certain embodiments the compound is selected from:
N,N-dimethyl-3-(7-oxo-6-propyl-1H-pyrrolo[2,3-c]pyridin-4-yl)benzamide;
4-[4-(1-hydroxy-1-methyl-ethyl)phenyl]-6-isopropyl-1H-pyrrolo[2,3-c]pyridin-7-one; and
6-cyclopropyl-4-(4-(2-hydroxypropan-2-yl)phenyl)-1H-pyrrolo[2,3-c]pyridin-7(6H)-one;
and salts thereof.

In certain embodiments the compound is selected from:

| Structure | Name |
|---|---|
| 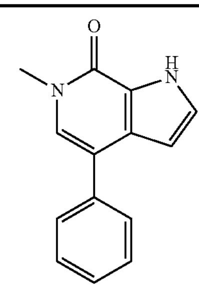 | 6-methyl-4-phenyl-1H-pyrrolo[2,3-c]pyridin-7-one |
| 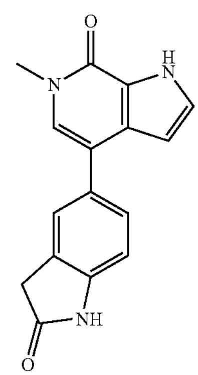 [SMILES: Cn1cc(-c2ccc3c(c2)CC(=O)N3)c2cc[nH]c2c1=O] | 6-methyl-4-(2-oxoindolin-5-yl)-1H-pyrrolo[2,3-c]pyridin-7-one |

| Structure | Name |
|---|---|
| 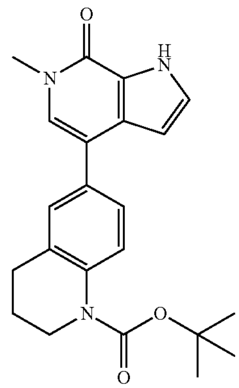 [SMILES: Cn1cc(-c2ccc3c(c2)CCCN3C(=O)OC(C)(C)C)c2cc[nH]c2c1=O] | tert-butyl 6-(6-methyl-7-oxo-1H-pyrrolo[2,3-c]pyridin-4-yl)-3,4-dihydro-2H-quinoline-1-carboxylate |
| 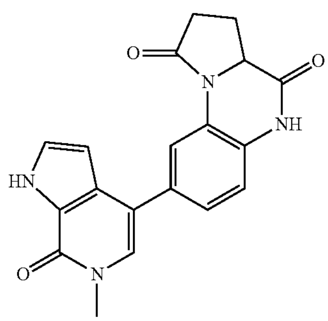 [SMILES: Cn1cc(-c2ccc3c(c2)N2C(=O)CCC2C(=O)N3)c2cc[nH]c2c1=O] | 8-(6-methyl-7-oxo-1H-pyrrolo[2,3-c]pyridin-4-yl)-2,3,3a,5-tetrahydropyrrolo[1,2-a]quinoxaline-1,4-dione;2,2,2-trifluoroacetic acid |
| 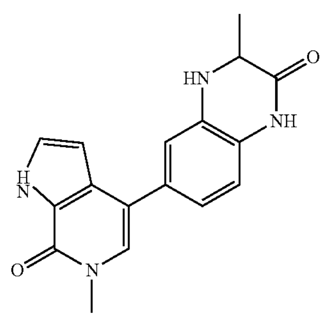 [SMILES: CC1Nc2cc(-c3cn(C)c(=O)c4[nH]ccc34)ccc2NC1=O] | 3-methyl-6-(6-methyl-7-oxo-1H-pyrrolo[2,3-c]pyridin-4-yl)-3,4-dihydro-1H-quinoxalin-2-one |
| 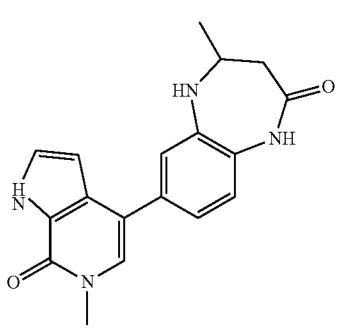 [SMILES: CC1CC(=O)Nc2ccc(-c3cn(C)c(=O)c4[nH]ccc34)cc2N1] | 4-methyl-7-(6-methyl-7-oxo-1H-pyrrolo[2,3-c]pyridin-4-yl)-1,3,4,5-tetrahydro-1,5-benzodiazepin-2-one |

-continued

| Structure | Name |
|---|---|
| 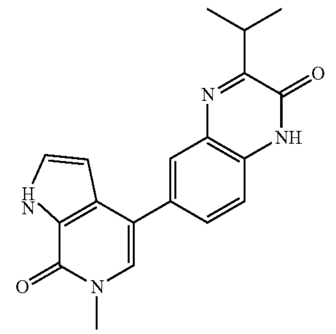 [SMILES: CC(C)c1nc2cc(-c3cn(C)c(=O)c4[nH]ccc34)ccc2[nH]c1=O] | 3-isopropyl-6-(6-methyl-7-oxo-1H-pyrrolo[2,3-c]pyridin-4-yl)-1H-quinoxalin-2-one |
| 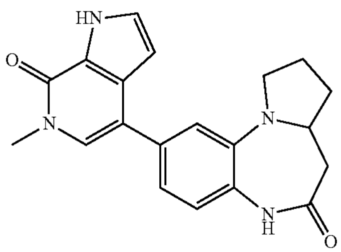 [SMILES: Cn1cc(-c2ccc3c(c2)N2CCCC2CC(=O)N3)c2cc[nH]c2c1=O] | 2-(6-methyl-7-oxo-1H-pyrrolo[2,3-c]pyridin-4-yl)-5,7,7a,8,9,10-hexahydropyrrolo[2,1-d][1,5]benzodiazepin-6-one |
| 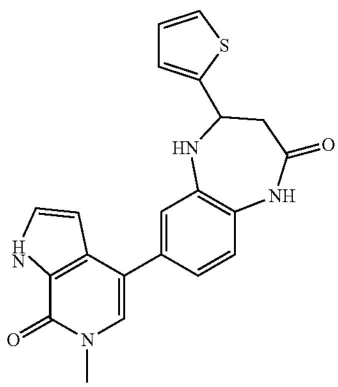 [SMILES: Cn1cc(-c2ccc3c(c2)NC(c2cccs2)CC(=O)N3)c2cc[nH]c2c1=O] | 7-(6-methyl-7-oxo-1H-pyrrolo[2,3-c]pyridin-4-yl)-4-(2-thienyl)-1,3,4,5-tetrahydro-1,5-benzodiazepin-2-one |
| 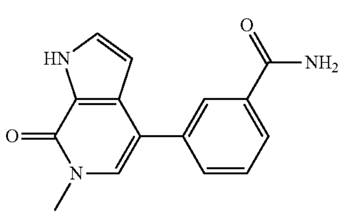 [SMILES: Cn1cc(-c2cccc(C(N)=O)c2)c2cc[nH]c2c1=O] | 3-(6-methyl-7-oxo-1H-pyrrolo[2,3-c]pyridin-4-yl)benzamide |
| 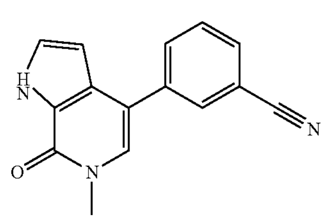 [SMILES: Cn1cc(-c2cccc(C#N)c2)c2cc[nH]c2c1=O] | 3-(6-methyl-7-oxo-1H-pyrrolo[2,3-c]pyridin-4-yl)benzonitrile |
| 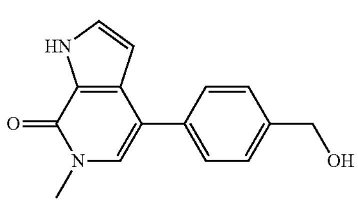 [SMILES: Cn1cc(-c2ccc(CO)cc2)c2cc[nH]c2c1=O] | 4-[4-(hydroxymethyl)phenyl]-6-methyl-1H-pyrrolo[2,3-c]pyridin-7-one |

-continued
| Structure | Name |
|---|---|
| 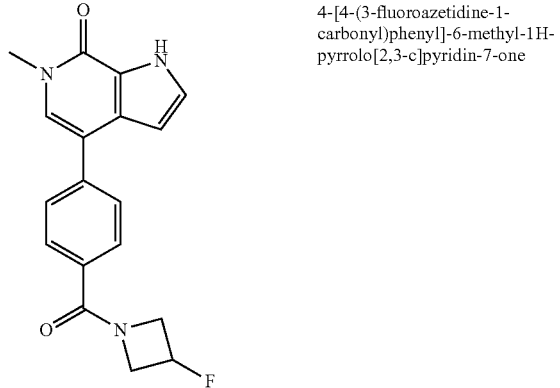 | 4-[4-(3-fluoroazetidine-1-carbonyl)phenyl]-6-methyl-1H-pyrrolo[2,3-c]pyridin-7-one |
| 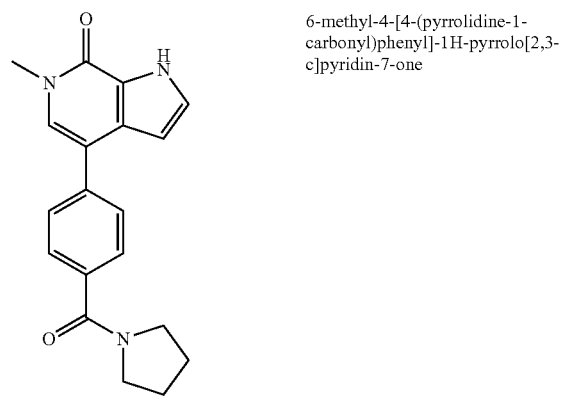 | 6-methyl-4-[4-(pyrrolidine-1-carbonyl)phenyl]-1H-pyrrolo[2,3-c]pyridin-7-one |
| 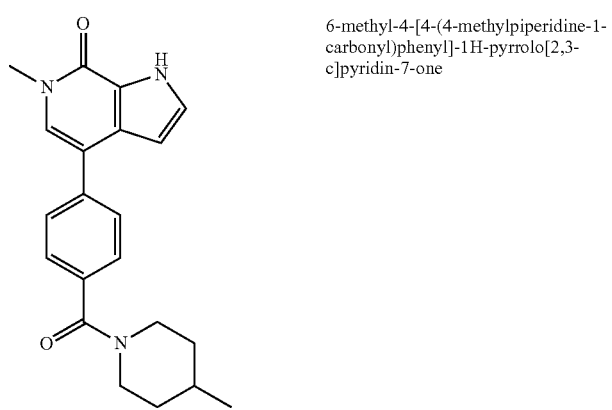 | 6-methyl-4-[4-(4-methylpiperidine-1-carbonyl)phenyl]-1H-pyrrolo[2,3-c]pyridin-7-one |

| Structure | Name |
|---|---|
| 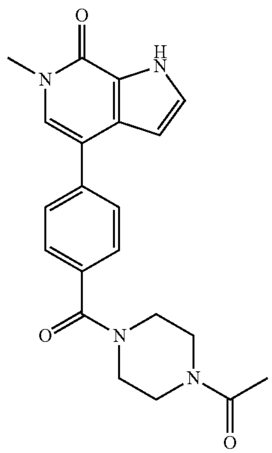 [SMILES: CC(=O)N1CCN(C(=O)c2ccc(-c3cn(C)c(=O)c4[nH]ccc34)cc2)CC1] | 4-[4-(4-acetylpiperazine-1-carbonyl)phenyl]-6-methyl-1H-pyrrolo[2,3-c]pyridin-7-one |
| 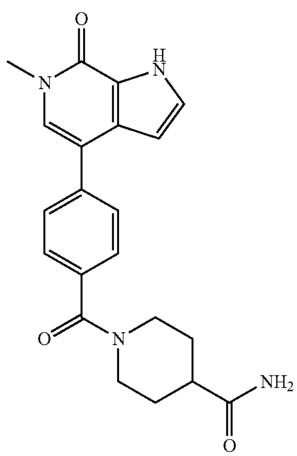 [SMILES: Cn1cc(-c2ccc(C(=O)N3CCC(C(N)=O)CC3)cc2)c2cc[nH]c2c1=O] | 1-[4-(6-methyl-7-oxo-1H-pyrrolo[2,3-c]pyridin-4-yl)benzoyl]piperidine-4-carboxamide |
| 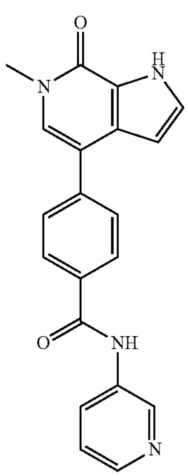 | 4-(6-methyl-7-oxo-1H-pyrrolo[2,3-c]pyridin-4-yl)-N-(3-pyridyl)benzamide |

| Structure | Name |
|---|---|
| 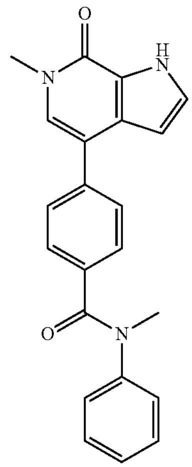 [SMILES: CN(C(=O)c1ccc(-c2cn(C)c(=O)c3[nH]ccc23)cc1)c1ccccc1] | N-methyl-4-(6-methyl-7-oxo-1H-pyrrolo[2,3-c]pyridin-4-yl)-N-phenyl-benzamide |
| 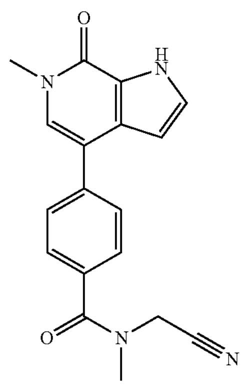 [SMILES: CN(CC#N)C(=O)c1ccc(-c2cn(C)c(=O)c3[nH]ccc23)cc1] | N-(cyanomethyl)-N-methyl-4-(6-methyl-7-oxo-1H-pyrrolo[2,3-c]pyridin-4-yl)benzamide |
| 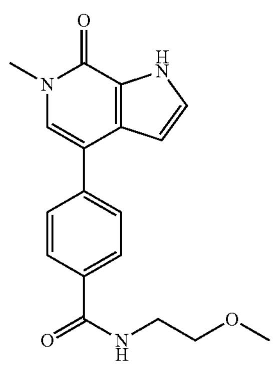 | N-(2-methoxyethyl)-4-(6-methyl-7-oxo-1H-pyrrolo[2,3-c]pyridin-4-yl)benzamide |
| 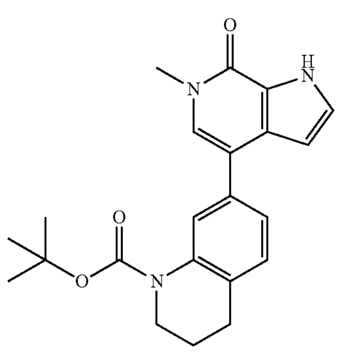 [SMILES: Cn1cc(-c2ccc3c(c2)N(C(=O)OC(C)(C)C)CCC3)c2cc[nH]c2c1=O] | tert-butyl 7-(6-methyl-7-oxo-1H-pyrrolo[2,3-c]pyridin-4-yl)-3,4-dihydro-2H-quinoline-1-carboxylate |

-continued

| Structure | Name |
|---|---|
| 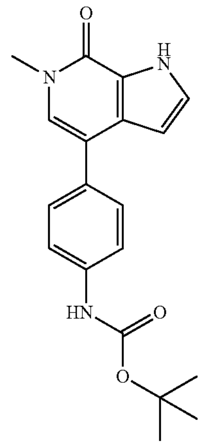 [SMILES: Cn1cc(-c2ccc(NC(=O)OC(C)(C)C)cc2)c2cc[nH]c2c1=O] | tert-butyl N-[4-(6-methyl-7-oxo-1H-pyrrolo[2,3-c]pyridin-4-yl)phenyl]carbamate |
| 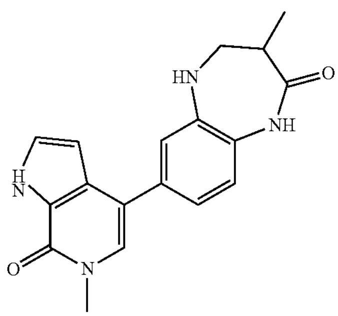 [SMILES: CC1CNc2cc(-c3cn(C)c(=O)c4[nH]ccc34)ccc2NC1=O] | 3-methyl-7-(6-methyl-7-oxo-1H-pyrrolo[2,3-c]pyridin-4-yl)-1,3,4,5-tetrahydro-1,5-benzodiazepin-2-one |
| 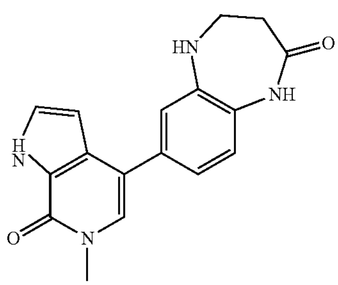 [SMILES: Cn1cc(-c2ccc3c(c2)NCCC(=O)N3)c2cc[nH]c2c1=O] | 7-(6-methyl-7-oxo-1H-pyrrolo[2,3-c]pyridin-4-yl)-1,3,4,5-tetrahydro-1,5-benzodiazepin-2-one |
| 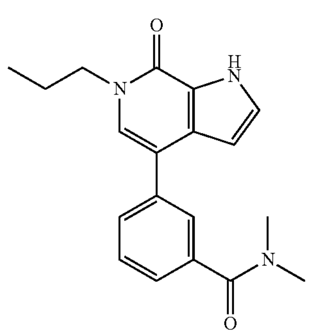 [SMILES: CCCn1cc(-c2cccc(C(=O)N(C)C)c2)c2cc[nH]c2c1=O] | N,N-dimethyl-3-(7-oxo-6-propyl-1H-pyrrolo[2,3-c]pyridin-4-yl)benzamide |
| 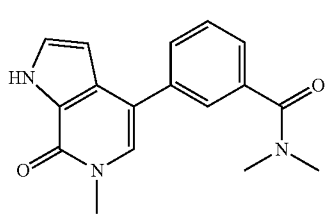 [SMILES: CN(C)C(=O)c1cccc(-c2cn(C)c(=O)c3[nH]ccc23)c1] | N,N-dimethyl-3-(6-methyl-7-oxo-1H-pyrrolo[2,3-c]pyridin-4-yl)benzamide |

| Structure | Name |
|---|---|
| 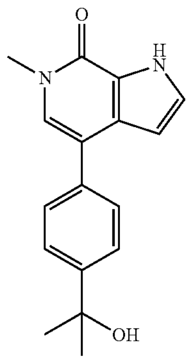 [SMILES: Cn1cc(-c2ccc(C(C)(C)O)cc2)c2cc[nH]c2c1=O] | 4-[4-(1-hydroxy-1-methyl-ethyl)phenyl]-6-methyl-1H-pyrrolo[2,3-c]pyridin-7-one |
| 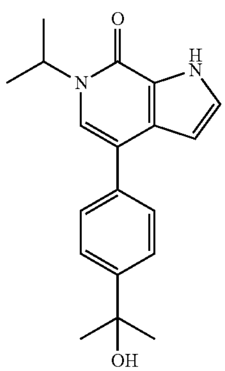 [SMILES: CC(C)n1cc(-c2ccc(C(C)(C)O)cc2)c2cc[nH]c2c1=O] | 4-[4-(1-hydroxy-1-methyl-ethyl)phenyl]-6-isopropyl-1H-pyrrolo[2,3-c]pyridin-7-one |
| 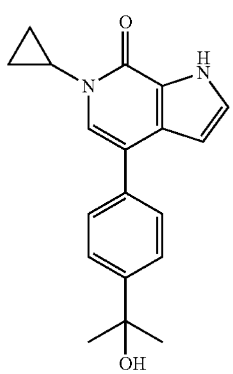 [SMILES: CC(C)(O)c1ccc(-c2cn(C3CC3)c(=O)c3[nH]ccc23)cc1] | 6-cyclopropyl-4-[4-(1-hydroxy-1-methyl-ethyl)phenyl]-1H-pyrrolo[2,3-c]pyridin-7-one |
| 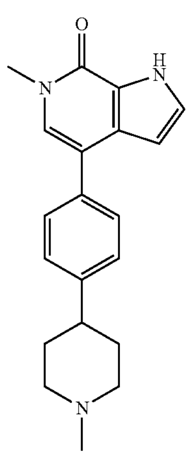 [SMILES: CN1CCC(c2ccc(-c3cn(C)c(=O)c4[nH]ccc34)cc2)CC1] | 6-methyl-4-[4-(1-methyl-4-piperidyl)phenyl]-1H-pyrrolo[2,3-c]pyridin-7-one |

| Structure | Name |
|---|---|
| 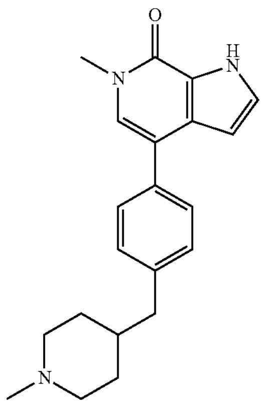 [SMILES: CN1CCC(Cc2ccc(-c3cn(C)c(=O)c4[nH]ccc34)cc2)CC1] | 6-methyl-4-[4-[(1-methyl-4-piperidyl)methyl]phenyl]-1H-pyrrolo[2,3-c]pyridin-7-one |
| 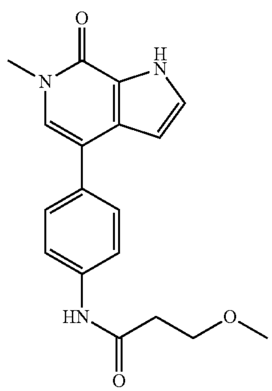 | 3-methoxy-N-[4-(6-methyl-7-oxo-1H-pyrrolo[2,3-c]pyridin-4-yl)phenyl]propanamide |
| 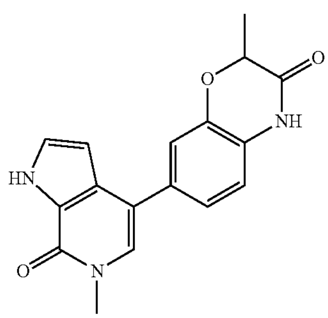 [SMILES: CC1Oc2cc(-c3cn(C)c(=O)c4[nH]ccc34)ccc2NC1=O] | 2-methyl-7-(6-methyl-7-oxo-1H-pyrrolo[2,3-c]pyridin-4-yl)-4H-1,4-benzoxazin-3-one |
| 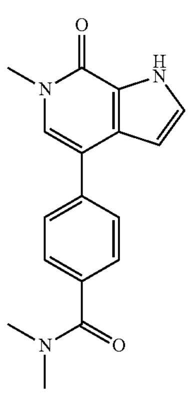 [SMILES: CN(C)C(=O)c1ccc(-c2cn(C)c(=O)c3[nH]ccc23)cc1] | N,N-dimethyl-4-(6-methyl-7-oxo-1H-pyrrolo[2,3-c]pyridin-4-yl)benzamide |

| Structure | Name |
|---|---|
| 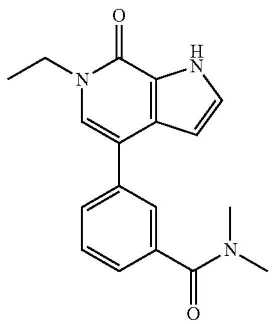 [SMILES: CCn1cc(-c2cccc(C(=O)N(C)C)c2)c2cc[nH]c2c1=O] | 3-(6-ethyl-7-oxo-1H-pyrrolo[2,3-c]pyridin-4-yl)-N,N-dimethyl-benzamide |
| 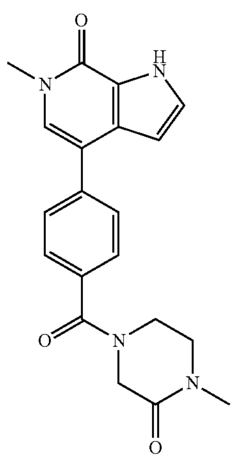 | 6-methyl-4-[4-(4-methyl-3-oxo-piperazine-1-carbonyl)phenyl]-1H-pyrrolo[2,3-c]pyridin-7-one |
| 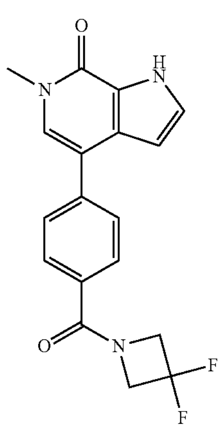 [SMILES: Cn1cc(-c2ccc(C(=O)N3CC(F)(F)C3)cc2)c2cc[nH]c2c1=O] | 4-[4-(3,3-difluoroazetidine-1-carbonyl)phenyl]-6-methyl-1H-pyrrolo[2,3-c]pyridin-7-one |

-continued

| Structure | Name |
|---|---|
| 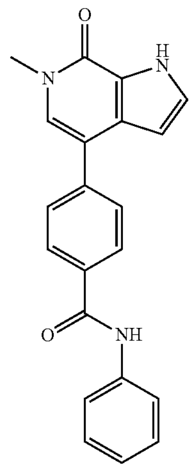 [SMILES: Cn1cc(-c2ccc(C(=O)Nc3ccccc3)cc2)c2cc[nH]c2c1=O] | 4-(6-methyl-7-oxo-1H-pyrrolo[2,3-c]pyridin-4-yl)-N-phenyl-benzamide |
| 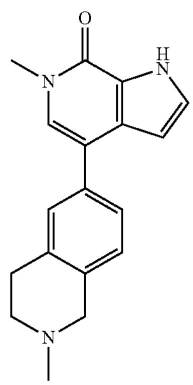 [SMILES: CN1CCc2cc(-c3cn(C)c(=O)c4[nH]ccc34)ccc2C1] | 6-methyl-4-(2-methyl-3,4-dihydro-1H-isoquinolin-6-yl)-1H-pyrrolo[2,3-c]pyridin-7-one |
| 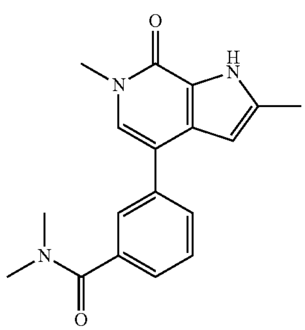 | 3-(2,6-dimethyl-7-oxo-1H-pyrrolo[2,3-c]pyridin-4-yl)-N,N-dimethyl-benzamide |
| 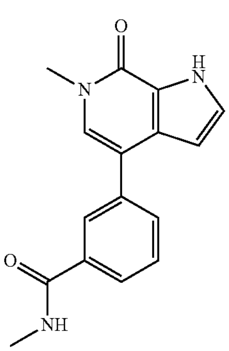 [SMILES: CNC(=O)c1cccc(-c2cn(C)c(=O)c3[nH]ccc23)c1] | N-methyl-3-(6-methyl-7-oxo-1H-pyrrolo[2,3-c]pyridin-4-yl)benzamide |

| Structure | Name |
|---|---|
| 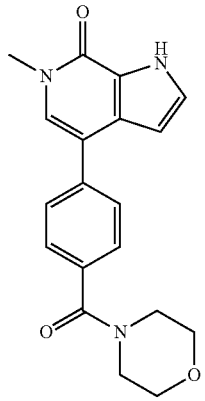 [SMILES: Cn1cc(-c2ccc(C(=O)N3CCOCC3)cc2)c2cc[nH]c2c1=O] | 6-methyl-4-[4-(morpholine-4-carbonyl)phenyl]-1H-pyrrolo[2,3-c]pyridin-7-one |
| 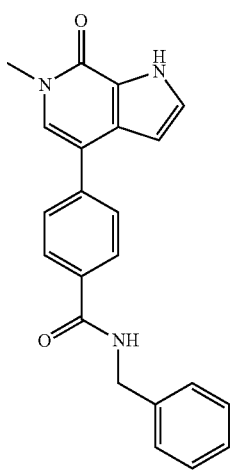 [SMILES: Cn1cc(-c2ccc(C(=O)NCc3ccccc3)cc2)c2cc[nH]c2c1=O] | N-benzyl-4-(6-methyl-7-oxo-1H-pyrrolo[2,3-c]pyridin-4-yl)benzamide |
| 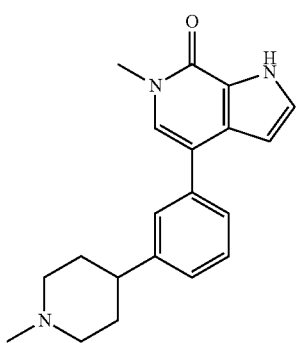 [SMILES: CN1CCC(c2cccc(-c3cn(C)c(=O)c4[nH]ccc34)c2)CC1] | 6-methyl-4-[3-(1-methyl-4-piperidyl)phenyl]-1H-pyrrolo[2,3-c]pyridin-7-one |

| Structure | Name |
|---|---|
| (structure) | 6-methyl-4-[3-[(1-methyl-4-piperidyl)methyl]phenyl]-1H-pyrrolo[2,3-c]pyridin-7-one |
| (structure) | 4-[3-(2-hydroxyethyl)-3-phenyl-indazn-5-yl]-6-methyl-1H-pyrrolo[2,3-c]pyridin-7-one | and salts thereof.

In certain embodiments for a compound of formula (I):

when $R^1$ is methyl; and $R^2$ is ethoxycarbonyl; then A is not 2-fluoro-5-(ethylsulfonyl)phenyl;

when $R^1$ is methyl; and $R^2$ is hydrogen; then A is not 2-(2,2-dimethylprop-1-yloxy)-5-aminophenyl;

when $R^1$ is methyl; and $R^2$ is hydrogen; then A is not 2-(2,2-dimethylprop-1-yloxy)-5-nitrophenyl;

when $R^1$ is methyl; and $R^2$ is hydrogen; then A is not 3-(ethylsulfonyl)-6-fluorophenyl;

when $R^1$ is methyl; and $R^2$ is hydrogen; then A is not 2-ethoxy-5-(methylsulfonyl) phenyl;

when $R^1$ is methyl; and $R^2$ is hydrogen; then A is not 4-bromo-2-methoxyphenyl;

when $R^1$ is methyl; and $R^2$ is hydrogen; then A is not 2-(2-tert-butoxy-1-methylethoxy)-5-methylsulfonylphenyl;

when $R^1$ is methyl; and $R^2$ is hydrogen; then A is not 2-iso-butoxy-5-methylsulfonylphenyl; and when $R^1$ is methyl; and $R^2$ is hydrogen; then A is not 2-(2-methylpropoxy)-5-ethylsulfonylaminophenyl.

In certain embodiments for a compound of formula (I):

when $R^1$ is methyl; and $R^2$ is hydrogen; then A is not 2-iso-propoxy-5-methylsulfonylphenyl.

In some embodiments, a compound of formula (I) excludes any compound of WO 2013/097052. In some embodiments, a compound of formula (I) excludes any compound of WO 2013/097601.

In certain embodiments the invention provides compound 1000 as described in Examples 48 and 50, and salts thereof. The invention also provides a method for evaluating a compound's ability to inhibit TAF1-BD2 by monitoring the engagement of compound 1000 with a TAF1-BD2 target as described in Example 50.

In certain embodiments the invention provides compound 1001 as described in Examples 49 and 50, and salts thereof.

The invention also provides a method for evaluating a compound's ability to inhibit CECR2 by monitoring the engagement of compound 1001 with a CECR2 target as described in Example 50.

One embodiment provides a composition comprising a compound disclosed herein or a pharmaceutically acceptable salt thereof, and a pharmaceutically acceptable adjuvant, carrier, or vehicle.

One embodiment provides a method for treating a bromodomain-mediated disorder in an animal comprising administering a disclosed herein or a pharmaceutically acceptable salt thereof to the animal.

One embodiment provides a compound disclosed herein or a pharmaceutically acceptable salt thereof for use in medical therapy.

One embodiment provides a compound disclosed herein or a pharmaceutically acceptable salt thereof for the prophylactic or therapeutic treatment of a bromodomain-mediated disorder.

One embodiment provides the use of a compound disclosed herein or a pharmaceutically acceptable salt thereof to prepare a medicament for treating a bromodomain-mediated disorder in an animal (e.g. a mammal such as a human).

One embodiment provides synthetic intermediates and synthetic processes disclosed herein that are useful for preparing a compounds disclosed herein or a salt thereof.

Uses, Formulation and Administration

Pharmaceutically Acceptable Compositions

Another aspect includes a pharmaceutical composition comprising a compound of formula (I) or a pharmaceutically acceptable salt thereof or a compound disclosed herein or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a bromodomain. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof or a compound disclosed herein or a pharmaceutically acceptable salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further or a compound disclosed herein or a pharmaceutically acceptable salt thereof comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof or a compound disclosed herein or a pharmaceutically acceptable salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of formula (I) or salt thereof or a compound disclosed herein or a salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I) or a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof or a compound disclosed herein or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I) or the compound disclosed herein.

Example dosage forms for topical or transdermal administration of a compound of formula (I) or a compound disclosed herein include ointments, pastes, creams, lotions, gels, powders, solutions, sprays, inhalants or patches. The compound of formula (I) or a salt thereof or the compound disclosed herein or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof or a compound disclosed herein or a salt thereof may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof or a compound disclosed herein or a salt thereof for the inhibition of a bromodomain (in vitro or in vivo).

Another embodiment includes a method for treating a bromodomain-mediated disorder in an animal comprising administering a compound of formula (I), or a pharmaceutically acceptable salt thereof or a compound disclosed herein or a pharmaceutically acceptable salt thereof to the animal. Bromodomain-mediated disorders include, but are not limited to those disorders described herein.

Another embodiment includes a method of increasing efficacy of a cancer treatment comprising a cytotoxic agent in an animal comprising administering to the animal an effective amount of a compound of formula (I) or a pharmaceutically acceptable salt thereof or a compound disclosed herein or a pharmaceutically acceptable salt thereof.

Another embodiment includes a method of delaying or preventing development of cancer resistance to a cytotoxic agent in an animal, comprising administering to the animal a compound of formula (I) or a pharmaceutically acceptable salt thereof or a compound disclosed herein or a pharmaceutically acceptable salt thereof.

Another embodiment includes a method of extending the duration of response to a cancer therapy in an animal, comprising administering to an animal undergoing the cancer therapy a compound of formula (I) or a pharmaceutically acceptable salt thereof or a compound disclosed herein or a pharmaceutically acceptable salt thereof, wherein the duration of response to the cancer therapy when the compound of formula (I) or the pharmaceutically acceptable salt or a compound disclosed herein or a pharmaceutically acceptable salt thereof is administered is extended over the duration of response to the cancer therapy in the absence of the administration of the compound of formula (I) or the pharmaceutically acceptable salt thereof or a compound disclosed herein or a pharmaceutically acceptable salt thereof.

Another embodiment includes a method of treating cancer in an individual comprising administering to the individual (a) a compound of formula (I) or a pharmaceutically acceptable salt thereof or a compound disclosed herein or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Bromodomain-Mediated Disorders

A "bromodomain-mediated disorder" is characterized by the participation of one or more bromodomains (e.g., BRD4) in the inception, manifestation of one or more symptoms or disease markers, severity, or progression of a disorder. Bromodomains include, but are not limited to ASH1L, ATAD2, ATAD2B, BAZ1A, BAZ1B, BAZ2A, BAZ2B, BPTF, BRD1, BRD2, BRD3, BRD4, BRD7, BRD8, BRD9, BRDT, BRPF1, BRPF3, BRWD1, BRWD3, CECR2, CREBBP (aka, CBP), EP300, GCN5L2, KIAA2026, MLL, MLL4, PBRM, PCAF, PHIP, SMARCA2, SMARCA4, SP100, SP110, SP140, SP140L, TAF1, TAF1L, TRIM24, TRIM28, TRIM33, TRIM66, ZMYND8, and ZMYND11.

Bromodomain-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

Bromodomain-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Bromodomain-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

Bromodomain inhibitors may also be used to provide male contraception.

Co-Administration of Compounds and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, Ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzutnab ozogamicin (MYLOTARG®, Wyeth). Additional humanized monoclonal antibodies with therapeutic potertial as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, toralizumab, toralizumab, tucotuzumab celmoleukin, tucusituzumab, umavizumab, urtoxazumab, ustekinumab, visilizumab, and the antiinterleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (Cl 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, Astra7eneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethypamino)-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and 051); dual-HER inhibitors such as EKB-569 (available from Wyeth) which preferentially binds EGFR but inhibits both HER2 and EGFR-overexpressing cells; lapatinib (GSK572016; available from Glaxo-Smith-Kline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVECC, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

For treating an inflammatory disease or an autoimmune disease, a compound of formula (I) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-IRI, siL-lRII, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopadatine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SClO-469, VX-702, AMG-548, VX-740, Roflumilast, IC-485, CDC-801, SIP1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-IRI, siL-IRII, siL-6R), and an antiinflammatory cytokine (e.g. IL-4, IL-10, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-lra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETA-SERON®; Chiron/Berlex); interferon-n3) (Interferon Sciences/Fujimoto), interferon-(Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or a pharmaceutically acceptable salt therof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt therof may also be co-administered with methotrexate, cyclosporine, FK506, rapamycin, mycophenolate mofetil, leflunomide, an SIPI agonist, an NSAID (e.g. ibuprofen), a corticosteroid (e.g. prednisolone), a phosphodiesterase inhibitor, a n adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-IRI, siL-IRII, or siL-6R), or an antiinflammatory cytokine (e.g. IL-4, IL-10, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/ chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/ castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); a n inhibitor of PDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-lra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with LIP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

A compound of formula (I) or a pharmaceutically acceptable salt thereof can also be co-administered with one or more agents used in the prevention or treatment of AIDS: an HIV reverse transcriptase inhibitor, a n HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders o r a chronic kidney disease, a compound of formula (I) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or salt thereof or a compound disclosed herein or a salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) or the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof or a compound disclosed herein or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonypethylamino)methyl)furan-2-yl)quinazolin-4-amine,di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof or a compound disclosed herein or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Generic Scheme A

Examples 1-7, 19-27, 44-48

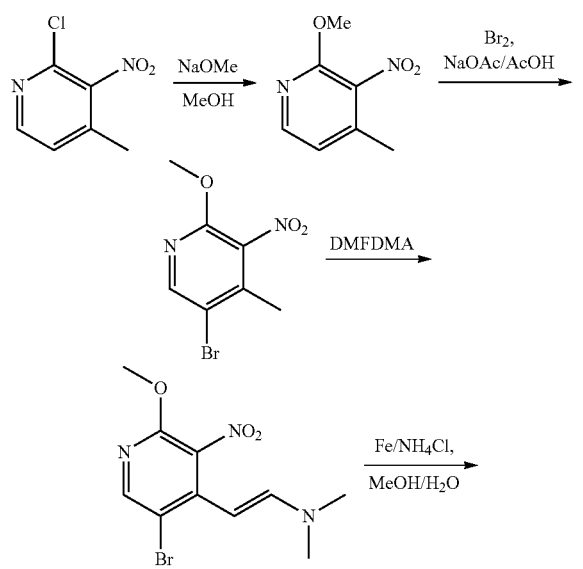

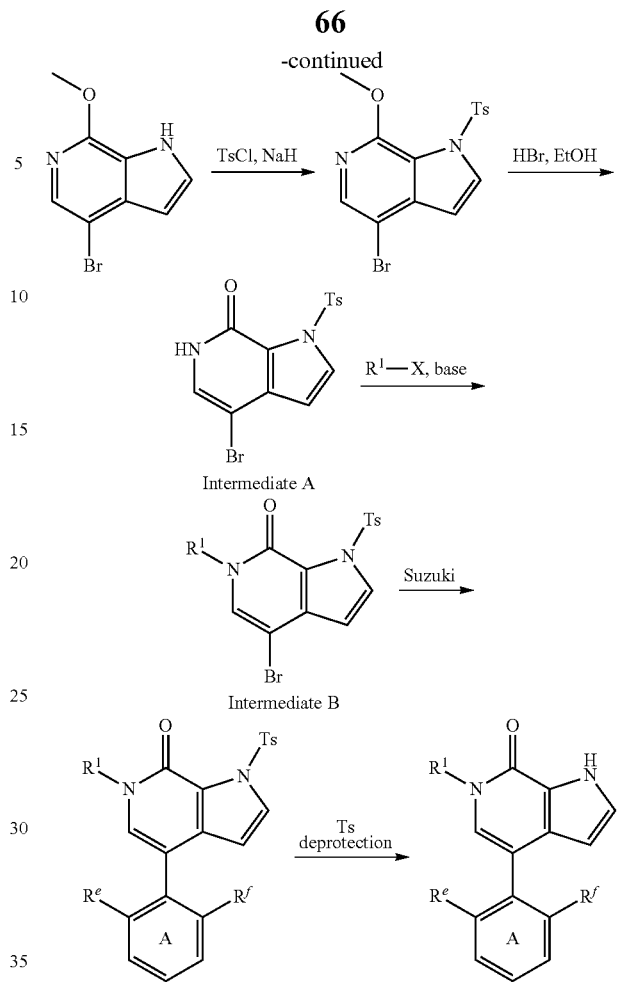

Representative compounds of formula (I) were prepared according to the scheme shown above. Intermediate B (prepared as described in the general synthesis of intermediates) was coupled with substituted aryl boronic acids under Pd-catalyzed conditions to form biaryl intermediates from which the tosyl group was removed under hydrolytic conditions to yield compounds of formula (I).

Generic Scheme B

Examples 9-17

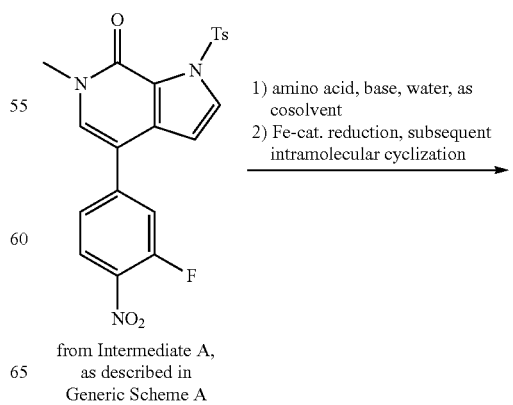

1) amino acid, base, water, as cosolvent
2) Fe-cat. reduction, subsequent intramolecular cyclization from Intermediate A, as described in Generic Scheme A -continued

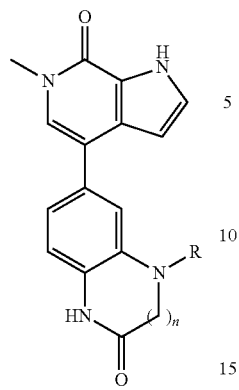

Representative compounds of formula (I) were prepared according to the scheme shown above.

4-(3-fluoro-4-nitrophenyl)-6-methyl-1-tosyl-1H-pyrrolo[2,3-c]pyridin-7(6H)-one (prepared according to Generic Scheme A, from Intermediate A and (3-fluoro-4-nitrophenyl)boronic acid) was treated with an amino acid or amino ester and a base in a solvent mixture that included water as a cosolvent at elevated temperature. The nitro groups of the crude reaction products were reduced with elemental iron in acetic acid at elevated temperature to reveal the corresponding aniline, which underwent intramolecular cyclization to yield compounds of formula (I).

Generic Scheme C

Examples 28-40

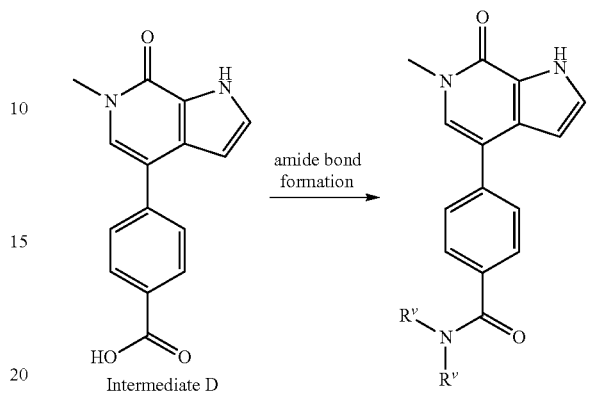

Intermediate D

Representative compounds of formula (I) were prepared according to the scheme shown above.

Intermediate D (prepared as described in the general synthesis of intermediates) was coupled with various amines to form compounds of formula (I).

Generic Scheme D

Examples 41-42

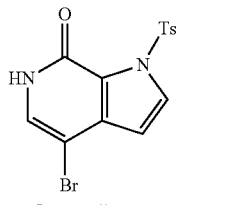

Intermediate A 1) alkylation
2) Ts deprotection

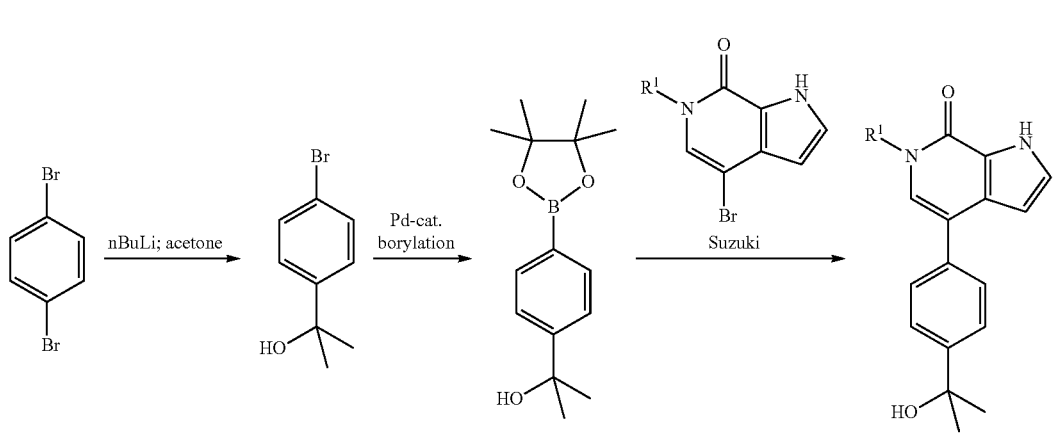

Representative compounds of formula (I) were prepared according to the scheme shown above. Intermediate A (prepared as described in the general synthesis of intermediates) was treated with an alkylating agent and a base in a solvent such as DMF or acetonitrile at elevated temperature to provide the corresponding N—R$^1$ substituted bromides. Those products were deprotected under hydrolytic conditions before being coupled with 2-(4-(4,4,5,5-tetramethyl-1,3,2-dioxaborolan-2-yl)phenyl)propan-2-ol (prepared from 1,4-dibromobenze treated with butyl lithium and quenched with acetone, followed by subsequent borylation) to form compounds of formula (I).

General Procedure for the Preparation of Intermediate A

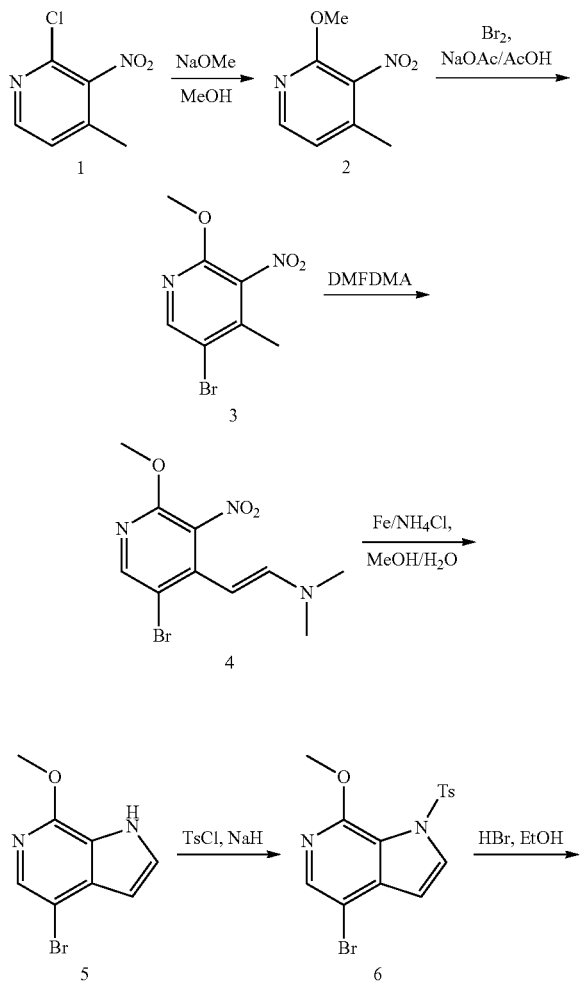

Step 1:

2-methoxy-4-methyl-3-nitropyridine

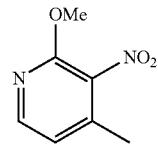

A solution of 2-chloro-4-methyl-3-nitropyridine (250 g, 1.45 mol) in methanol (1.0 L) was added dropwise (2 h) to a stirred and cooled (0° C.) solution of sodium methoxide (250 g, 4.63 mot) in methanol (850 mL). After addition, the mixture was heated to reflux for 23 h, at which time TLC indicated the reaction had gone to completion. The mixture was concentrated under reduced pressure to a volume of approximately 900 mL, and quenched by addition of water (1.5 L). The resulting solid was collected by filtration, washed with water and dried under reduced pressure to give the title compound (250 g, 100% yield) as a brown solid. $^1$H NMR (400 MHz, DMSO-d6): δ 8.22 (d, J=5.2 Hz, 1H), 7.10 (d, J=5.6 Hz, 1H), 3.92 (s, 3H), 2.26 (s, 3H).

Step 2:

5-bromo-2-methoxy-4-methyl-3-nitropyridine

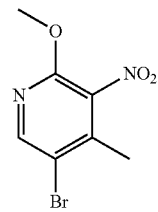

Sodium acetate (365 g, 5.37 mol) was added to a stirred solution of 2-methoxy-4-methyl-3-nitropyridine (250 g, 1.49 mol) in acetic acid (1.5 L) at ambient temperature and then Br$_2$ (639 g, 4.00 mol) was added dropwise (30 min). After addition, the mixture was heated at 80° C. for 12 h, at which time TLC indicated the reaction had gone to completion. The mixture was cooled (0° C.) and quenched by sequential addition of 10% aqueous (1.5 L) and saturated aqueous sodium sulfite (1.5 L). The resulting solid was collected by filtration washed with water, and dried under reduced pressure to give the title compound (302 g, 82.2% yield) as a light yellow solid. $^1$H NMR (400 MHz, DMSO-d6): δ 8.25 (s, 1H), 3.94 (s, 3H), 2.29 (s, 3H).

Step 3:

(E)-2-(5-bromo-2-methoxy-3-nitro-4-pyridyl)-N,N-dimethyl-ethenamine

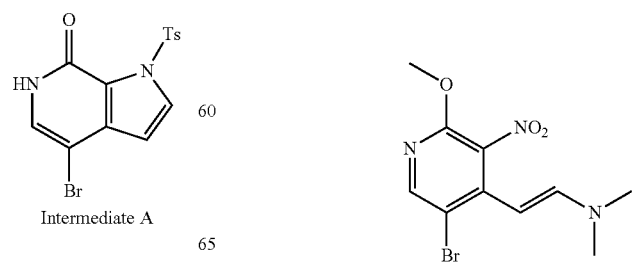

DMF-DMA (600 mL) was slowly added to a stirred and heated (80° C.) solution of 5-bromo-2-methoxy-4-methyl-3-nitropyridine (134 g, 0.54 mol) in DMF (1.1 L). After addition, the mixture was heated at 95° C. for 5 h, at which time TLC indicated the reaction had gone to completion. The mixture was cooled to room temperature and poured into ice-cold water (3 L). The resulting red solid was collected by filtration, washed with water, and dried under reduced pressure to give the title compound (167 g, 100% yield) as red solid. $^1$H NMR (400 MHz, DMSO-d6): δ 8.24 (s, 1H), 7.05 (d, J=13.6 Hz, 1H), 7.05 (d, J=13.6 Hz, 1H), 4.80 (d, J=13.2 Hz, 1H), 3.88 (s, 3H), 2.90 (s, 6H).

Step 4:

4-bromo-7-methoxy-1H-pyrrolo[2,3-c]pyridine

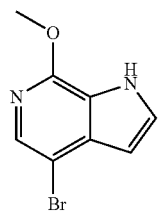

A mixture of 2-(5-bromo-2-methoxy-3-nitropyridin-4-yl)-N,N-dimethylethenamine (50.0 g, 165 mmol), Fe (50.0 g, 893 mmol) and NH$_4$Cl (50.0 g, 943 mmol) in methanol/water (1900/250 mL) was heated at reflux for 7 h, at which time LCMS indicated that the reaction had gone to completion. The mixture was filtered while hot and the cake was washed with methanol (3×200 mL). The combined filtrate was concentrated under reduced pressure, and the resulting residue was purified by silica gel chromatography (petroleum ether:ethyl acetate=5:1) to give the crude product. This crude material was triturated with acetonitrile to give the title compound (37.4 g, 99.5% yield) as a light brown solid. LCMS M/Z (M+H) 226.7, 228.7.

Step 5:

4-bromo-7-methoxy-1-(p-tolylsulfonyl)pyrrolo[2,3-c]pyridine

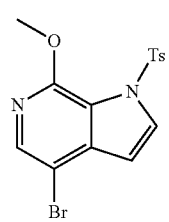 [SMILES: COc1ncc(Br)c2ccn(S(=O)(=O)c3ccc(C)cc3)c12]

A solution of 4-bromo-7-methoxy-1H-pyrrolo[2,3-c]pyridine (34.3 g, 0.15 mol) in tetrahydrofuran (700 mL) was added dropwise to a stirred and cooled (0° C.) solution of sodium hydride (60%, 19.2 g, 0.48 mol) in THF (700 mL). After addition, the mixture was stirred at room temperature for 1 h, and then cooled again to 0° C. Tosyl chloride (38.0 g, 0.20 mol) in THF (700 mL) was added dropwise and the resulting mixture was stirred at ambient temperature for 2 h. The reaction was quenched by addition of saturated aqueous ammonium chloride (1.0 L), and then extracted with ethyl acetate (3×600 mL). The combined organic extracts were dried over sodium sulfate and concentrated under reduced pressure. The residue was triturated with acetonitrile to give the title compound (51.2 g, 88.9% yield) as a brown solid. This crude material was used in the next step without further purification.

Step 6:

4-bromo-1-(p-tolylsulfonyl)-6H-pyrrolo[2,3-c]pyridin-7-one

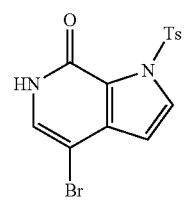 [SMILES: Cc1ccc(S(=O)(=O)n2ccc3c(Br)c[nH]c(=O)c32)cc1]

Hydrogen bromide (40% aqueous, 1.1 L) was added to a solution of 4-bromo-7-methoxy-1-(p-tolylsulfonyl)pyrrolo[2,3-c]pyridine (102.5 g, 0.27 mol) in ethanol (200 mL). After addition, the mixture was heated at 90° C. for 2 h, at which time TLC indicated that the reaction had gone to completion. The mixture was cooled to 0° C. and the resulting white solid was collected by filtration. This solid was washed with water and dried under vacuum to give the title compound (Intermediate A) (87.5 g, 88.6% yield) as a light brown solid. $^1$H NMR (400 MHz, DMSO-d6): δ 11.48 (s, 1H), 8.01 (d, J=3.6 Hz, 1H), 8.90 (d, J=8.0 Hz, 2H), 7.38 (d, J=8.0 Hz, 2H), 7.32 (s, 1H), 6.57 (d, J=3.2 Hz, 1H), 2.34 (s, 3H).

General Procedure for the Preparation of Intermediates B and C

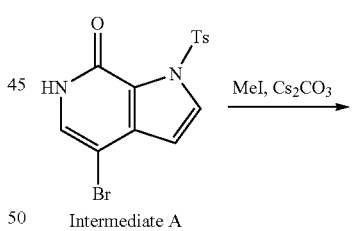

Intermediate A

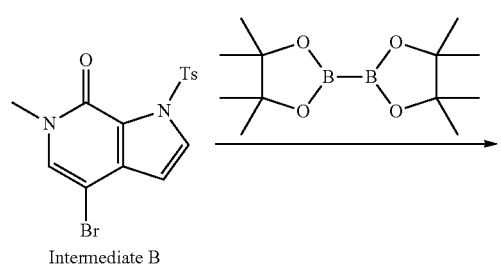

Intermediate B

Step 1:

4-bromo-6-methyl-1-(p-tolylsulfonyl)pyrrolo[2,3-c]pyridin-7-one

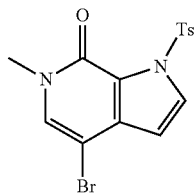 [SMILES: Cc1ccc(S(=O)(=O)n2ccc3c(Br)cn(C)c(=O)c32)cc1]

Methyl iodide (24.5 g, 172.8 mmol) was added dropwise to a stirred suspension of 4-bromo-1-tosyl-1H-pyrrolo[2,3-c]pyridin-7(6H)-one (Intermediate A) (16.7 g, 45.5 mmol) and cesium carbonate (17.8 g, 54.6 mmol) in 1,4-dioxane (250 mL). After addition, the reaction mixture was stirred at room temperature for 18 h, at which time LCMS indicated the reaction had gone to completion. The solvent was evaporated under reduced pressure, and the residue was diluted with water (200 mL). The mixture was extracted with ethyl acetate (3×200 mL). The combined organic extracts were dried over sodium sulfate and concentrated under reduced pressure. The residue was purified by silica gel chromatography (petroleum ether/ethyl acetate=3:1) to give the title compound (Intermediate B) (14.0 g, 81.4% yield) as a brown solid. $^1$H NMR (400 MHz, DMSO-d6): δ 8.03 (d, J=3.6 Hz, 1H), 7.92 (d, J=8.4 Hz, 2H), 7.78 (s, 1H), 7.39 (d, J=8.4 Hz, 2H), 6.57 (d, J=3.6 Hz, 1H), 3.35 (s, 3H), 2.35 (s, 3H).

Step 2:

6-methyl-1-(p-tolylsulfonyl)-4-(4,4,5,5-tetramethyl-1,3,2-dioxaborolan-2-yl)pyrrolo[2,3-c]pyridin-7-one

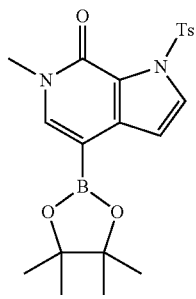 [SMILES: Cc1ccc(S(=O)(=O)n2ccc3c(B4OC(C)(C)C(C)(C)O4)cn(C)c(=O)c32)cc1]

Intermediate C

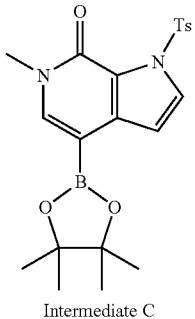

A mixture of 4-bromo-6-methyl-1-(p-tolylsulfonyl)pyrrolo[2,3-c]pyridin-7-one (3.0 g, 7.89 mmol) and 4,4,4',4',5,5,5',5'-octamethyl-2,2'-bi(1,3,2-dioxaborolane) (2.4 g, 9.47 mmol) in 1,4-dioxane (50 mL) was treated with potassium acetate (1.4 g, 14.27 mmol) and [1,1'-bis(diphenylphosphino)ferrocene]palladium(II) dichloride (300 mg, 0.39 mmol) at 100° C. under nitrogen atmosphere for 3 h. After cooled, the mixture was partitioned between water (50 mL) and dichloromethane (100 mL). The separated organic layer was dried over sodium sulfate and concentrated under reduced pressure. The crude product was purified by silica gel chromatography (petroleum ether:ethyl acetate=1:1) to give the title compound (Intermediate C, 1.3 g, 38.5% yield) as a yellow solid. LCMS M/Z (M+H) 429.1

General Procedure for the Preparation of Intermediate D

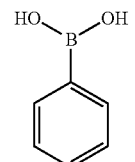

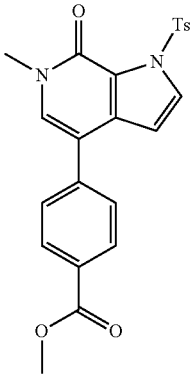 NaOH → 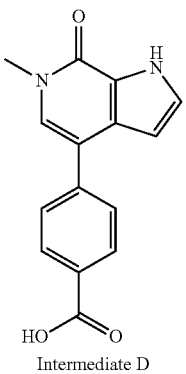

Intermediate B

Intermediate D

Step 1:

methyl 4-(6-methyl-7-oxo-1H-pyrrolo[2,3-c]pyridin-4-yl)benzoate

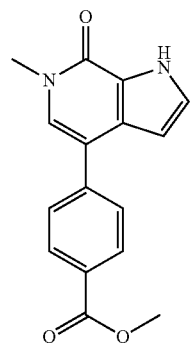 [SMILES: COC(=O)c1ccc(-c2cn(C)c(=O)c3[nH]ccc23)cc1]

A mixture of 4-bromo-6-methyl-1-(p-tolylsulfonyl)pyrrolo[2,3-c]pyridin-7-one (5.0 g, 13.0 mmol), (4-(methoxycarbonyl)phenyl)boronic acid (4.5 g, 26.0 mmol), potassium carbonate (5.5 g, 4.0 mmol) and palladium acetate (500 mg) in ethanol (100 mL) was heated at 110° C. for 10 h under nitrogen atmosphere. After cooling, the reaction mixture was diluted with water (50 mL) and then extracted with ethyl acetate (3×100 mL). The combined organic extracts were washed with brine (2×20 mL), dried over sodium sulfate and concentrated under reduced pressure. The residue was purified by silica gel chromatography (petroleum ether/ethyl acetate=3:1) to give the title compound (2.5 g, 64% yield) as a brown solid. LCMS M/Z (M+H) 282.9.

Step 2:

4-(6-methyl-7-oxo-1H-pyrrolo[2,3-c]pyridin-4-yl)benzoic acid

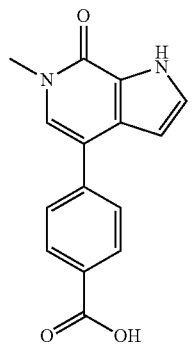 [SMILES: Cn1cc(-c2ccc(C(=O)O)cc2)c2cc[nH]c2c1=O]

Sodium hydroxide (1.2 g, 29.7 mmol) was added in portions to a stirred solution of methyl 4-(6-methyl-7-oxo-6,7-dihydro-1H-pyrrolo[2,3-c]pyridin-4-yl)benzoate (2.0 g, 6.8 mmol) in methanol/water (50 mL/10 mL). After addition, the resulting was heated at 80° C. for 2 h, at which time LCMS indicated the reaction had gone to completion. The mixture was concentrated under reduced pressure, and the residue was diluted with water (50 mL). The aqueous mixture was washed with ethyl acetate (3×50 mL), and then acidified to pH 3 using 1N hydrochloric acid. The resulting precipitate was collected by filtration and dried to give title compound (Intermediate D) (1.4 g, 77.8% yield) as a brown solid. $^1$H NMR (400 MHz, DMSO-d6): δ 12.21-12.18 (s, 1H), 8.02 (d, J=8.0 Hz, 2H), 7.73 (d, J=7.6 Hz, 2H), 7.53 (s, 1H), 7.38 (s, 1H), 6.52-6.48 (s, 1H), 3.60 (s, 3H).

General Procedure for the Preparation of Intermediate E

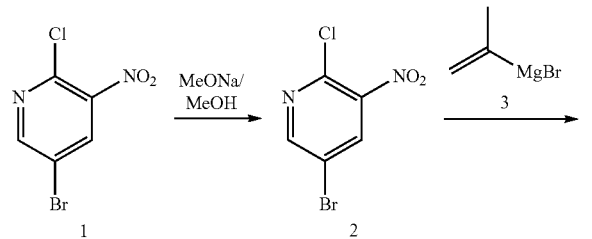

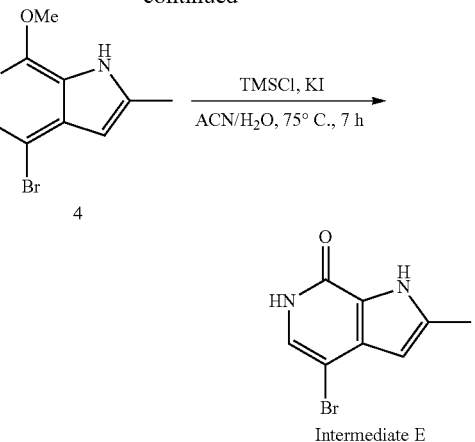

Step I:

5-bromo-2-methoxy-3-nitropyridine

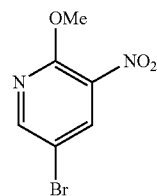 [SMILES: COc1ncc(Br)cc1[N+](=O)[O-]]

Sodium methoxide (17.2 g, 318.4 mmol) was added to a stirred solution of 5-bromo-2-chloro-3-nitropyridine (15.0 g, 64.2 mmol) in methanol (125 mL). After addition, the reaction mixture was heated at reflux for 2 h, at which time TLC indicated the reaction had gone to completion. The mixture was concentrated under reduced pressure, and the residue was diluted with water (200 mL). The resulting precipitate was collected by filtration, washed with water, and dried under reduced pressure to give the title compound (12.0 g, 81.5% yield) as a brown solid. $^1$H NMR (400 MHz, CDCl$_3$): δ 8.43 (d, J=2.4 Hz, 1H), 8.38 (d, J=2.0 Hz, 1H), 4.09 (s, 3H).

Step 2:

4-bromo-7-methoxy-2-methyl-1H-pyrrolo[2,3-c]pyridine

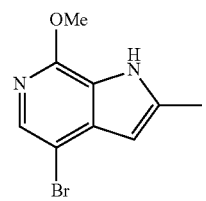

Isopropenyl magnesium bromide (0.5 M in THF, 105.0 mL, 55.0 mmol) was added dropwise to a stirred and cooled (−78° C.) solution of 5-bromo-2-methoxy-3-nitropyridine (4.0 g, 17.1 mmol) in THF (40 mL). After addition, the resulting mixture was allowed to warm to room temperature gradually and stirred for an additional 3 h. The reaction mixture was quenched by addition of 1 M aqueous ammonium chloride (150 mL), and then extracted with ethyl acetate (3×100 mL). The combined organic extracts were dried over sodium sulfate and concentrated under reduced pressure. The residue was purified by silica gel chromatography (petroleum ether:ethyl acetate=10:1) to give the title compound (1.65 g, 39.9% yield) as brown oil. LCMS M/Z (M+H) 240.1, 242.1.

Step 3:

4-bromo-2-methyl-1,6-dihydropyrrolo[2,3-c]pyridin-7-one

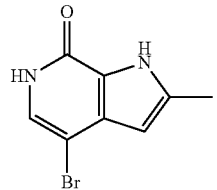

Hydrogen bromide (40% aqueous, 20 mL) was added to a solution of 4-bromo-7-methoxy-2-methyl-1H-pyrrolo[2,3-c]pyridine (1.65 g, 6.8 mmol) in ethanol (10 mL). After addition, the reaction mixture was heated at 90° C. for 15 h, at which time TLC indicated the reaction had gone to completion. The mixture was cooled to 0° C. and the resulting solid was collected by filtration. This solid was washed with water and dried to give title compound (Intermediate E) (0.9 g, 57.9% yield) as a brown solid. $^1$H NMR (400 MHz, DMSO-d6): δ 12.06 (s, 1H), 11.00 (s, 1H), 7.03 (s, 1H), 5.97 (s, 1H), 2.29 (s, 3H). LCMS M/Z (M+H) 226.8, 228.8

Example 1

6-methyl-4-phenyl-1H-pyrrolo[2,3-c]pyridin-7(6H)-one

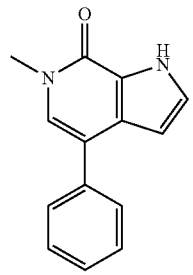 [SMILES: Cn1cc(-c2ccccc2)c2cc[nH]c2c1=O]

A vial was charged with 4-bromo-1-(p-tolylsulfonyl)-6H-pyrrolo[2,3-c]pyridin-7-one (Intermediate B, 50 mg, 0.13 mmol), phenyl boronic acid (32.0 mg, 0.26 mmol), palladium acetate (2.94 mg, 0.013 mmol), dicyclohexyl(2',6'-dimethoxybiphenyl-2-yl)phosphine (10.77 mg, 0.026 mmol), potassium carbonate (36.3 mg, 0.26 mmol), and 4:1 dioxane:water (3 mL). The mixture was stirred at 90° C. for 1 h and then filtered using ethyl acetate to rinse. The filtrate was concentrated under reduced pressure and then methanol (5 mL) and potassium hydroxide (36.8 mg, 0.66 mmol) were added. The reaction mixture was stirred at room temperature for 18 h. The mixture was diluted with water and submitted to reverse phase HPLC (acetonitrile/water/0.1% trifluoroacetic acid) to yield the title compound as a white amorphous solid (17%) following lyophilization from dioxane. $^1$H NMR (400 MHz, DMSO-d6) δ 12.02-12.24 (m, 1H), 7.59 (d, J=7.06 Hz, 2H), 7.46 (s, 3H), 7.37 (s, 1H), 7.34 (d, J=2.70 Hz, 2H), 6.48-6.60 (m, 1H), 6.41-6.46 (m, 1H), 3.58 (s, 3H). LCMS M/Z (M+H) 225.

The following compounds were prepared in a similar fashion to Example 1:

Examples 2-7

| Example | Name | NMR | m/z |
| --- | --- | --- | --- |
| 2 | 6-methyl-4-(2-oxoindolin-5-yl)-1H-pyrrolo[2,3-c]pyridin-7-one | $^1$H NMR (400 MHz, DMSO-d6) δ 12.09 (br. s., 1H), 10.43 (s, 1H), 7.42 (s, 1H), 7.40 (d, 1H), 7.33 (t, 1H), 7.27 (s, 1H), 6.89 (d, 1H), 6.42 (t, 1H), 3.56 (s, 3H), 3.53 (s, 2H). LCMS M/Z (M + H) 280. | 280 |
| 3 | N-(2-methoxyethyl)-4-(6-methyl-7-oxo-1H-pyrrolo[2,3-c]pyridin-4-yl)benzamide | $^1$H NMR (400 MHz, DMSO-d6) d 12.18 (br. s., 1H), 8.55 (t, 1H), 7.95 (d, 2H), 7.68 (d, 2H), 7.49 (s, 1H), 7.37 (t, 1H), 6.48 (t, 1H), 3.60 (s, 3H), 3.51-3.46 (m, 4H), 3.28 (s, 3H). | 326 |
| 4 | tert-butyl 6-(6-methyl-7-oxo-1H-pyrrolo[2,3-c]pyridin-4-yl)-3,4-dihydro-2H-quinoline-1-carboxylate | $^1$H NMR (400 MHz, DMSO-d6) Shift = 12.09 (br. s., 1H), 7.65 (d, J = 8.5 Hz, 1H), 7.35-7.29 (m, 6H), 6.43 (t, J = 2.4 Hz, 1H), 3.68-3.62 (m, 2H), 3.56 (s, 3H), 2.79 (t, J = 6.5 Hz, 2H), 1.90-1.81 (m, 2H), 1.47 (s, 9H). | ND |
| 5 | tert-butyl 7-(6-methyl-7-oxo-1H-pyrrolo[2,3-c]pyridin-4-yl)-3,4-dihydro-2H-quinoline-1-carboxylate | $^1$H NMR (400 MHz, DMSO-d6) d = 12.10 (br. s., 1H), 7.86 (s, 1H), 7.34 (t, J = 2.7 Hz, 1H), 7.27 (s, 1H), 7.21-7.14 (m, 2H), 6.51 (t, J = 2.3 Hz, 1H), 3.69-3.63 (m, 2H), 3.56 (s, 3H), 2.76 (t, J = 6.4 Hz, 2H), 1.90-1.81 (m, 2H), 1.46 (s, 9H) | ND |

| Example | Name | NMR | m/z |
|---|---|---|---|
| 6 | tert-butyl N-[4-(6-methyl-7-oxo-1H-pyrrolo[2,3-c]pyridin-4-yl)phenyl]carbamate | $^1$H NMR (400 MHz, DMSO-d6) 12.09 (br. s., 1H), 9.41 (s, 1H), 7.64-7.52 (m, 2H), 7.48-7.46 (m, 2H), 7.32 (t, 1H), 7.29 (s, 1H), 6.42 (t, 1H), 3.57 (s, 3H), 1.49 (s, 9H). | 340 |
| 7 | 3-methoxy-N-[4-(6-methyl-7-oxo-1H-pyrrolo[2,3-c]pyridin-4-yl)phenyl]propanamide | $^1$H NMR (400 MHz, DMSO-d6) d 12.10 (br. s., 1H), 10.02 (s, 1H), 7.68 (d, J = 8.52 Hz, 2H), 7.52 (d, J = 8.52 Hz, 2H), 7.22-7.38 (m, 2H), 6.40-6.44 (m, 1H), 3.63 (t, J = 6.13 Hz, 2H), 3.57 (s, 3H), 3.25 (s, 3H), 2.56 (t, J = 6.13 Hz, 2H). | 326 |

Example 8

4-(3-(2-hydroxyethyl)-3-phenyl-2,3-dihydro-1H-inden-5-yl)-6-methyl-1H-pyrrolo[2,3-c]pyridin-7(6H)-one

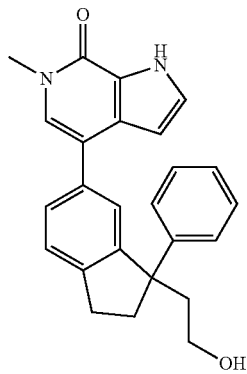 [SMILES: Cn1cc(-c2ccc3c(c2)C(CCO)(c2ccccc2)CC3)c2cc[nH]c2c1=O]

Step 1:

5-bromo-3-phenyl-1H-indene

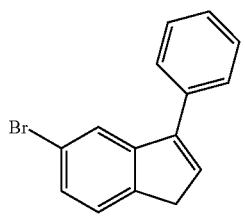 [SMILES: Brc1ccc2c(c1)C(c1ccccc1)=CC2]

To 6-bromo-2,3-dihydro-1H-inden-1-one (2.80 g, 13.27 mmol) in THF (10 mL) was added dropwise to a cooled (0° C.) solution of phenylmagnesium bromide (1 M in THF, 19.90 mL, 19.90 mmol), under argon atmosphere, in THF (26 mL). The reaction was allowed to stir overnight at room temperature and was the quenched with 1N HCl (200 mL). The mixture was extracted with ethyl acetate (3×100 mL). The combined organic extracts were washed with brine, dried with magnesium sulfate, and concentrated under reduced pressure to afford the tertiary alcohol, which was dissolved in THF (50 mL) and treated with 4-methylbenzenesulfonic acid (0.46 g, 2.65 mmol). This reaction was allowed to stir at room temperature for 6 h, and was then diluted with water (200 mL). The mixture was extracted with dichloromethane (3×100 mL) and the combined extracts were concentrated under reduced pressure. The residue was purified by silica gel chromatography (hexanes/ethyl acetate 20:1) to afford 5-bromo-3-phenyl-1H-indene (300 mg, 11%) as a colorless oil. This material was used in the next step without further purification. LCMS M/Z (M+H) 271.

Step 2:

6-bromo-1-phenyl-2,3-dihydro-1H-indene

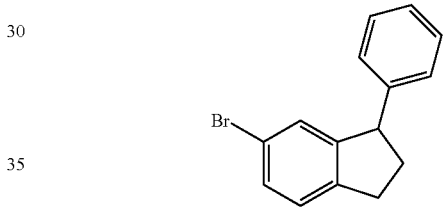

To 2,2,2-Trifluoroacetic acid (6.4 mL, 83 mmol) was added to a cooled (0° C.) solution of 5-bromo-3-phenyl-1H-indene (5.63 g, 20.7 mmol) and triethylsilane (9.95 mL, 62.3 mmol) in dichloromethane (50 mL) under a nitrogen atmosphere. The reaction was allowed to warm to room temperature and stirring was continued overnight. The reaction was carefully quenched with saturated aqueous sodium bicarbonate and then extracted with dichloromethane (3×100 mL). The combined organic extracts were dried with magnesium sulfate and concentrated under reduced pressure. The residue was purified by silica gel chromatography (hexanes/ethyl acetate 20:1) to afford 6-bromo-1-phenyl-2,3-dihydro-1H-indene (5.57 g, 98% yield. LCMS M/Z (M+H) 273.

Step 3:

2-(6-bromo-1-phenyl-2,3-dihydro-1H-inden-1-yl)ethanol

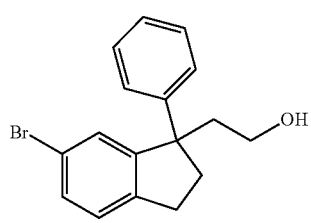 [SMILES: OCCC1(c2ccccc2)CCc2ccc(Br)cc21]

Dimethylsulfoxide (1.4 mL, 20.1 mmol) was added to a mixture of sodium hydride (60% in mineral oil, 0.24 g, 6.04 mmol) in THF (5 mL) under an argon atmosphere. The mixture was heated to 65° C. with stirring for 1.5 h and then cooled to 10° C. 6-Bromo-1-phenyl-2,3-dihydro-1H-indene (0.55 g, 2.01 mmol) in THF (0.5 mL) and then (2-bromoethoxy)(tert-butyl)dimethylsilane (0.86 mL, 4.03 mmol) were added and the reaction was stirred for 1 h at room temperature. The mixture was then quenched with water (25 mL) and extracted with methylene chloride (50 mL). The organic extract was dried with magnesium sulfate and concentrated under reduced pressure to afford (2-(6-bromo-1-phenyl-2,3-dihydro-1H-inden-1-yl)ethoxy)(tert-butyl)dimethylsilane as a colorless oil. This material was immediately dissolved in methanol (20 mL) and treated with 4N hydrogen chloride in dioxane (2 mL). This mixture was stirred for 1 h at room temperature and then concentrated under reduced pressure. The residue was purified via silica gel chromatography (hexanes/ethyl acetate 5:1) to afford 2-(6-bromo-1-phenyl-2,3-dihydro-1H-inden-1-yl)ethanol (518 mg, 73%). LCMS M/Z (M+Na) 341.

Step 4:

4-[3-(2-hydroxyethyl)-3-phenyl-indan-5-yl]-6-methyl-1-(p-tolylsulfonyl)pyrrolo[2,3-c]pyridin-7-one

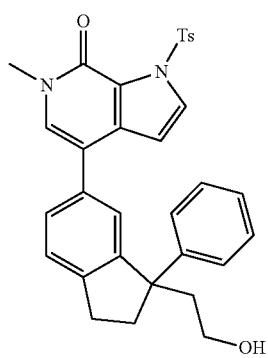 [SMILES: Cc1ccc(S(=O)(=O)n2ccc3c(-c4ccc5c(c4)C(CCO)(c4ccccc4)CC5)cn(C)c(=O)c32)cc1]

A mixture of 2-(6-bromo-1-phenyl-2,3-dihydro-1H-inden-1-yl)ethanol (476 mg, 1.5 mmol), potassium carbonate (518 mg, 3.75 mmol), 6-methyl-1-(p-tolylsulfonyl)-4-(4,4,5,5-tetramethyl-1,3,2-dioxaborolan-2-yl)pyrrolo[2,3-c]pyridin-7-one (Intermediate C, 642 mg, 1.5 mmol), and tetrakis(triphenylphosphine)palladium(0) (173 mg, 0.15 mmol) in 1,4-dioxane (7.5 mL) and water (1.5 mL) was purged and placed under a nitrogen atmosphere. The reaction was heated to 95° C. for 4 h and then cooled to room temperature. The mixture was loaded directly onto a silica gel column, eluting with ethyl acetate/hexanes (1:1) to afford title compound (487 mg, 54%). LCMS M/Z (M+H) 539.

Step 5:

4-(3-(2-hydroxyethyl)-3-phenyl-2,3-dihydro-1H-inden-5-yl)-6-methyl-1H-pyrrolo[2,3-c]pyridin-7(6H)-one

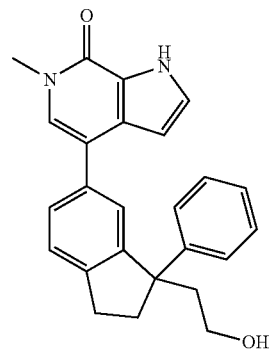 [SMILES: Cn1cc(-c2ccc3c(c2)C(CCO)(c2ccccc2)CC3)c2cc[nH]c2c1=O]

Potassium hydroxide (25 mg, 0.45 mmol) was added to a solution of 4-[3-(2-hydroxyethyl)-3-phenyl-indan-5-yl]-6-methyl-1-(p-tolylsulfonyl)pyrrolo[2,3-c]pyridin-7-one (240 mg, 0.45 mmol) in methanol (2 mL). The reaction was stirred at room temperature for 1 h and then pre-absorbed onto silica gel (5 g). This mixture was subjected to silica gel chromatography using methylene chloride/methanol (10:1) to afford 4-(3-(2-hydroxyethyl)-3-phenyl-2,3-dihydro-1H-inden-5-yl)-6-methyl-1H-pyrrolo[2,3-c]pyridin-7(6H)-one (107 mg, 56%). $^1$H NMR (400 MHz, DMSO-d6) δ 12.11 (br. s., 1H) 7.41-7.26 (m, 9H), 7.16 (t, 1H) 6.33 (t, 1H) 3.58 (s, 3H), 3.36-3.32 (m, 2H), 2.94-2.80 (m, 2H), 2.46-2.43 (m, 2H), 2.34-2.29 (m, 1H) 2.25-2.18 (m, 1H). LCMS M/Z (M+H) 385.

Example 9

8-(6-methyl-7-oxo-6,7-dihydro-1H-pyrrolo[2,3-c]pyridin-4-yl)-3,3a-dihydropyrrolo[1,2-a]quinoxaline-1,4(2H,5H)-dione Step 1

4-(3-fluoro-4-nitro-phenyl)-6-methyl-1H-pyrrolo[2,3-e]pyridin-7-one

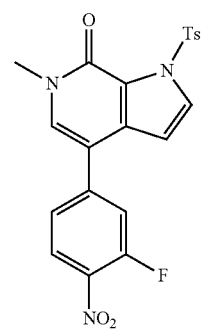 [SMILES: Cc1ccc(S(=O)(=O)n2ccc3c(-c4ccc([N+](=O)[O-])c(F)c4)cn(C)c(=O)c32)cc1]

Title compound was prepared from Intermediate A and (3-fluoro-4-nitrophenyl)boronic acid by the Suzuki method described in Example 1.

Step 2

4-(3-fluoro-4-nitro-phenyl)-6-methyl-1H-pyrrolo[2,3-e]pyridin-7-one

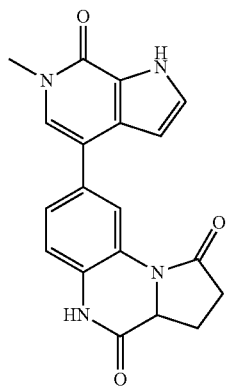 [SMILES: Cn1cc(-c2ccc3c(c2)N2C(=O)CCC2C(=O)N3)c2cc[nH]c2c1=O]

A mixture of 4-(3-fluoro-4-nitro-phenyl)-6-methyl-1-(p-tolylsulfonyl)pyrrolo[2,3-c]pyridin-7-one (0.059 g, 0.13 mmol), 2-aminopentanedioic acid (0.044 g, 0.27 mmol), and potassium carbonate (0.037 g, 0.27 mmol) in water (0.05 mL) and dimethylsulfoxide (6 mL) was stirred at room temperature for 2 h. The mixture was diluted with ethyl acetate and filtered over Celite using methanol to rinse. The combined filtrate was concentrated under reduced pressure to yield crude intermediate that was used directly in the next step.

The crude intermediate, 1-(5-(6-methyl-7-oxo-6,7-dihydro-1H-pyrrolo[2,3-c]pyridin-4-yl)-2-nitrophenyl)-5-oxopyrrolidine-2-carboxylic acid (0.053 g, 0.13 mmol) was dissolved in ethanol (5 mL) and acetic acid (0.15 ml, 2.68 mmol). Iron (0.060 g, 1.07 mmol) was added and the suspension was heated at 110° C. 1.5 h. After cooling, the mixture was diluted with ethyl acetate and the mixture was filtered through Celite using ethyl acetate to rinse. The combined filtrate was concentrated under reduced pressure and the residue was purified by preparative HPLC (acetonitrile/water/0.1% trifluoroacetic acid), yield title compound (3.7 mg, 6%) as a white solid. $^1$H NMR (400 MHz, DMSO-d6) δ 12.01-12.23 (m, 1H), 10.76 (s, 1H), 8.26 (d, J=1.87 Hz, 1H), 7.21-7.39 (m, 2H), 7.06 (d, J=8.10 Hz, 1H), 6.41-6.58 (m, 1H), 4.53 (s, 1H), 3.50-3.61 (m, 3H), 2.54-2.72 (m, 1H), 2.10-2.48 (m, 3H). LCMS M/Z (M+H) 349.

The following compounds were prepared in a similar fashion to Example 9:

Examples 10-17

| Example | Name | NMR | m/z |
|---|---|---|---|
| 10 | 3-methyl-6-(6-methyl-7-oxo-1H-pyrrolo[2,3-c]pyridin-4-yl)-3,4-dihydro-1H-quinoxalin-2-one | $^1$H NMR (400 MHz, DMSO-d6) d 11.98-12.13 (m, 1H), 10.10-10.30 (m, 1H), 7.27-7.34 (m, 1H), 7.21 (s, 1H), 6.89-6.98 (m, 1H), 6.68-6.85 (m, 2H), 6.35-6.45 (m, 1H), 6.02-6.14 (m, 1H), 3.75-3.84 (m, 1H), 3.55 (s, 3H), 1.26 (d, J = 6.65 Hz, 3H). | 309 |
| 11 | 3-methyl-7-(6-methyl-7-oxo-1H-pyrrolo[2,3-c]pyridin-4-yl)-1,3,4,5-tetrahydro-1,5-benzodiazepin-2-one | $^1$H NMR (400 MHz, DMSO-d6) d 12.08 (br. s., 1H), 9.47 (s, 1H), 7.32 (d, J = 2.91 Hz, 1H), 7.24 (s, 1H), 7.03 (d, J = 2.08 Hz, 1H), 6.93 (d, J = 8.10 Hz, 1H), 6.83 (dd, J = 2.08, 8.10 Hz, 1H), 6.44 (d, J = 2.91 Hz, 1H), 5.78 (d, J = 3.95 Hz, 1H), 3.55 (s, 3H), 3.42 (ddd, J = 3.64, 5.61, 11.53 Hz, 1H), 3.14-3.25 (m, 1H), 2.69 (ddd, J = 3.64, 6.70, 10.02 Hz, 1H), 1.01 (d, J = 6.86 Hz, 3H). | 323 |
| 12 | 7-(6-methyl-7-oxo-1H-pyrrolo[2,3-c]pyridin-4-yl)-1,3,4,5-tetrahydro-1,5-benzodiazepin-2-one | $^1$H NMR (400 MHz, DMSO-d6) d 12.08 (br. s., 1H), 9.47 (s, 1H), 7.32 (d, J = 2.70 Hz, 1H), 7.24 (s, 1H), 7.01 (d, J = 1.87 Hz, 1H), 6.94 (d, J = 8.10 Hz, 1H), 6.82 (dd, J = 1.87, 8.10 Hz, 1H), 6.44 (d, J = 2.70 Hz, 1H), 5.84 (t, J = 3.74 Hz, 1H), 3.55 (s, 3H), 3.41-3.49 (m, 2H), 2.50-2.58 (m, 2H). | 309 |
| 13 | 4-methyl-7-(6-methyl-7-oxo-1H-pyrrolo[2,3-c]pyridin-4-yl)-1,3,4,5-tetrahydro-1,5-benzodiazepin-2-one | $^1$H NMR (400 MHz, DMSO-d6) d 12.08 (br. s., 1H), 9.50 (s, 1H), 7.33 (t, J = 2.8 Hz, 1H), 7.25 (s, 1H), 7.12 (s, 1H), 6.91 (s, 2H), 6.46 (t, J = 2.3 Hz, 1H), 5.43 (d, J = 2.1 Hz, 1H), 3.89-3.80 (m, 1H), 3.55 (s, 3H), 2.46 (d, J = 3.5 Hz, 1H), 2.26 (dd, J = 7.5, 13.5 Hz, 1H), 1.20 (d, J = 6.4 Hz, 3H). | 323 |
| 14 | 3-isopropyl-6-(6-methyl-7-oxo-1H-pyrrolo[2,3-c]pyridin-4-yl)-1H-quinoxalin-2-one | $^1$H NMR (400 MHz, DMSO-d6) d 12.26-12.55 (m, 1H), 12.01-2.21 (m, 1H), 7.82-7.94 (m, 1H), 7.68-7.79 (m, 1H), 7.49 (s, 1H), 7.26-7.40 (m, 2H), 6.35-6.52 (m, 1H), 3.58 (s, 3H), 1.23 (d, J = 6.86 Hz, 6H). | 335 |
| 15 | 2-(6-methyl-7-oxo-1H-pyrrolo[2,3-c]pyridin-4-yl)-5,7,7a,8,9,10-hexahydropyrrolo[2,1-d][1,5]benzodiazepin-6-one | $^1$H NMR (400 MHz, DMSO-d6) d 11.95-12.19 (m, 1H), 9.52 (s, 2H), 7.22-7.37 (m, 1H), 6.98 (d, J = 7.69 Hz, 1H), 6.85 (m, 2H), 6.45 (br. s., 1H), 3.69-3.88 (m, 1H), 3.55 (s, 3H), 3.42 (m, 2H), 2.54-2.71 (m, 2H), 2.06-2.22 (m, 2H), 1.94-2.02 (m, 2H), 1.90 (d, J = 1.25 Hz, 2H), 1.50-1.69 (m, 2H). LCMS M/Z (M + H) 349. | 349 |

| Example | Name | NMR | m/z |
|---|---|---|---|
| 16 | 2-methyl-7-(6-methyl-7-oxo-1H-pyrrolo[2,3-c]pyridin-4-yl)-4H-1,4-benzoxazin-3-one | ¹H NMR (400 MHz, DMSO-d6) d 11.99-12.26 (m, 1H), 10.71 (s, 1H), 7.29-7.39 (m, 2H), 7.16-7.23 (m, 1H), 7.14 (d, J = 1.87 Hz, 1H), 6.96 (d, J = 8.10 Hz, 1H), 6.35-6.45 (m, 1H), 4.69 (d, J = 6.65 Hz, 1H), 3.55 (s, 3H), 1.44 (d, J = 6.86 Hz, 3H). | 310 |
| 17 | 7-(6-methyl-7-oxo-1H-pyrrolo[2,3-c]pyridin-4-yl)-4-(2-thienyl)-1,3,4,5-tetrahydro-1,5-benzodiazepin-2-one | ¹H NMR (400 MHz, DMSO-d6) d 12.29-11.96 (m, 1H), 9.77-9.47 (m, 1H), 7.41-7.37 (m, 1H), 7.36-7.31 (m, 1H), 7.28 (s, 1H), 7.25-7.21 (m, 1H), 7.08-7.05 (m, 1H), 7.04-6.92 (m, 3H), 6.53-6.46 (m, 1H), 6.07-5.98 (m, 1H), 5.31-5.19 (m, 1H), 3.56 (s, 3H), 2.86-2.58 (m, 2H). | 391 |

Example 18

N,N-dimethyl-4-(6-methyl-7-oxo-1H-pyrrolo[2,3-c]pyridin-4-yl)benzamide

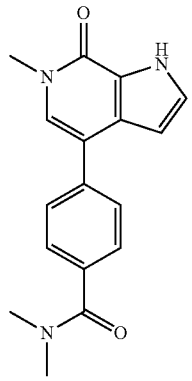 [SMILES: CN(C)C(=O)c1ccc(-c2cn(C)c(=O)c3[nH]ccc23)cc1]

Step 1

N,N-dimethyl-4-[6-methyl-7-oxo-1-(p-tolylsulfonyl)pyrrolo[2,3-e]pyridin-4-yl]benzamide

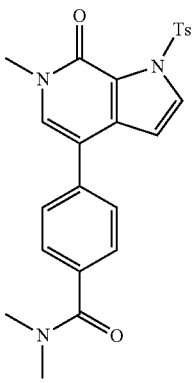 [SMILES: Cc1ccc(S(=O)(=O)n2ccc3c(-c4ccc(C(=O)N(C)C)cc4)cn(C)c(=O)c32)cc1]

To a mixture of 4-bromo-6-methyl-1-(p-tolylsulfonyl)pyrrolo[2,3-c]pyridin-7-one (Intermediate B, 30 mg, 0.08 mmol), [4-(dimethylcarbamoyl)phenyl]boronic acid (20 mg, 0.1 mmol) in acetonitrile (0.5 mL) and 1M potassium carbonate in water (0.5 mL) was added [1,1'-bis(diphenylphosphino)ferrocene]palladium(II) dichloride (6 mg, 0.008 mmol). The reaction mixture was stirred under microwave irradiation at 120° C. for 10 minutes. The reaction mixture was diluted with water (5 mL) and then extracted with ethyl acetate (3×5 mL). The combined organic extracts were dried over sodium sulfate and concentrated under reduced pressure to yield the title compound (60 mg, 100% yield). This crude material was used in the next step without further purification. LCMS M/Z (M+H) 450.4.

Step 2

N,N-dimethyl-4-(6-methyl-7-oxo-1H-pyrrolo[2,3-c]pyridin-4-yl)benzamide

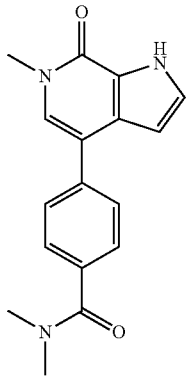 [SMILES: CN(C)C(=O)c1ccc(-c2cn(C)c(=O)c3[nH]ccc23)cc1]

A mixture of N,N-dimethyl-4-[6-methyl-7-oxo-1-(p-tolylsulfonyl)pyrrolo[2,3-c]pyridin-4-yl]benzamide (60 mg, 0.1 mmol) in methanol (1 mL) and 10 M potassium hydroxide in water (0.1 mL) was stirred at 45° C. for 2 h. The mixture was concentrated under reduced pressure and the residue was dissolved in water (10 mL). The mixture was extracted with ethyl acetate (3×10 mL). The combined organic extracts were dried over sodium sulfate and concentrated under reduced pressure. The residue was purified by preparative HPLC (5-50% ACN/0.1% NH4OH in H2O) to give the title compound (11 mg, 30% yield) as a white solid. ¹H NMR (400 MHz, DMSO-d6) δ 12.15 (s, 1H), 7.68-7.62 (m, 2H), 7.52-7.48 (m, 2H), 7.45 (s, 1H), 7.36 (t, J=2.8 Hz, 1H), 6.48 (q, J=2.0 Hz, 1H), 3.59 (s, 3H), 2.99 (s, 6H). LCMS M/Z (M+H) 296.2.

Example 19

N,N-dimethyl-3-(7-oxo-6-propyl-1H-pyrrolo[2,3-c]pyridin-4-yl)benzamide

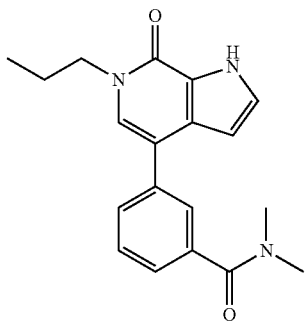 [SMILES: CCCn1cc(-c2cccc(C(=O)N(C)C)c2)c2cc[nH]c2c1=O]

Step 1

4-bromo-6-propyl-1-(p-tolylsulfonyl)pyrrolo[2,3-c]pyridin-7-one

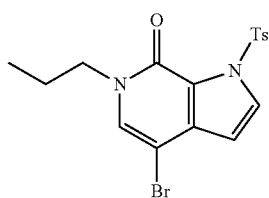 [SMILES: CCCn1cc(Br)c2ccn(S(=O)(=O)c3ccc(C)cc3)c2c1=O]

4-bromo-6-propyl-1-(p-tolylsulfonyl)pyrrolo[2,3-c]pyridin-7-one was prepared in a similar fashion as Intermediate B (210 mg, 100%). LCMS M/Z (M+H) 409/411.

Step 2

N,N-dimethyl-3-[7-oxo-6-propyl-1-(p-tolylsulfonyl)pyrrolo[2,3-c]pyridin-4-yl]benzamide

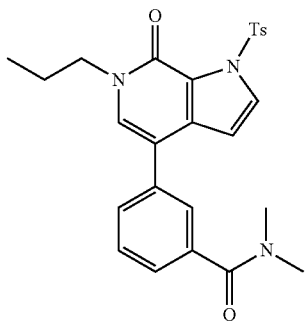 [SMILES: CCCn1cc(-c2cccc(C(=O)N(C)C)c2)c2ccn(S(=O)(=O)c3ccc(C)cc3)c2c1=O]

To a mixture of 4-bromo-6-propyl-1-(p-tolylsulfonyl)pyrrolo[2,3-c]pyridin-7-one (210 mg, 0.51 mmol) and [3-(dimethylcarbamoyl)phenyl]boronic acid (110 mg, 0.56 mmol) in acetonitrile (2 mL) and 1 M potassium carbonate in water (2 mL) was added [1,1'-bis(diphenylphosphino)ferrocene]palladium(II) dichloride (38 mg, 0.051 mmol). The reaction mixture was subjected to microwave irradiation at 100° C. for 10 minutes. The mixture was filtered through a pad of Celite, using ethyl acetate (30 mL) to rinse. The filtrate was washed with brine (10 mL), dried over sodium sulfate and concentrated under reduced pressure to yield the title compound (240 mg, 98% yield) as a yellow solid. This crude material was used in the next step without further purification. LCMS MJZ (M+H) 478.

Step 3

N,N-dimethyl-3-(7-oxo-6-propyl-1H-pyrrolo[2,3-c]pyridin-4-yl)benzamide

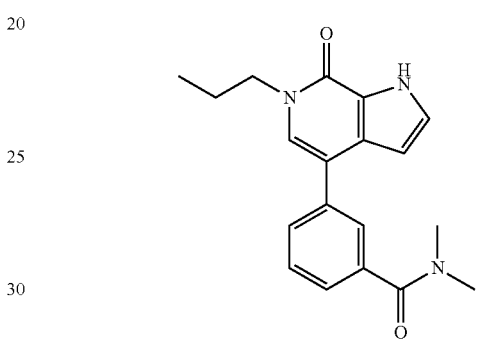

A mixture of N,N-dimethyl-3-[7-oxo-6-propyl-1-(p-tolylsulfonyl)pyrrolo[2,3-e]pyridin-4-yl]benzamide (240 mg, 0.50 mmol) in methanol (2 mL) and 10 M potassium hydroxide in water (0.4 mL) was stirred at 50° C. for 1 h. After cooling, the reaction mixture was concentrated under reduced pressure. The residue was dissolved in water (5 mL) and extracted with ethyl acetate (3×10 mL). The combined organic extracts were dried over sodium sulfate and concentrated under reduced pressure. The residue was purified by preparative HPLC (25-35% ACN/0.1% NH4OH in H2O) to give the title compound (17.3 mg, 10% yield) as a white solid. 1H NMR (400 MHz, DMSO-d6) δ 7.68 (dt, J=7.9, 1.4 Hz, 1H), 7.60-7.48 (m, 2H), 7.42 (s, 1H), 7.40-7.29 (m, 2H), 6.43 (t, J=2.3 Hz, 1H), 4.00 (dd, J=8.0, 6.6 Hz, 2H), 2.99 (d, J=13.3 Hz, 6H), 1.72 (m, J=7.3 Hz, 2H), 0.91 (m, J=7.4 Hz, 3H). LCMS M/Z (M+H) 324.

The following compounds were prepared in a similar fashion to Example 19:

Examples 20-25

| Example | IUPAC Compound Name | NMR | m/z |
|---|---|---|---|
| 20 | 3-(6-ethyl-7-oxo-1H-pyrrolo[2,3-c]pyridin-4-yl)-N,N-dimethyl-benzamide | $^1$H NMR (400 MHz, DMSO-d6) δ 12.11 (s, 1H), 7.68 (dt, J = 7.8, 1.5 Hz, 1H), 7.58 (t, J = 1.7 Hz, 1H), 7.52 (t, J = 7.7 Hz, 1H), 7.42 (s, 1H), 7.35 (dd, J = 8.3, 1.9 Hz, 2H), | 310.2 |

| Example | IUPAC Compound Name | NMR | m/z |
|---|---|---|---|
| | | 6.42 (d, J = 2.8 Hz, 1H), 4.08 (q, J = 7.1 Hz, 2H), 2.99 (d, J = 7.7 Hz, 6H), 1.29 (t, J = 7.1 Hz, 3H). | |
| 21 | 3-(6-methyl-7-oxo-1H-pyrrolo[2,3-c]pyridin-4-yl)benzamide | 1H NMR (400 MHz, DMSO-d6) δ 12.14 (s, 1H), 8.10-8.04 (m, 1H), 8.04-7.99 (m, 1H), 7.86-7.78 (m, 1H), 7.78-7.70 (m, 1H), 7.62-7.48 (m, 1H), 7.44 (s, 1H), 7.36 (d, J = 2.8 Hz, 1H), 6.46 (d, J = 2.8 Hz, 1H), 3.60 (s, 3H), 3.28 (s, 1H). | 268 |
| 22 | N,N-dimethyl-3-(6-methyl-7-oxo-1H-pyrrolo[2,3-c]pyridin-4-yl)benzamide | 1H NMR (400 MHz, DMSO-d6) δ 12.15 (s, 1H), 7.71-7.63 (m, 1H), 7.60-7.48 (m, 2H), 7.44 (s, 1H), 7.39-7.31 (m, 2H), 6.43 (d, J = 2.8 Hz, 1H), 3.59 (s, 3H), 3.03-2.95 (m, 6H). | 296 |
| 23 | 3-(6-methyl-7-oxo-1H-pyrrolo[2,3-c]pyridin-4-yl)benzonitrile | 1H NMR (400 MHz, DMSO-d6) δ 12.19 (s, 1H), 8.04-7.92 (m, 2H), 7.83-7.75 (m, 1H), 7.67 (t, J = 7.8 Hz, 1H), 7.55 (s, 1H), 7.41-7.35 (m, 1H), 6.49 (d, J = 2.7 Hz, 1H), 3.59 (s, 3H). | 250 |
| 24 | N-methyl-3-(6-methyl-7-oxo-1H-pyrrolo[2,3-c]pyridin-4-yl)benzamide | 1H NMR (400 MHz, DMSO-d6) δ 12.14 (s, 1H), 8.46 (q, J = 4.3 Hz, 1H), 8.02 (t, J = 1.7 Hz, 1H), 7.75 (ddt, J = 18.2, 7.8, 1.3 Hz, 2H), 7.54 (t, J = 7.7 Hz, 1H), 7.44 (s, 1H), 7.36 (t, J = 2.6 Hz, 1H), 6.53-6.43 (m, 1H), 3.60 (s, 3H), 2.81 (d, J = 4.5 Hz, 3H). | 282 |
| 25 | 4-[4-(hydroxymethyl)phenyl]-6-methyl-1H-pyrrolo[2,3-c]pyridin-7-one | 1H NMR (400 MHz, DMSO-d6) δ 12.09 (s, 1H), 7.65-7.51 (m, 2H), 7.43-7.31 (m, 4H), 6.43 (d, J = 2.8 Hz, 1H), 5.18 (s, 1H), 4.54 (d, J = 3.2 Hz, 2H), 3.58 (s, 3H). | 255 |

Example 26

6-methyl-4-(4-(4-methyl-3-oxopiperazine-1-carbonyl)phenyl)-1H-pyrrolo[2,3-c]pyridin-7(6H)-one

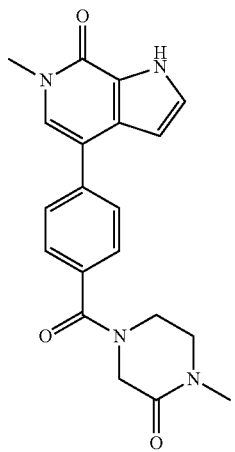

HATU (184 mg, 0.48 mmol) was added to a stirred mixture of 4-(6-methyl-7-oxo-6,7-dihydro-1H-pyrrolo[2,3-c]pyridin-4-yl)benzoic acid (Intermediate D) (100 mg, 0.37 mmol), 1-methylpiperazin-2-one (63 mg, 0.56 mmol), and diisopropylethylamine (168 mg, 1.30 mmol) in DMF (5 mL). The reaction mixture was stirred at room temperature for 8 h, at which time LCMS indicated that the reaction had gone to completion. The reaction mixture was partitioned between ethyl acetate (20 mL) and water (15 mL). The separated organic solution was washed with brine (2×10 mL), dried over sodium sulfate and concentrated under reduced pressure. The residue was purified by preparative HPLC, acetonitrile:water (10 nM ammonia bicarbonate) 35%-65%, to afford the title compound (47.9 mg, 15.8% yield) as a white solid. $^1$H NMR (400 MHz, DMSO-d6): δ 12.14 (s, 1H), 7.66 (d, J=8.4 Hz, 2H), 7.52 (d, J=8.4 Hz, 2H), 7.45 (s, 1H), 7.35 (s, 1H), 6.47 (d, J=2.0 Hz, 1H), 4.12-4.09 (m, 4H), 3.56-3.50 (m, 2H), 3.47 (s, 3H), 2.85 (s, 3H). LCMS M/Z (M+H) 365.1.

The following compounds were prepared in a similar fashion to Example 26:

Examples 27-38

| Example | IUPAC Compound Name | NMR | m/z |
|---|---|---|---|
| 27 | 4-[4-(3-fluoroazetidine-1-carbonyl)phenyl]-6-methyl-1H-pyrrolo[2,3-c]pyridin-7-one | 1H NMR (400 MHz, DMSO-d6): δ 12.20 (s, 1H), 7.76-7.67 (m, 4H), 7.50 (s, 1H), 7.38 (d, J = 2.4 Hz, 1H), 6.48 (s, 1H), 5.56-5.35 (m, 1H), 4.70-4.37 (m, 3H), 4.12-4.09 (m, 1H), 3.60 (s, 3H). | 326 |

| Example | IUPAC Compound Name | NMR | m/z |
|---|---|---|---|
| 28 | 4-[4-(3,3-difluoroazetidine-1-carbonyl)phenyl]-6-methyl-1H-pyrrolo[2,3-c]pyridin-7-one | 1H NMR (400 MHz, DMSO-d6): δ 7.79 (d, J = 8.0 Hz, 2H), 7.71 (d, J = 8.4 Hz, 2H), 7.52 (s, 1H), 7.38 (d, J = 2.8 Hz, 1H), 6.48 (d, J = 2.4 Hz, 1H), 4.90-4.70 (m, 2H), 4.60-4.40 (m, 2H), 3.60 (s, 3H). | 344 |
| 29 | 6-methyl-4-[4-(pyrrolidine-1-carbonyl)phenyl]-1H-pyrrolo[2,3-c]pyridin-7-one | 1H NMR (400 MHz, DMSO-d6): δ 12.15 (s, 1H), 7.64-7.58 (m, 4H), 7.44 (s, 1H), 7.34 (s, 1H), 6.46 (s, 1H), 3.57 (s, 3H), 3.46-3.44 (m, 4H), 1.86-1.81 (m, 4H). | 322 |
| 30 | 6-methyl-4-[4-(morpholine-4-carbonyl)phenyl]-1H-pyrrolo[2,3-c]pyridin-7-one | 1H NMR (400 MHz, DMSO-d6): δ 12.15 (s, 1H), 7.65 (d, J = 8.4 Hz, 2 H), 7.48 (d, J = 8.0 Hz, 2H), 7.44 (s, 1H), 7.34 (s, 1H), 6.46 (s, 1H), 3.62-3.45 (m, 8H). | 338 |
| 31 | 6-methyl-4-[4-(4-methylpiperidine-1-carbonyl)phenyl]-1H-pyrrolo[2,3-c]pyridin-7-one | 1H NMR (400 MHz, DMSO-d6): δ 12.14 (s, 1H), 7.63 (d, J = 8.0 Hz, 2H), 7.45-7.41 (m, 3H), 7.35-7.33 (m, 1H), 6.47-6.45 (m, 1H), 3.56 (s, 3H), 2.92-2.87 (m, 2H), 2.85-2.62 (m, 2H), 1.70-1.52 (m, 2H), 1.0-1.17 (m, 2H), 0.91 (d, J = 6.4 Hz, 3H). | 350 |
| 32 | 4-[4-(4-acetylpiperazine-1-carbonyl)phenyl]-6-methyl-1H-pyrrolo[2,3-c]pyridin-7-one | 1H NMR (400 MHz, DMSO-d6): δ 12.15 (s, 1H), 7.66 (d, J = 8.4 Hz, 2H), 7.49 (d, J = 8.0 Hz, 2H), 7.45 (s, 1H), 7.35 (t, J = 2.8 Hz, 1H), 6.47 (d, J = 2.4 Hz, 1H), 3.57 (s, 3H), 3.55-3.45 (m, 4H), 2.67-2.61 (m, 2H), 2.34-2.25 (m, 2H), 2.01 (s, 3H). | 379 |
| 33 | 1-[4-(6-methyl-7-oxo-1H-pyrrolo[2,3-c]pyridin-4-yl)benzoyl]piperidine-4-carboxamide | 1H NMR (400 MHz, DMSO-d6): δ 12.14 (s, 1H), 7.64 (d, J = 8.0 Hz, 2H), 7.48-7.42 (m, 3H), 7.34 (s, 1H), 7.28 (s, 1H), 6.80 (s, 1H), 6.46 (s, 1H), 3.56 (s, 3H), 3.17-3.14 (m, 1H), 2.68-2.64 (m, 2H), 2.33-2.29 (m, 1 H), 1.83-1.62 (m, 2H), 1.57-1.42 (m, 2H). | 379 |
| 34 | 4-(6-methyl-7-oxo-1H-pyrrolo[2,3-c]pyridin-4-yl)-N-(3-pyridyl)benzamide | 1H NMR (400 MHz, DMSO-d6): δ 12.18 (s, 1H), 10.46 (s, 1H), 8.94 (d, J = 2.0 Hz, 1H), 8.30-8.05 (m, 2H), 8.12-8.05 (m, 2H), 7.76 (d, J = 8.4 Hz, 2H), 7.52 (s, 1H), 7.40-7.37 (m, 1H), 6.49 (d, J = 2.0 Hz, 1H), 3.59 (s, 3H). | 345 |
| 35 | 4-(6-methyl-7-oxo-1H-pyrrolo[2,3-c]pyridin-4-yl)-N-phenyl-benzamide | 1H NMR (400 MHz, DMSO-d6): δ 12.17 (s, 1H), 10.26 (s, 1H), 8.04 (d, J = 8.0 Hz, 2H), 7.87-7.68 (m, 4H), 7.50 (s, 1H), 7.40-7.29 (m, 3H), 7.17-7.15 (m, 1H), 6.49 (s, 1H), 3.59 (s, 3H). | 344 |
| 36 | N-methyl-4-(6-methyl-7-oxo-1H-pyrrolo[2,3-c]pyridin-4-yl)-N-phenyl-benzamide | 1H NMR (400 MHz, DMSO-d6): δ 12.14 (s, 1H), 7.46-7.33 (m, 9H), 7.24-7.17 (m, 3H), 6.36 (d, J = 4.2 Hz, 1H), 3.55 (s, 3H), 3.40 (s, 3H). | 358 |
| 37 | N-benzyl-4-(6-methyl-7-oxo-1H-pyrrolo[2,3-c]pyridin-4-yl)benzamide | 1H NMR (400 MHz, DMSO-d6): δ 12.19 (s, 1H), 9.09 (t, J = 6.0 Hz, 1H), 8.00 (d, J = 4.8 Hz, 2H), 7.71 (d, J = 4.4 Hz, 2H), 7.50 (s, 1H), 7.39-7.25 (m, 5H), 6.52-6.48 (m, 1H), 4.51 (d, J = 5.6 Hz, 2H), 3.60 (s, 3H). | 358 |
| 38 | N-(cyanomethyl)-N-methyl-4-(6-methyl-7-oxo-1H-pyrrolo[2,3-c]pyridin-4-yl)benzamide | 1H NMR (400 MHz, DMSO-d6): δ 12.16 (s, 1H), 7.72-7.63 (m, 2H), 7.60-7.53 (m, 2H), 7.50-7.45 (m, 1H), 7.35 (s, 1H), 6.47 (s, 1H), 4.53 (s, 2H), 3.57 (s, 3H), 3.06 (s, 3H). | 321 |

Example 39

4-[4-(1-hydroxy-1-methyl-ethyl)phenyl]-6-methyl-1H-pyrrolo[2,3-c]pyridin-7-one

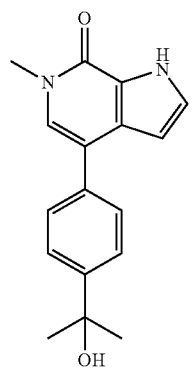 [SMILES: Cn1cc(-c2ccc(C(C)(C)O)cc2)c2cc[nH]c2c1=O]

Step 1:

2-(4-bromophenyl)propan-2-ol

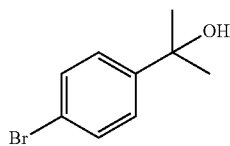

n-Butyl lithium (6.8 mL, 17.0 mmol) was added dropwise to a stirred and cooled (−78° C.) solution of 1,4-dibromobenzene (4.0 g, 16.9 mmol) in THF (50 mL). After addition, stirring at −78° C. was continued for 1 h, and acetone (3.0 g, 51.7 mmol) was added dropwise. The resulting mixture was warmed to 0° C. and stirred for another 3 h before being quenched by addition of saturated aqueous ammonium chloride (40 mL). The mixture was extracted with 75% ethyl acetate/petroleum ether (3×50 mL). The combined organic extracts were washed with brine (50 mL), dried over sodium sulfate and concentrated under reduced pressure to give title compound (1.8 g, 50% yield) as a colorless oil. LCMS M/Z [M-OH$^+$] 197.0.

Step 2:

2-(4-(4,4,5,5-tetramethyl-1,3,2-dioxaborolan-2-yl)phenyl)propan-2-ol

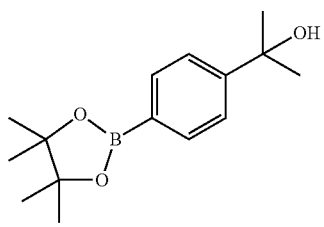 [SMILES: CC(C)(O)c1ccc(B2OC(C)(C)C(C)(C)O2)cc1]

A mixture of potassium acetate (1.4 g, 13.9 mmol), 4,4,4',4',5,5,5',5'-octamethyl-2,2'-bi(1,3,2-dioxaborolane) (2.2 g, 8.4 mmol), 2-(4-bromophenyl)propan-2-ol (1.5 g, 7.0 mmol) and [1,1'-bis(diphenylphosphino)ferrocene]palladium(II) dichloride (0.15 g, 0.2 mmol) in dioxane (15 mL) was degassed for 30 min and then heated at 80° C. for 12 h under nitrogen. After cooling, the reaction mixture was filtered through a pad of Celite using ethyl acetate to rinse. The filtrate was evaporated and the residue was purified by silica gel chromatography (petroleum ether:ethyl acetate 1:1) to give the title compound (1.1 g, 68.7% yield) as a colorless oil.

Step 3:

4-bromo-6-methyl-1H-pyrrolo[2,3-c]pyridin-7-one

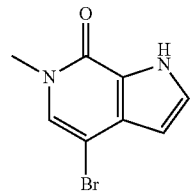

Sodium hydroxide (0.94 g, 23.6 mmol) in water (4 mL) was added slowly to a solution of 4-bromo-6-butyl-1H-pyrrolo[2,3-c]pyridin-7-one (Intermediate B, 1.8 g, 4.7 mmol) in methanol (40 mL). The resulting mixture was heated at 80° C. for 2 h. After cooling, the mixture was concentrated under reduced pressure and the aqueous residue was diluted with water (30 mL). The resulting precipitated was collected by filtration, washed with water (2×30 mL) and concentrated under reduced pressure to give the title compound (0.9 g, 84% yield) as a white solid. LCMS M/Z (M+1) 227.

Step 4:

6-butyl-4-(4-(2-hydroxypropan-2-yl)phenyl)-1H-pyrrolo[2,3-c]pyridin-7(6H)-one

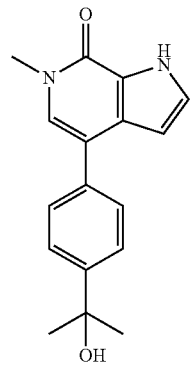 [SMILES: Cn1cc(-c2ccc(C(C)(C)O)cc2)c2cc[nH]c2c1=O]

A mixture of 4-bromo-6-methyl-1H-pyrrolo[2,3-c]pyridin-7-one (Step 3, 200 mg, 0.88 mmol), 2-(4-(4,4,5,5-tetramethyl-1,3,2-dioxaborolan-2-yl)phenyl)propan-2-ol (Step 2, 277 mg, 1.1 mmol), cesium carbonate (574 mg, 1.8 mmol) and [1,1'-bis(diphenylphosphino)ferrocene]palladium(II) dichloride (0.02 g, 0.03 mmol) in dioxane (6 mL) and water (1 mL) was heated at 90° C. for 3 h under nitrogen. After cooling, the mixture was filtered through Celite using ethyl acetate to rinse. The filtrate was concentrated under reduced pressure and the residue was purified by silica gel chromatography (petroleum ether:ethyl acetate=1:1) to give the title compound (38.5 mg, 16% yield) as a white solid. $^1$H NMR (400 MHz, DMSO-d6): δ 12.13 (s, 1H), 7.55-7.50 (m, 4H), 7.34-7.33 (m, 2H), 6.44-6.43 (m, 1H), 5.04 (s, 1H), 3.57 (s, 3H), 1.46 (s, 6H). LCMS M/Z (M+H) 282.8

Example 40 was prepared in a similar fashion to Example 39 from 2-iodopropane:

| Example | IUPAC Compound Name | NMR | m/z |
| --- | --- | --- | --- |
| 40 | 4-[4-(1-hydroxy-1-methyl-ethyl)phenyl]-6-isopropyl-1H-pyrrolo[2,3-c]pyridin-7-one | 1H NMR (400 MHz, DMSO-d6): δ 12.07 (s, 1H), 7.56-7.51 (m, 4H), 7.34 (t, J = 2.8 Hz, 1H), 7.23 (s, 1H), 6.42 (t, J = 2.4 Hz, 1H), 5.33-5.26 (m, 1H), 5.02 (s, 1H), 1.46 (s, 6H), 1.37 (d, J = 6.8 Hz, 6H). | 310 |

Example 41

6-cyclopropyl-4-(4-(2-hydroxypropan-2-yl)phenyl)-1H-pyrrolo[2,3-c]pyridin-7(6H)-one

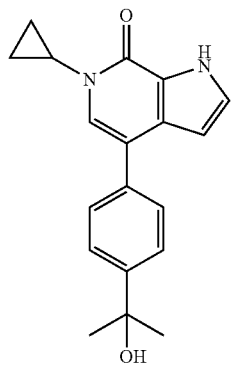 [SMILES: CC(C)(O)c1ccc(-c2cn(C3CC3)c(=O)c3[nH]ccc23)cc1]

Step 1:

4-bromo-6-cyclopropyl-1-(p-tolylsulfonyl)pyrrolo[2,3-c]pyridin-7-one

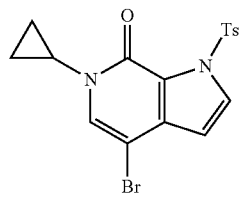 [SMILES: Cc1ccc(S(=O)(=O)n2ccc3c(Br)cn(C4CC4)c(=O)c32)cc1]

To a mixture of 4-bromo-1-(p-tolylsulfonyl)-6H-pyrrolo[2,3-c]pyridin-7-one (Intermediate A) (1.0 g, 2.7 mmol), cyclopropylboronic acid (480 mg, 5.6 mol) and Cu(OAc)$_2$ (500 mg, 2.7 mmol) in dichloroethane (30 mL) was added 2,2'-bipyridine (421 mg, 2.7 mmol) followed by sodium bicarbonate (600 mg, 5.7 mmol). The resulting mixture was heated at 70° C. for 12 h. After cooling, the mixture was filtered though a small pad of Celite using ethyl acetate to rinse. The filtrate was concentrated under reduced pressure and the residue was purified by silica gel chromatography (petroleum ether:ethyl acetate 10:1 to 3:1) to give the title compound (0.6 g, 54.5% yield) as a light yellow solid. LCMS M/Z (M+1) 408.7.

Step 2:

4-bromo-6-cyclopropyl-1H-pyrrolo[2,3-c]pyridin-7(6H)-one

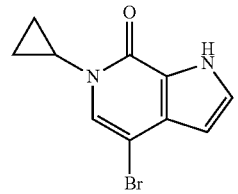 [SMILES: O=c1c2[nH]ccc2c(Br)cn1C1CC1]

Sodium hydroxide (0.3 g, 7.5 mmol) in water (1.5 mL) was added slowly to a solution of 4-bromo-6-cyclopropyl-1-(p-tolylsulfonyl)pyrrolo[2,3-c]pyridin-7-one (0.6 g, 1.5 mmol) in MeOH (15 mL) and water (1.5 mL). The resulting mixture was heated at 80° C. for 3 h. After cooling, the mixture was partially concentrated under reduced pressure and the aqueous residue was diluted with water (30 mL). The resulting precipitated was collected by filtration to provide the title compound (307 mg, 81.2% yield) as a white solid. This crude material was used for next step without further purification. LCMS M/Z (M+1) 252.6.

Step 3:

6-cyclopropyl-4-(4-(2-hydroxypropan-2-yl)phenyl)-1H-pyrrolo[2,3-c]pyridin-7(6H)-one

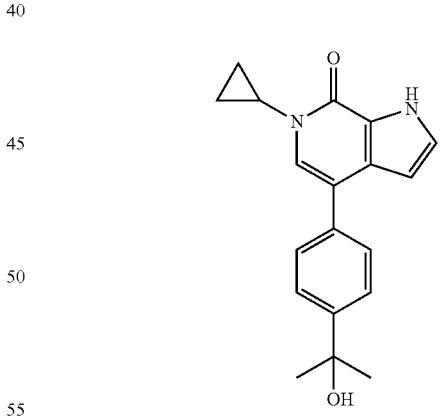

A mixture of 4-bromo-6-cyclopropyl-1H-pyrrolo[2,3-c]pyridin-7(6H)-one (252 mg, 1.0 mmol), 2-(4-(4,4,5,5-tetramethyl-1,3,2-dioxaborolan-2-yl)phenyl)propan-2-ol (315 mg, 1.2 mmol), cesium carbonate (652 mg, 2.0 mmol) and [1,1'-bis(diphenylphosphino)ferrocene]palladium(II) dichloride (73 mg, 0.1 mmol) in dioxane 10 mL and water (2 mL) was heated at 90° C. for 3 h under nitrogen protection. After cooling, the mixture was filtered through a small pad of Celite using ethyl acetate to rinse. The filtrate was concentrated under reduced pressure and the residue was purified by preparative HPLC, acetonitrile:water (10 nM ammonia bicarbonate), 55%-85%, to give the title compound (38.9 mg, 12.7% yield) as a white solid. ¹H NMR (400 MHz, DMSO-d6): δ 12.10 (s, 1H), 7.55-7.50 (m, 4H), 7.35-7.33 (t, J=2.8 Hz, 1H), 7.07 (s, 1H), 6.41 (d, J=2.4 Hz, 1H), 5.02 (s, 1H), 3.41-3.36 (m, 1H), 1.46 (s, 6H), 1.05-1.00 (m, 2H), 0.99-0.92 (m, 2H). LCMS M/Z (M+H) 308.9.

Example 42

6-methyl-4-[4-(1-methyl-4-piperidyl)phenyl]-1H-pyrrolo[2,3-c]pyridin-7-one

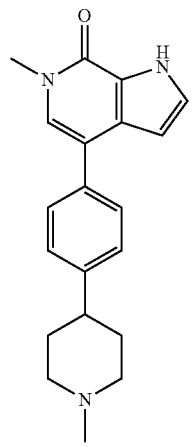 [SMILES: CN1CCC(c2ccc(-c3cn(C)c(=O)c4[nH]ccc34)cc2)CC1]

Step 1:

4-(4-bromophenyl)-1-methylpiperidine

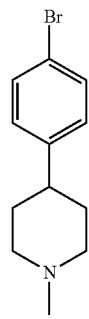

A mixture of 4-(4-bromophenyl)piperidine (200 mg, 0.84 mmol) and formaldedyde (35-40% in water, 1 mL) in methanol (15 mL) was stirred at 30° C. for 5 h. Sodium borohydride (80 mg, 2.12 mmol) was added in portions. After addition, stirring was continued for 30 min, at which time TLC indicated that the reaction had gone to completion. The mixture reaction was quenched by addition of saturated aqueous ammonium chloride (10 mL) and then adjusted to pH 8-9 by adding saturated aqueous sodium bicarbonate. The resulting mixture was extracted with ethyl acetate (3×20 mL). The combined organic extracts were dried over sodium sulfate and concentrated under reduced pressure. The residue was purified by preparative TLC (dichloromethane:methanol 10:1) to give the title compound (120 mg, 56.7% yield) as a white solid. LCMS M/Z (M+H) 255.3.

Step 2:

6-methyl-4-[4-(1-methyl-4-piperidyl)phenyl]-1-(p-tolylsulfonyl)pyrrolo[2,3-c]pyridin-7-one

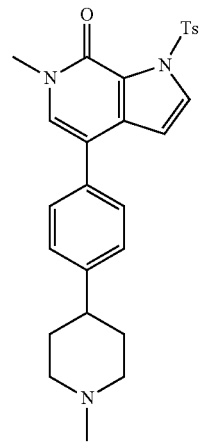 [SMILES: Cc1ccc(S(=O)(=O)n2ccc3c(-c4ccc(C5CCN(C)CC5)cc4)cn(C)c(=O)c32)cc1]

A mixture of 4-(4-bromophenyl)-1-methylpiperidine (180 mg, 0.72 mmol), 6-methyl-1-(p-tolylsulfonyl)-4-(4,4,5,5-tetramethyl-1,3,2-dioxaborolan-2-yl)pyrrolo[2,3-c]pyridin-7-one (Intermediate C) (200 mg, 0.47 mmol), cesium carbonate (520 mg, 1.60 mmol) and [1,1'-bis(diphenylphosphino)ferrocene]palladium(II) dichloride (10 mg, 0.01 mmol) in dioxane (1.5 mL) and water (0.5 mL) was subjected to microwave irradiation at 110° C. for 0.5 h. After cooling, the reaction mixture was partitioned between water (15 mL) and ethyl acetate (30 mL). The separated organic solution was dried over sodium sulfate and concentrated under reduced pressure. The residue was purified by preparative TLC (dichloromethane:methanol 10:1) to give the title compound (130 mg, 58.3% yield) as a yellow solid. LCMS M/Z (M+H) 476.2.

Step 3:

6-methyl-4-[4-(1-methyl-4-piperidyl)phenyl]-1H-pyrrolo[2,3-c]pyridin-7-one

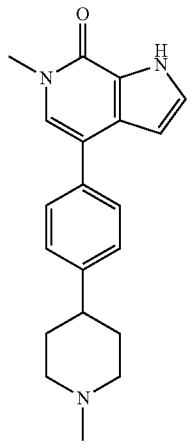 [SMILES: CN1CCC(c2ccc(-c3cn(C)c(=O)c4[nH]ccc34)cc2)CC1]

A solution of 6-methyl-4-[4-(1-methyl-piperidin-4-yl)-phenyl]-1-(toluene-4-sulfonyl)-1,6-dihydro-pyrrolo[2,3-c]

pyridin-7-one (130 mg, 0.27 mmol) in dioxane (10 mL) and aqueous sodium hydroxide (2.5 N, 2 mL) was heated at 100° C. for 1 h. After cooling, the mixture was adjusted to pH=7.0 using 2 N hydrochloric acid and then concentrated under reduced pressure. The residue was purified by preparative HPLC, acetonitrile:water (10 nM ammonia) 35%-65%, to give the title compound (16.6 mg, 18.9% yield) as a white solid. $^1$H NMR (400 MHz, CD$_3$OD): δ 7.55 (d, J=8.0 Hz, 2H), 7.40-7.36 (m, 3H), 7.26 (s, 1H), 6.54 (d, J=2.8 Hz, 1H), 3.72 (s, 3H), 3.05-3.02 (m, 2H), 2.65-2.63 (m, 1H), 2.36 (s, 3H), 2.23-2.18 (m, 2H), 1.90-1.84 (m, 4H). LCMS M/Z (M+H) 322.1.

The following compounds were prepared in a similar fashion to Example 42.

| Example | IUPAC Compound Name | NMR | m/z |
|---|---|---|---|
| 43 | 6-methyl-4-[3-(1-methyl-4-piperidyl)phenyl]-1H-pyrrolo[2,3-c]pyridin-7-one | 1H NMR (400 MHz, CD3OD): δ 7.49-7.39 (m, 4H), 7.26 (d, J = 4.0 Hz, 2H), 6.52 (d, J = 2.4 Hz, 1H), 3.73 (s, 3H), 3.05-3.02 (m, 2H), 2.65-2.63 (m, 1H), 2.35 (s, 3H), 2.20-2.17 (m, 2H), 1.92-1.8 (m, 4H). | 322 |
| 44 | 6-methyl-4-(2-methyl-3,4-dihydro-1H-isoquinolin-6-yl)-1H-pyrrolo[2,3-c]pyridin-7-one | 1H NMR (400 MHz, CD3OD): δ 7.41-7.39 (m, 3H), 7.26 (s, 1H), 7.18 (d, J = 7.2 Hz, 1H), 6.53 (d, J = 3.2 Hz, 1H), 3.72 (s, 3H), 3.68 (s, 2H), 3.05-3.03 (m, 2H), 2.82-2.79 (m, 2H), 2.51 (s, 3H). | 294 |

Example 45

6-methyl-4-[4-[(1-methyl-4-piperidyl)methyl]phenyl]-1H-pyrrolo[2,3-c]pyridin-7-one

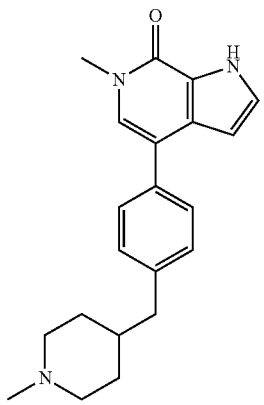 [SMILES: CN1CCC(Cc2ccc(-c3cn(C)c(=O)c4[nH]ccc34)cc2)CC1]

Step 1:

tert-butyl 4-(4-bromobenzyl)piperidine-1-carboxylate

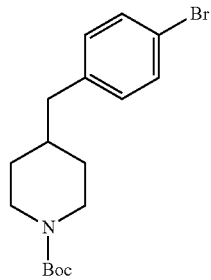 [SMILES: CC(C)(C)OC(=O)N1CCC(Cc2ccc(Br)cc2)CC1]

A mixture of tert-butyl 4-formylpiperidine-1-carboxylate (500 mg, 2.34 mmol) and tosylhydrazide (436 mg, 2.34 mmol) in dioxane (15 mL) was heated at 80° C. for 1.5 h. After cooling, (4-bromophenyl)boronic acid (500 mg, 2.49 mmol) and potassium carbonate (486 mg, 2.49 mmol) were added. The resulting mixture was heated at 100° C. for 3 h. The mixture was concentrated under reduced pressure and the residue was diluted with water (25 mL). The mixture was then extracted with ethyl acetate (3×40 mL). The combined organic extracts were dried over sodium sulfate and concentrated under reduced pressure. The residue was purified by preparative TLC (petroleum ether:ethyl acetate 3:1) to give title compound (200 mg, 36.4% yield) as a white solid. LCMS M/Z (M+H) 255.3.

Step 2:

4-(4-bromobenzyl)-1-methylpiperidine

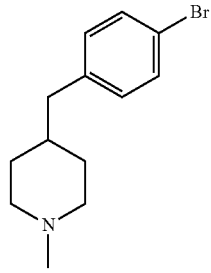

A solution of tert-butyl 4-(4-bromobenzyl)piperidine-1-carboxylate (200 mg, 0.57 mmol) in ethyl acetate (15 mL) was treated with HCl (2 N in ethyl acetate, 1 mL) for 1 h at room temperature. The mixture was concentrated under reduced pressure, and the residue was combined with formaldehyde (35-40% aqueous solution, 1 mL) and methanol (5 mL). The resulting mixture was stirred for 5 h at room temperature, and then sodium borohydride (100 mg, 2.64 mmol) was added in portions. After addition, stirring was continued for 30 min. The reaction was quenched by addition of saturated aqueous ammonium chloride (5 mL), and the mixture was adjusted to pH 8-9 by adding saturated aqueous sodium bicarbonate. The mixture was then extracted with ethyl acetate (3×30 mL). The combined organic extracts were dried over sodium sulfate and concentrated under reduced pressure. The residue was purified by preparative TLC (dichloromethane:methanol 10:1) to give the title compound (50 mg, 32.9% over 2 steps) as a white solid. LCMS M/Z (M+H) 267.2.

Step 3:

6-methyl-4-[4-[(1-methyl-4-piperidyl)methyl]phenyl]-1H-pyrrolo[2,3-c]pyridin-7-one

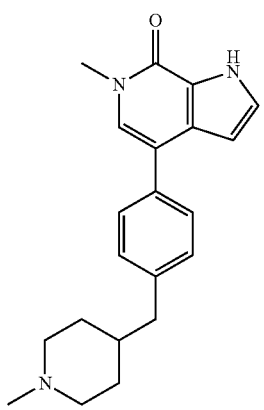 [SMILES: CN1CCC(Cc2ccc(-c3cn(C)c(=O)c4[nH]ccc34)cc2)CC1]

A mixture of 4-(4-bromobenzyl)-1-methylpiperidine (50 mg, 0.19 mmol), 6-methyl-1-(p-tolylsulfonyl)-4-(4,4,5,5-tetramethyl-1,3,2-dioxaborolan-2-yl)pyrrolo[2,3-c]pyridin-7-one (Intermediate C) (95 mg, 0.22 mmol), cesium carbonate (125 mg, 0.38 mmol) and [1,1'-bis(diphenylphosphino)ferrocene]palladium(II) dichloride (15 mg, 0.02 mmol) in dioxane (2 mL) and water (0.5 mL) was subjected to microwave irradiation at 110° C. for 0.5 h. After cooling, the reaction mixture was partitioned between water (5 mL) and ethyl acetate (20 mL). The separated organic solution was dried over sodium sulfate and concentrated under reduced pressure. The residue was purified by preparative TLC (dichloromethane:methanol 10:1) to give the expected intermediate (ca. 80 mg, 70% purity). The material was dissolved in dioxane (5 mL) and 2.5 N aqueous sodium hydroxide (1 mL). The mixture was heated at 100° C. for 1 h. After cooling, the mixture was adjusted to pH=7.0 using 2 N HCl and then concentrated under reduced pressure. The residue was purified by preparative HPLC, acetonitrile:water (10 nM ammonia) 34%-64%, to give the title compound (7.0 mg, 10.9% over 2 steps) as a white solid. $^1$H NMR (400 MHz, CD$_3$OD): δ 7.53 (d, J=8.0 Hz, 2H), 7.39 (s, 1H), 7.29-7.25 (m, 3H), 6.55 (d, J=2.8 Hz, 1H), 3.72 (s, 3H), 2.90-2.87 (m, 2H), 2.63-2.62 (m, 2H), 2.27 (s, 3H), 2.03-2.00 (m, 2H), 1.73-1.62 (m, 3H), 1.37-1.34 (m, 2H). LCMS M/Z (M+H) 336.2.

Example 46 was prepared in a similar fashion to Example 45.

| Example | IUPAC Compound Name | NMR | m/z |
|---|---|---|---|
| 46 | 6-methyl-4-[3-[(1-methyl-4-piperidyl)methyl]phenyl]-1H-pyrrolo[2,3-c]pyridin-7-one | 1H NMR (400 MHz, CD3OD): δ 7.45-7.39 (m, 4H), 7.27 (s, 1H), 7.20-7.18 (m, 1H), 6.52 (d, J = 2.8 Hz, 1H), 3.72 (s, 3H), 2.92-2.88 (m, 2H), 2.66-2.64 (m, 2H), 2.29 (s, 3H), 2.08-2.03 (m, 2H), 1.71-1.65 (m, 3H), 1.38-1.33 (m, 2H). | 336 |

Example 47

3-(2,6-dimethyl-7-oxo-1H-pyrrolo[2,3-c]pyridin-4-yl)-N,N-dimethyl-benzamide

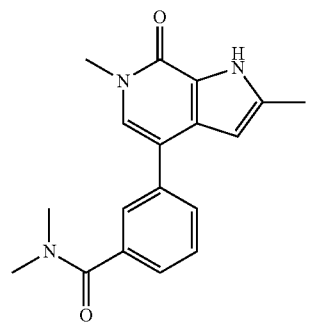

Step 1:

4-bromo-2,6-dimethyl-1H-pyrrolo[2,3-c]pyridin-7(6H)-one

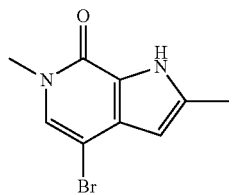

Methyl iodide (112 mg, 0.79 mmol) was added dropwise to a stirred mixture of 4-bromo-2-methyl-1H-pyrrolo[2,3-c]pyridin-7(6H)-one (Intermediate E) (300 mg, 1.32 mmol) and potassium carbonate (274 mg, 1.98 mmol) in DMF (15 mL) at room temperature. After addition, the mixture was stirred at 70° C. for 15 h. The resulting mixture was quenched by addition of water (25 mL) and extracted with ethyl acetate (20 mL×2). The combined organic layers were dried over sodium sulfate and concentrated under reduced pressure. The crude product was purified by preparative TLC (methanol/dichloromethane=1/15) to give the title compound as brown solid (82 mg, 26%). $^1$H NMR (400 MHz, CD3OD): δ 7.33 (s, 1H), 6.07 (s, 1H), 3.58 (s, 3H), 2.39 (s, 3H).

Step 2

3-(2,6-dimethyl-7-oxo-6,7-dihydro-1H-pyrrolo[2,3-c]pyridin-4-yl)-N,N-dimethylbenzamide

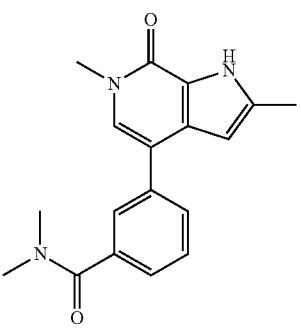

A mixture of 4-bromo-2,6-dimethyl-1H-pyrrolo[2,3-c]pyridin-7(6H)-one (Step 1, 82 mg, 0.34 mmol), (3-(dimethylcarbamoyl)phenyl)boronic acid (66 mg, 0.34 mmol), cesium carbonate (227 mg, 0.70 mmol) in dioxane/water (3.5 mL, 6:1) was added and [1,1'-bis(diphenylphosphino)ferrocene]palladium(II) dichloride (10 mg, 0.013 mmol) under nitrogen atmosphere. The reaction mixture was then heated at 110° C. under nitrogen for 18 h. The reaction was cooled to room temperature, and then the mixture was filtered through Celite. The filtrate was concentrated under reduced pressure and the residue was then purified by preparative HPLC (acetonitrile: water (0.3% formic acid) 25%-55%) to yield title compound as a brown solid (6.9 mg, 6.5%). $^1$H NMR (400 MHz, CD3OD): δ 7.73-7.72 (m, 1H), 7.65 (s, 1H), 7.55-7.59 (m, 1H), 7.2 (d, J=7.6 Hz, 1H), 7.32 (s, 1H), 6.28 (s, 1H), 3.72 (s, 3H), 3.16 (s, 3H), 3.09 (s, 3H), 2.45 (s, 3H). LCMS M/Z (M+H) 310.1

Example 48

Synthesis of biotinylated probe compound (1000) for TAF assay described below.

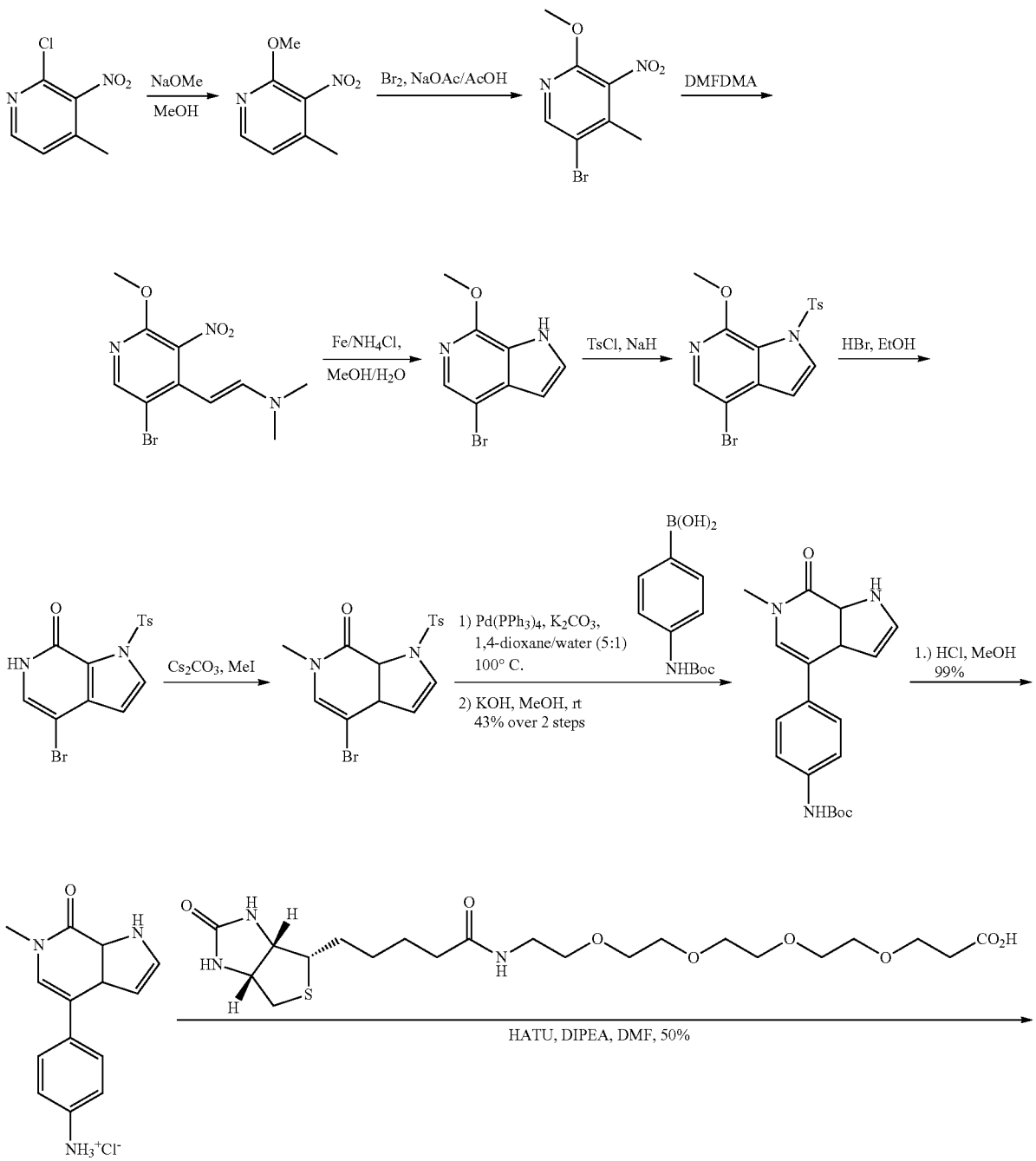

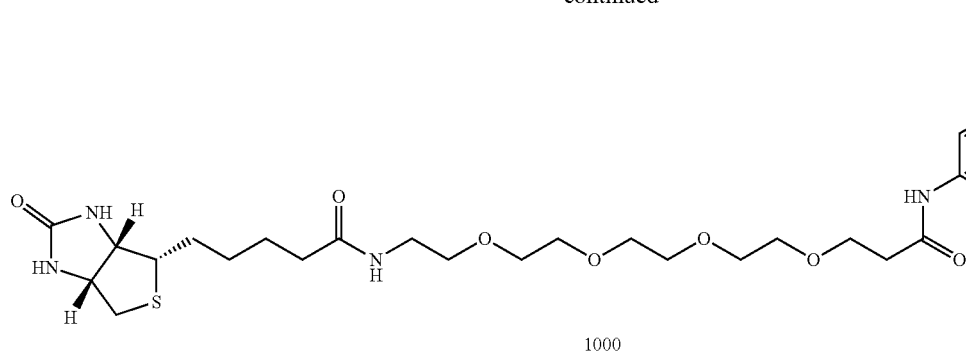

1000

Step 1:

2-methoxy-4-methyl-3-nitropyridine

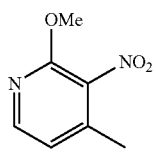

A solution of 2-chloro-4-methyl-3-nitropyridine (250 g, 1.45 mol) in methanol (1.0 L) was added dropwise (2 h) to a stirred and cooled (0° C.) solution of sodium methoxide (250 g, 4.63 mol) in methanol (850 mL). After addition, the mixture was heated to reflux for 23 h, at which time TLC indicated the reaction had gone to completion. The mixture was concentrated under reduced pressure to a volume of approximately 900 mL, and quenched by addition of water (1.5 L). The resulting solid was collected by filtration, washed with water and dried under reduced pressure to give the title compound (250 g, 100% yield) as a brown solid. $^1$H NMR (400 MHz, DMSO-d6): δ 8.22 (d, J=5.2 Hz, 1H), 7.10 (d, J=5.6 Hz, 1H), 3.92 (s, 3H), 2.26 (s, 3H).

Step 2:

5-bromo-2-methoxy-4-methyl-3-nitropyridine

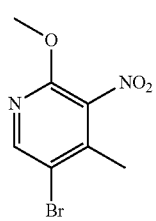

Sodium acetate (365 g, 5.37 mol) was added to a stirred solution of 2-methoxy-4-methyl-3-nitropyridine (250 g, 1.49 mol) in acetic acid (1.5 L) at ambient temperature and then Br$_2$ (639 g, 4.00 mol) was added dropwise (30 min). After addition, the mixture was heated at 80° C. for 12 h, at which time TLC indicated the reaction had gone to completion. The mixture was cooled (0° C.) and quenched by sequential addition of 10% aqueous (1.5 L) and saturated aqueous Na$_2$SO$_3$ (1.5 L). The resulting solid was collected by filtration washed with water, and dried under reduced pressure to give the title compound (302 g, 82.2% yield) as a light yellow solid. $^1$H NMR (400 MHz, DMSO-d6): δ 8.25 (s, 1H), 3.94 (s, 3H), 2.29 (s, 3H).

Step 3:

(E)-2-(5-bromo-2-methoxy-3-nitro-4-pyridyl)-N,N-dimethyl-ethenamine

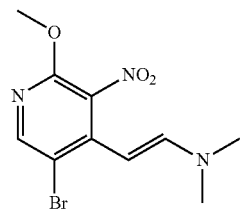 [SMILES: COc1ncc(Br)c(/C=C/N(C)C)c1[N+](=O)[O-]]

DMF-DMA (600 mL) was slowly added to a stirred and heated (80° C.) solution of 5-bromo-2-methoxy-4-methyl-3-nitropyridine (134 g, 0.54 mol) in DMF (1.1 L). After addition, the mixture was heated at 95° C. for 5 h, at which time TLC indicated the reaction had gone to completion. The mixture was cooled to room temperature and poured into ice-cold water (3 L). The resulting red solid was collected by filtration, washed with water, and dried under reduced pressure to give the title compound (167 g, 100% yield) as red solid. $^1$H NMR (400 MHz, DMSO-d6): δ 8.24 (s, 1H), 7.05 (d, J=13.6 Hz, 1H), 7.05 (d, J=13.6 Hz, 1H), 4.80 (d, J=13.2 Hz, 1H), 3.88 (s, 3H), 2.90 (s, 6H).

Step 4:

4-bromo-7-methoxy-1H-pyrrolo[2,3-c]pyridine

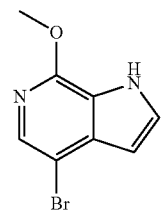

A mixture of 2-(5-bromo-2-methoxy-3-nitropyridin-4-yl)-N,N-dimethylethenamine (50.0 g, 165 mmol), Fe (50.0 g, 893 mmol) and NH$_4$Cl (50.0 g, 943 mmol) in methanol/

H₂O (1900/250 mL) was heated at reflux for 7 h, at which time LCMS indicated that the reaction had gone to completion. The mixture was filtered while hot and the cake was washed with methanol (3×200 mL). The combined filtrate was concentrated under reduced pressure, and the resulting residue was purified by silica gel chromatography (petroleum ether:Ethyl acetate=5:1) to give the crude product. This crude material was triturated with acetonitrile to give the title compound (37.4 g, 99.5% yield) as a light brown solid. LCMS M/Z (M+H) 226.7, 228.7.

Step 5:

4-bromo-7-methoxy-1-(p-tolylsulfonyl)pyrrolo[2,3-c]pyridine

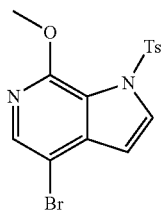 [SMILES: COc1ncc(Br)c2ccn(S(=O)(=O)c3ccc(C)cc3)c12]

A solution of 4-bromo-7-methoxy-1H-pyrrolo[2,3-c]pyridine (34.3 g, 0.15 mol) in THF (700 mL) was added dropwise to a stirred and cooled (0° C.) solution of sodium hydride (60%, 19.2 g, 0.48 mol) in THF (700 mL). After addition, the mixture was stirred at room temperature for 1 h, and then cooled again to 0° C. Tosyl chloride (38.0 g, 0.20 mol) in THF (700 mL) was added dropwise and the resulting mixture was stirred at ambient temperature for 2 h. The reaction was quenched by addition of saturated aqueous ammonium chloride (1.0 L), and then extracted with ethyl acetate (3×600 mL). The combined organic extracts were dried over Na₂SO₄ and concentrated under reduced pressure. The residue was triturated with acetonitrile to give the title compound (51.2 g, 88.9% yield) as a brown solid. This crude material was used in the next step without further purification.

Step 6:

4-bromo-1-(p-tolylsulfonyl)-6H-pyrrolo[2,3-c]pyridin-7-one

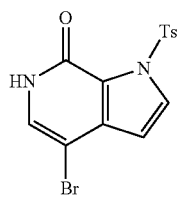 [SMILES: Cc1ccc(S(=O)(=O)n2ccc3c(Br)c[nH]c(=O)c32)cc1]

HBr (40% aqueous, 1.1 L) was added to a solution of 4-bromo-7-methoxy-1-(p-tolylsulfonyl)pyrrolo[2,3-c]pyridine (102.5 g, 0.27 mol) in ethanol (200 mL). After addition, the mixture was heated at 90° C. for 2 h, at which time TLC indicated that the reaction had gone to completion. The mixture was cooled to 0° C. and the resulting white solid was collected by filtration. This solid was washed with water and dried under vacuum to give the title compound (87.5 g, 88.6% yield) as a light brown solid. ¹H NMR (400 MHz, DMSO-d6): δ 11.48 (s, 1H), 8.01 (d, J=3.6 Hz, 1H), 8.90 (d, J=8.0 Hz, 2H), 7.38 (d, J=8.0 Hz, 2H), 7.32 (s, 1H), 6.57 (d, J=3.2 Hz, 1H), 2.34 (s, 3H).

Step 7:

4-bromo-6-methyl-1-(p-tolylsulfonyl)pyrrolo[2,3-c]pyridin-7-one

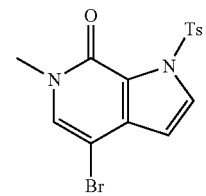 [SMILES: Cc1ccc(S(=O)(=O)n2ccc3c(Br)cn(C)c(=O)c32)cc1]

Methyl iodide (24.5 g, 172.8 mmol) was added dropwise to a stirred suspension of 4-bromo-1-tosyl-1H-pyrrolo[2,3-c]pyridin-7(6H)-one (Intermediate A) (16.7 g, 45.5 mmol) and cesium carbonate (17.8 g, 54.6 mmol) in dioxane (250 mL). After addition, the reaction mixture was stirred at room temperature for 18 h, at which time LCMS indicated the reaction had gone to completion. The solvent was evaporated under reduced pressure, and the residue was diluted with water (200 mL). The mixture was extracted with EtOAc (3×200 mL). The combined organic extracts were dried over sodium sulfate, filtered and concentrated under reduced pressure. The residue was purified by silica gel chromatography (petroleum ether/ethyl acetate=3:1) to give the title compound (14.0 g, 81.4% yield) as a brown solid. ¹H NMR (400 MHz, DMSO-d6): δ 8.03 (d, J=3.6 Hz, 1H), 7.92 (d, J=8.4 Hz, 2H), 7.78 (s, 1H), 7.39 (d, J=8.4 Hz, 2H), 6.57 (d, J=3.6 Hz, 1H), 3.35 (s, 3H), 2.35 (s, 3H).

Step 8:

A 50 mL vial was charged with a magnetic stir bar, 4-bromo-6-methyl-1-tosyl-1H-pyrrolo[2,3-c]pyridin-7(6H)-one (0.281 g, 0.737 mmol), 1,4-dioxane (3.69 ml, 0.737 mmol), water (0.5 ml, 27.8 mmol), K₂CO₃ (0.306 g, 2.211 mmol), 4-(tert-butoxycarbonyl-amino)phenylboronic acid (0.227 g, 0.958 mmol), and Pd(PPh₃)₄ (0.085 g, 0.074 mmol). The vial was purged, placed under an atmosphere of nitrogen and heated to 95° C. with stirring for 12 h before being allowed to cool to room temperature. The reaction was then diluted with water (20 ml). A precipitate formed which was collected via vacuum filtration using a Buchner funnel. The solids were washed with additional water (2×25 mL), dried, and collected. This material was suspended in methanol (5 mL) and treated with KOH (200 mg). After 2 h the MeOH was removed in vacuo and the crude material was suspended in water (20 mL) and the resulting solids were collected via vacuum filtration using a Buchner funnel. The solids were washed with additional water, were collected, and dried in vacuo to afford tert-butyl 4-(6-methyl-7-oxo-6,7-dihydro-1H-pyrrolo[2,3-c]pyridin-4-yl)phenylcarbamate (362 mg, 0.907 mmol) as a light yellow solid. LCMS M/Z (M+H) 494.

Step 9:

A 50 mL round bottom flask was charged with a magnetic stir bar, tert-butyl 4-(6-methyl-7-oxo-6,7-dihydro-1H-pyrrolo[2,3-c]pyridin-4-yl)phenylcarbamate (350 mg, 1.031 mmol), MeOH (2.062 mL, 1.031 mmol), and HCl (1.031 mL, 4.12 mmol) (4N in dioxane). The reaction was then allowed to stir at rt for 4 h before being diluted with dioxane (25 mL). A precipitate formed which was collected via vacuum filtration using a Buchner funnel, washed with additional dioxane, and dried in vacuo to afford 4-(4-aminophenyl)-6-methyl-1H-pyrrolo[2,3-c]pyridin-7(6H)-one (188 mg, 0.786 mmol, 76% yield) as a white solid. LCMS M/Z (M+H) 240.

Step 10:

A 25 mL vial was charged with a magnetic stir bar, 4-(4-aminophenyl)-6-methyl-1Hpyrrolo[2,3-c]pyridin-7 (6H)-one (0.038 g, 0.159 mmol), anhydrous DMF (0.794 ml, 0.159 mmol), DIPEA (0.139 ml, 0.794 mmol), 17-oxo-21-((3aS,4S,6aR)-2-oxohexahydro-1Hthieno[3,4-d]imidazol-4-yl)-4,7,10,13-tetraoxa-16-azahenicosan-1-oic acid (0.078 g, 0.159 mmol), and HATU (0.075 g, 0.199 mmol). The crude reaction mixture was directly purified via reverse phase HPLC to afford N-(4-(6-methyl-7-oxo-6,7-dihydro-1H-pyrrolo[2,3-c]pyridin-4-yl)phenyl)-1-(5-((3aS,4S,6aR)-2-oxohexahydro-1H-thieno[3,4-d]imidazol-4-yl)pentanamido)-3,6,9,12-tetraoxapentadecan-15-amide (31 mg, 0.041 mmol, 26.0% yield). LCMS M/Z (M+2H)/2 357.

Example 49

Synthesis of biotinylated probe compound (1001) for CECR2 assay described below.

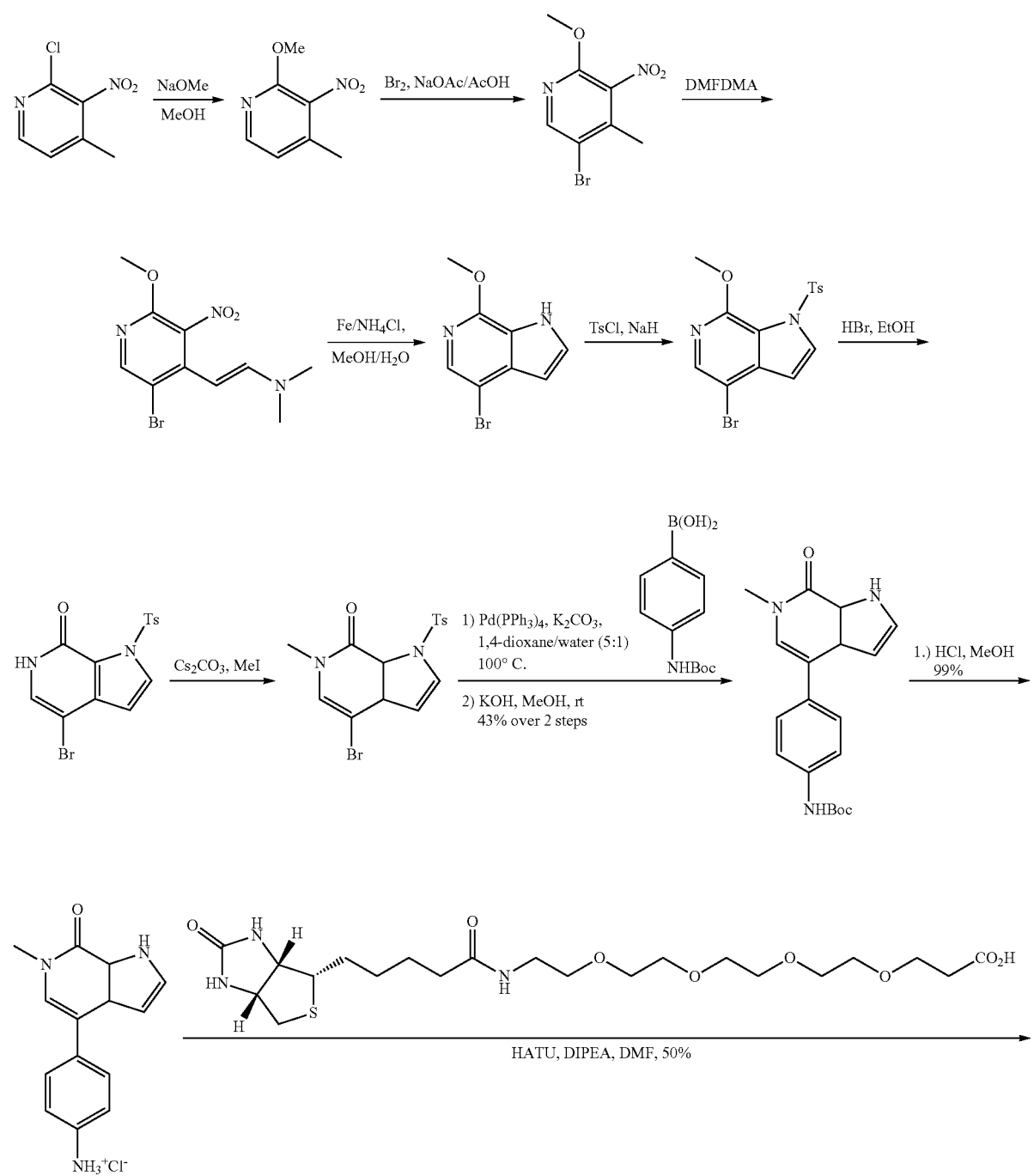

-continued

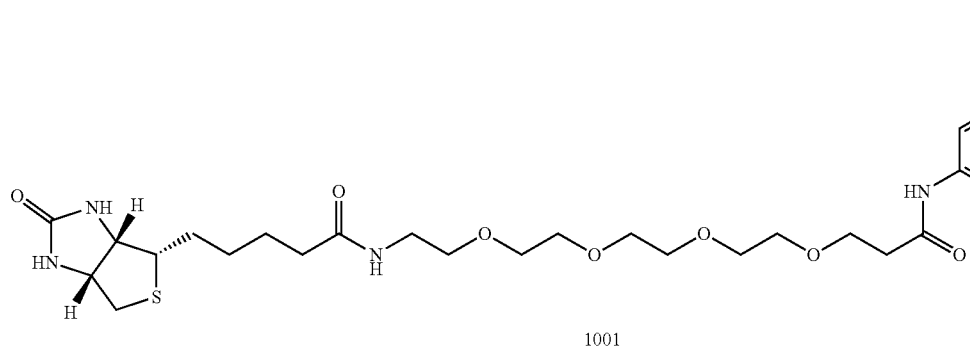

1001

Step 1:

2-methoxy-4-methyl-3-nitropyridine

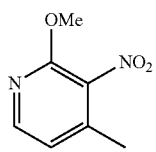

A solution of 2-chloro-4-methyl-3-nitropyridine (250 g, 1.45 mol) in methanol (1.0 L) was added dropwise (2 h) to a stirred and cooled (0° C.) solution of sodium methoxide (250 g, 4.63 mol) in methanol (850 mL). After addition, the mixture was heated to reflux for 23 h, at which time TLC indicated the reaction had gone to completion. The mixture was concentrated under reduced pressure to a volume of approximately 900 mL, and quenched by addition of water (1.5 L). The resulting solid was collected by filtration, washed with water and dried under reduced pressure to give the title compound (250 g, 100% yield) as a brown solid. $^1$H NMR (400 MHz, DMSO-d6): δ 8.22 (d, J=5.2 Hz, 1H), 7.10 (d, J=5.6 Hz, 1H), 3.92 (s, 3H), 2.26 (s, 3H).

Step 2:

5-bromo-2-methoxy-4-methyl-3-nitropyridine

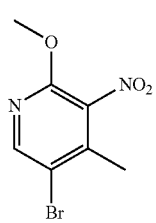

Sodium acetate (365 g, 5.37 mol) was added to a stirred solution of 2-methoxy-4-methyl-3-nitropyridine (250 g, 1.49 mol) in acetic acid (1.5 L) at ambient temperature and then Br$_2$ (639 g, 4.00 mol) was added dropwise (30 min). After addition, the mixture was heated at 80° C. for 12 h, at which time TLC indicated the reaction had gone to completion. The mixture was cooled (0° C.) and quenched by sequential addition of 10% aqueous (1.5 L) and saturated aqueous Na$_2$SO$_3$ (1.5 L). The resulting solid was collected by filtration washed with water, and dried under reduced pressure to give the title compound (302 g, 82.2% yield) as a light yellow solid. $^1$H NMR (400 MHz, DMSO-d6): δ 8.25 (s, 1H), 3.94 (s, 3H), 2.29 (s, 3H).

Step 3:

(E)-2-(5-bromo-2-methoxy-3-nitro-4-pyridyl)-N,N-dimethyl-ethenamine

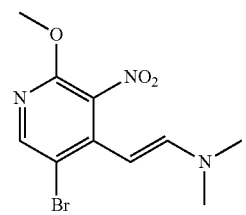 [SMILES: COc1ncc(Br)c(/C=C/N(C)C)c1[N+](=O)[O-]]

DMF-DMA (600 mL) was slowly added to a stirred and heated (80° C.) solution of 5-bromo-2-methoxy-4-methyl-3-nitropyridine (134 g, 0.54 mol) in DMF (1.1 L). After addition, the mixture was heated at 95° C. for 5 h, at which time TLC indicated the reaction had gone to completion. The mixture was cooled to room temperature and poured into ice-cold water (3 L). The resulting red solid was collected by filtration, washed with water, and dried under reduced pressure to give the title compound (167 g, 100% yield) as red solid. $^1$H NMR (400 MHz, DMSO-d6): δ 8.24 (s, 1H), 7.05 (d, J=13.6 Hz, 1H), 7.05 (d, J=13.6 Hz, 1H), 4.80 (d, J=13.2 Hz, 1H), 3.88 (s, 3H), 2.90 (s, 6H).

Step 4:

4-bromo-7-methoxy-1H-pyrrolo[2,3-c]pyridine

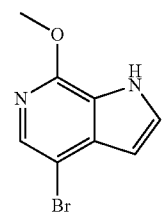

A mixture of 2-(5-bromo-2-methoxy-3-nitropyridin-4-yl)-N,N-dimethylethenamine (50.0 g, 165 mmol), Fe (50.0 g, 893 mmol) and NH$_4$Cl (50.0 g, 943 mmol) in methanol/

H₂O (1900/250 mL) was heated at reflux for 7 h, at which time LCMS indicated that the reaction had gone to completion. The mixture was filtered while hot and the cake was washed with methanol (3×200 mL). The combined filtrate was concentrated under reduced pressure, and the resulting residue was purified by silica gel chromatography (petroleum ether:Ethyl acetate=5:1) to give the crude product. This crude material was triturated with acetonitrile to give the title compound (37.4 g, 99.5% yield) as a light brown solid. LCMS M/Z (M+H) 226.7, 228.7.

Step 5:

4-bromo-7-methoxy-1-(p-tolylsulfonyl)pyrrolo[2,3-c]pyridine

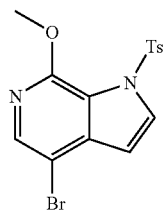 [SMILES: COc1ncc(Br)c2ccn(S(=O)(=O)c3ccc(C)cc3)c12]

A solution of 4-bromo-7-methoxy-1H-pyrrolo[2,3-c]pyridine (34.3 g, 0.15 mol) in THF (700 mL) was added dropwise to a stirred and cooled (0° C.) solution of sodium hydride (60%, 19.2 g, 0.48 mol) in THF (700 mL). After addition, the mixture was stirred at room temperature for 1 h, and then cooled again to 0° C. Tosyl chloride (38.0 g, 0.20 mol) in THF (700 mL) was added dropwise and the resulting mixture was stirred at ambient temperature for 2 h. The reaction was quenched by addition of saturated aqueous ammonium chloride (1.0 L), and then extracted with ethyl acetate (3×600 mL). The combined organic extracts were dried over Na₂SO₄ and concentrated under reduced pressure. The residue was triturated with acetonitrile to give the title compound (51.2 g, 88.9% yield) as a brown solid. This crude material was used in the next step without further purification.

Step 6:

4-bromo-1-(p-tolylsulfonyl)-6H-pyrrolo[2,3-c]pyridin-7-one

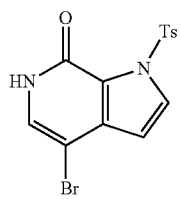 [SMILES: Cc1ccc(S(=O)(=O)n2ccc3c(Br)c[nH]c(=O)c32)cc1]

HBr (40% aqueous, 1.1 L) was added to a solution of 4-bromo-7-methoxy-1-(p-tolylsulfonyl)pyrrolo[2,3-c]pyridine (102.5 g, 0.27 mol) in ethanol (200 mL). After addition, the mixture was heated at 90° C. for 2 h, at which time TLC indicated that the reaction had gone to completion. The mixture was cooled to 0° C. and the resulting white solid was collected by filtration. This solid was washed with water and dried under vacuum to give the title compound (87.5 g, 88.6% yield) as a light brown solid. ¹H NMR (400 MHz, DMSO-d6): δ 11.48 (s, 1H), 8.01 (d, J=3.6 Hz, 1H), 8.90 (d, J=8.0 Hz, 2H), 7.38 (d, J=8.0 Hz, 2H), 7.32 (s, 1H), 6.57 (d, J=3.2 Hz, 1H), 2.34 (s, 3H).

Step 7:

4-bromo-6-methyl-1-(p-tolylsulfonyl)pyrrolo[2,3-c]pyridin-7-one

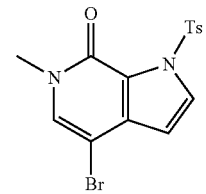 [SMILES: Cc1ccc(S(=O)(=O)n2ccc3c(Br)cn(C)c(=O)c32)cc1]

Methyl iodide (24.5 g, 172.8 mmol) was added dropwise to a stirred suspension of 4-bromo-1-tosyl-1H-pyrrolo[2,3-c]pyridin-7(6H)-one (Intermediate A) (16.7 g, 45.5 mmol) and cesium carbonate (17.8 g, 54.6 mmol) in dioxane (250 mL). After addition, the reaction mixture was stirred at room temperature for 18 h, at which time LCMS indicated the reaction had gone to completion. The solvent was evaporated under reduced pressure, and the residue was diluted with water (200 mL). The mixture was extracted with EtOAc (3×200 mL). The combined organic extracts were dried over sodium sulfate, filtered and concentrated under reduced pressure. The residue was purified by silica gel chromatography (petroleum ether/ethyl acetate=3:1) to give the title compound (14.0 g, 81.4% yield) as a brown solid. ¹H NMR (400 MHz, DMSO-d6): δ 8.03 (d, J=3.6 Hz, 1H), 7.92 (d, J=8.4 Hz, 2H), 7.78 (s, 1H), 7.39 (d, J=8.4 Hz, 2H), 6.57 (d, J=3.6 Hz, 1H), 3.35 (s, 3H), 2.35 (s, 3H).

Step 8:

A 50 mL vial was charged with a magnetic stir bar, 4-bromo-6-methyl-1-tosyl-1H-pyrrolo[2,3-c]pyridin-7(6H)-one (0.281 g, 0.737 mmol), 1,4-dioxane (3.69 ml, 0.737 mmol), water (0.5 ml, 27.8 mmol), K₂CO₃ (0.306 g, 2.211 mmol), 4-(tert-butoxycarbonyl-amino)phenylboronic acid (0.227 g, 0.958 mmol), and Pd(PPh₃)₄ (0.085 g, 0.074 mmol). The vial was purged, placed under an atmosphere of nitrogen and heated to 95° C. with stirring for 12 h before being allowed to cool to room temperature. The reaction was then diluted with water (20 ml). A precipitate formed which was collected via vacuum filtration using a Buchner funnel. The solids were washed with additional water (2×25 mL), dried, and collected. This material was suspended in methanol (~5 mL) and treated with KOH (200 mg). After 2 h the MeOH was removed in vacuo and the crude material was suspended in water (~20 mL) and the resulting solids were collected via vacuum filtration using a Buchner funnel. The solids were washed with additional water, were collected, and dried in vacuo to afford tert-butyl 4-(6-methyl-7-oxo-6,7-dihydro-1H-pyrrolo[2,3-c]pyridin-4-yl)phenylcarbamate (362 mg, 0.907 mmol) as a light yellow solid. LCMS M/Z (M+H) 494.

Step 9:

A 50 mL round bottom flask was charged with a magnetic stir bar, tert-butyl 4-(6-methyl-7-oxo-6,7-dihydro-1H-pyrrolo[2,3-c]pyridin-4-yl)phenylcarbamate (350 mg, 1.031 mmol), MeOH (2.062 mL, 1.031 mmol), and HCl (1.031 mL, 4.12 mmol) (4N in dioxane). The reaction was then allowed to stir at rt for 4 h before being diluted with dioxane (25 mL). A precipitate formed which was collected via vacuum filtration using a Buchner funnel, washed with additional dioxane, and dried in vacuo to afford 4-(4-aminophenyl)-6-methyl-1H-pyrrolo[2,3-c]pyridin-7(6H)-one (188 mg, 0.786 mmol, 76% yield) as a white solid. LCMS M/Z (M+H) 240.

Step 10:

A 25 mL vial was charged with a magnetic stir bar, 4-(4-aminophenyl)-6-methyl-1Hpyrrolo[2,3-c]pyridin-7 (6H)-one (0.038 g, 0.159 mmol), anhydrous DMF (0.794 ml, 0.159 mmol), DIPEA (0.139 ml, 0.794 mmol), 17-oxo-21 ((3aS,4S,6aR)-2-oxohexahydro-1Hthieno[3,4-d]imidazol-4-yl)-4,7,10,13-tetraoxa-16-azahenicosan-1-oic acid (0.078 g, 0.159 mmol), and HATU (0.075 g, 0.199 mmol). The crude reaction mixture was directly purified via reverse phase HPLC to afford N-(4-(6-methyl-7-oxo-6,7-dihydro-1H-pyrrolo[2,3-c]pyridin-4-yl)phenyl)-1-(5-((3aS,4S,6aR)-2-oxohexahydro-1H-thieno[3,4-d]imidazol-4-yl)pentanamido)-3,6,9,12-tetraoxapentadecan-15-amide (31 mg, 0.041 mmol, 26.0% yield). LCMS M/Z (M+2H)/2 357.

Example 50

The inhibitory activity of representative compounds against bromodomains can be evaluated using known methods or using one of the following assay protocols.

$IC_{50}$ Measurements for Inhibitors Using BRD4 AlphaLisa Binding Assay

His/Flag epitope tagged BRD4 $BD1_{42-168}$ was cloned, expressed, and purified to. BRD4 binding and inhibition was assessed by monitoring the engagement of biotinylated H4-tetraacetyl peptide (New England Peptide, NEP2069-1/13) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minutes incubation at room temperature Alpha streptavidin donor beads and AlphaLisa anti-Flag acceptor beads were added to a final concentration of 10 ug/mL each. After three hours equilibration plates were read on an Envision instrument and $IC_{50}$s calculated using a four parameter non-linear curve fit.

$IC_{50}$ Measurements for Inhibitors Using BRD9 AlphaLisa Binding Assay

His/Flag epitope tagged $BRD9_{134-239}$ was cloned, expressed, and purified to homogeneity. BRD9 binding and inhibition was assessed by monitoring the engagement of biotinylated H4-tetraacetyl peptide (New England Peptide, NEP2069-11/13) with the target using the AlphaLisa technology (Perkin-Elmer). Specifically, in a 384 well ProxiPlate BRD9 (50 nM final) was combined with peptide (3 nM final) in 50 mM HEPES (pH 7.5), 150 mM NaCl, 1 mM TCEP, 0.01% (w/v) BSA, and 0.008% (w/v) Brij-35 either in the presence of DMSO (final 0.8% DMSO) or compound dilution series in DMSO. After 20 minutes incubation at room temperature AlphaLisa Streptavidin Acceptor Beads (Perkin-AL125C) and AlphaLisa Nickel donor beads (Perkin AS 10 ID) were added to a final concentration of 15 ug/mL each. After ninety minutes of equilibration in the dark, the plates were read on an Envision instrument and $IC_{50}$s calculated using a four parameter non-linear curve fit.

$IC_{50}$ Measurements for Inhibitors Using TAF1-BD2 TR-FRET Binding Assay

His/Flag epitope tagged $TAF1-BD2_{1504-1635}$ was cloned, expressed, and purified to homogeneity. TAF1-BD2 binding and inhibition was assessed by monitoring the engagement of a biotinylated small molecule compound 1000 (Example 48) with the target using the TR-FRET assay technology (Perkin-Elmer). Specifically, in a 384 well ProxiPlate TAF1-BD2 (6 nM final) was combined with biotin-ligand (50 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 10 minutes incubation at room temperature, a mixture Eu-W1024 Anti-6×His antibody (Perkin Elmer AD0110) and SureLight™ Allophycocyanin-Streptavidin (APC-SA, Perkin Elmer CR130-100) were added to a final concentrations of 0.2 nMolar antibody and 25 nMolar APC-SA, respectively. After twenty minutes of equilibration, the plates were read on an Envision instrument and $IC_{50}$s calculated using a four parameter non-linear curve fit. Novel compound 1000 and the TAF1-BD2 TR-FRET Binding Assay described above represent additional embodiments of the invention.

IC50 Measurements for Inhibitors Using CECR2 TR-FRET Binding Assay

His/Flag epitope tagged $CECR2_{424-538}$ was cloned, expressed, and purified to homogeneity. CECR2 binding and inhibition was assessed by monitoring the engagement of a biotinylated small molecule compound 1001 (Example 49) with the target using the TR-FRET assay technology (Perkin-Elmer). Specifically, in a 384 well ProxiPlate CECR2 (1.5 nM final) was combined with biotin-ligand (25 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 15 minutes incubation at room temperature, a mixture Eu-W1024 Anti-6×His antibody (Perkin Elmer AD0110) and SureLight™ Allophycocyanin-Streptavidin (APC-SA, Perkin Elmer CR130-100) were added to a final concentrations of 0.2 nMolar antibody and 12.5 nMolar APC-SA, respectively. After forty minutes of equilibration, the plates were read on an Envision instrument and $IC_{50}$s calculated using a four parameter non-linear curve fit. Novel compound 1001 and the CECR2 TR-FRET Binding Assay described above represent additional embodiments of the invention.

Data for representative compounds of formula (I) (and other compounds provided herein) from the four assays described above is provided in the following table.

| Example | IC50 (uM) | Assay |
|---|---|---|
| 1 | 0.54 | BRD4 |
| 2 | 0.21 | BRD4 |
| 4 | 0.11 | BRD4 |
| 9 | 0.31 | BRD4 |
| 10 | 0.11 | BRD4 |
| 13 | 0.17 | BRD4 |
| 14 | 0.11 | BRD4 |
| 15 | 0.081 | BRD4 |
| 17 | 0.058 | BRD4 |
| 21 | 0.18 | BRD4 |
| 23 | 0.15 | BRD4 |
| 25 | 0.71 | BRD4 |
| 27 | 0.084 | BRD4 |
| 29 | 0.28 | BRD4 |
| 31 | 0.17 | BRD4 |
| 32 | 0.32 | BRD4 |
| 33 | 0.26 | BRD4 |
| 34 | 0.051 | BRD4 |
| 36 | 0.34 | BRD4 |
| 38 | 0.20 | BRD4 |
| 3 | 0.024 | BRD9 |
| 5 | 0.13 | BRD9 |
| 6 | 0.085 | BRD9 |

-continued

| Example | IC50 (uM) | Assay |
|---|---|---|
| 11 | 0.031 | BRD9 |
| 12 | 0.025 | BRD9 |
| 19 | 0.238 | BRD9 |
| 22 | 0.053 | BRD9 |
| 39 | 0.021 | BRD9 |
| 40 | 4.1 | BRD9 |
| 41 | 0.11 | BRD9 |
| 42 | 0.053 | BRD9 |
| 45 | 0.064 | BRD9 |
| 7 | 0.17 | CECR2 |
| 16 | 0.036 | CECR2 |
| 18 | 0.73 | CECR2 |
| 20 | 1.3 | CECR2 |
| 26 | 0.24 | CECR2 |
| 28 | 0.13 | CECR2 |
| 35 | 0.075 | CECR2 |
| 44 | 0.054 | CECR2 |
| 47 | 0.13 | CECR2 |
| 24 | 0.096 | TAF-1 |
| 30 | 0.35 | TAF-1 |
| 37 | 0.063 | TAF-1 |
| 43 | 0.68 | TAF-1 |
| 46 | 0.44 | TAF-1 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I):

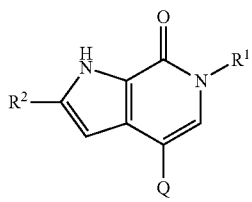

(I)

or a salt thereof, wherein:

$R^1$ is H, methyl, or ethyl;

$R^2$ is H, $C_{1-12}$alkyl, $C_{1-12}$alkenyl, $C_{2-12}$alkynyl, carbocyclyl, or heterocyclyl, wherein each $C_{1-12}$alkyl, $C_{2-12}$alkenyl, $C_{2-12}$alkynyl, carbocyclyl, or heterocyclyl of $R^2$ is optionally substituted with one or more groups $R^b$; and Q is a 5-membered heteroaryl that is optionally substituted with one or more groups $R^c$, or Q is:

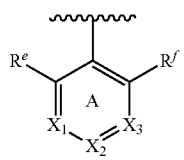

wherein ring A is optionally substituted with one or more groups $R^c$, or ring A is optionally fused with a carbocyclyl or a heterocyclyl to form a polycyclyl that is optionally substituted with one or more groups $R^g$;

$X_1$, $X_2$, and $X_3$ are each independently selected from $CR^e$ and N, provided that at least one of $X_1$, $X_2$, and $X_3$ is not N; and when A is optionally fused with a carbocyclyl or a heterocyclyl to form a polycyclyl, each of $X_1$, $X_2$, and $X_3$ can be C and can be a site of fusion;

each $R^b$ is independently selected from oxo, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —O—C(O)—O—R$^w$, —C(O)—R$^w$, —C(O)—O—R$^w$, —S(O)—R$^w$, —S(O)$_2$—R$^w$, —O—C(O)—N(R$^w$)$_2$, —N(R$^w$)—C(O)—OR$^w$, —N(R$^w$)—C(O)—N(R$^w$)$_2$, —N(R$^w$)—C(O)—R$^w$, —N(R$^w$)—S(O)—R$^w$, —N(R$^w$)—S(O)$_2$—R$^w$, —N(R$^w$)—S(O)—N(R$^w$)$_2$, and —N(R$^w$)—S(O)$_2$—N(R$^w$)$_2$, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO$_2$, —N(R$^w$)$_2$, —CN, —C(O)—N(R$^w$)$_2$, —S(O)—N(R$^w$)$_2$, —S(O)$_2$—N(R$^w$)$_2$, —O—R$^w$, —S—R$^w$, —O—C(O)—R$^w$, —C(O)—R$^w$, —C(O)—O—R$^w$, —S(O)—R$^w$, —S(O)$_2$—R$^w$, —C(O)—N(R$^w$)$_2$, —N(R$^w$)—C(O)—R$^w$, —N(R$^w$)—S(O)—R$^w$, —N(R$^w$)—S(O)$_2$—R$^w$ and $C_{1-6}$alkyl that is optionally substituted with one or more groups independently selected from oxo and halo;

each $R^c$ is independently selected from hydrogen, $C_{1-6}$alkyl, $C_{2-6}$alkenyl, $C_{2-6}$alkynyl, $C_{1-6}$haloalkyl, carbocyclyl, heterocyclyl, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—R$^v$, —N(R$^v$)—C(O)—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, $C_{1-6}$haloalkyl, carbocyclyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —S—R, —O—C(O)—R, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$, 6-membered monocyclic heterocyclyl and $C_{1-6}$alkyl that is optionally substituted with one or more groups independently selected from oxo and halo, wherein the 6-membered monocyclic heterocyclyl is optionally substituted with one or more $C_{1-6}$alkyl;

$R^e$ is hydrogen, —F, —Cl, —Br, —I, —CN, —O—R$^x$, $C_{1-6}$alkyl, $C_{2-6}$alkenyl, or $C_{2-6}$alkynyl, wherein each $C_{1-6}$alkyl, $C_{2-6}$alkenyl, or $C_{2-6}$alkynyl is optionally substituted with one or more groups independently selected from oxo, —F, —Cl, —Br, —I, —NO$_2$, —N(R$^x$)$_2$, —CN, —C(O)—N(R$^x$)$_2$, —S(O)—N(R$^x$)$_2$, —S(O)$_2$—N(R$^x$)$_2$, —O—R$^x$, —S—R$^x$, —O—C(O)—R$^x$, —O—C(O)—O—R$^x$, —C(O)—R$^x$, —C(O)—O—R$^x$, —S(O)—R$^x$, —S(O)$_2$—R$^x$, —O—C(O)—N(R$^x$)$_2$, —N(R$^x$)—C(O)—OR$^x$, —N(R$^x$)—C(O)—N(R$^x$)$_2$—N(R$^x$)—C(O)—R$^x$, —N(R$^x$)—S(O)—R$^x$, —N(R$^x$)—S(O)$_2$—R$^x$, —N(R$^x$)—S(O)—N(R$^x$)$_2$, and —N(R$^x$)—S(O)$_2$—N(R$^x$)$_2$;

$R^f$ is hydrogen, —F, —Cl, —Br, —I, —CN, —O—R$^y$, $C_{1-6}$alkyl, $C_{2-6}$alkenyl, or $C_{2-6}$alkynyl, wherein each $C_{1-6}$alkyl, $C_{2-6}$alkenyl, or $C_{2-6}$alkynyl is optionally substituted with one or more groups independently selected from oxo, —F, —Cl, —Br, —I, —NO$_2$, —N(R$^y$)$_2$, —CN, —C(O)—N(R$^y$)$_2$, —S(O)—N(R$^y$)$_2$, —S(O)$_2$—N(R$^y$)$_2$, —O—R$^y$, —S—R$^y$, —O—C(O)—R$^y$, —O—C(O)—O—R$^y$, —C(O)—R$^y$, —C(O)—O—R$^y$, —S(O)—R$^y$, —S(O)$_2$—R$^y$, —O—C(O)—N(R$^y$)$_2$, —N(R$^y$)—C(O)—OR$^y$, —N(R$^y$)—C(O)—N(R$^y$)$_2$, —N(R$^y$)—C(O)—R$^y$, —N(R$^y$)—S(O)—R$^y$, —N(R$^y$)—S(O)$_2$—R$^y$, —N(R$^y$)—S(O)—N(R$^y$)$_2$, and —N(R$^y$)—S(O)$_2$—N(R$^y$)$_2$;

each R$^g$ is independently selected from oxo, C$_{1-6}$alkyl, C$_{2-6}$alkenyl, C$_{2-6}$alkynyl, C$_{1-6}$haloalkyl, carbocyclyl, heterocyclyl, —F, —Cl, —Br, —I, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —O—C(O)—O—R$^z$, —C(O)—R$^z$, —C(O)—O—R$^z$, —S(O)—R$^z$, —S(O)$_2$—R$^z$, —O—C(O)—N(R$^z$)$_2$, —N(R$^z$)—C(O)—OR$^z$, —N(R$^z$)—C(O)—N(R$^z$)$_2$, —N(R$^z$)—C(O)—R$^z$, —N(R$^z$)—S(O)—R$^z$, —N(R$^z$)—S(O)$_2$—R$^z$, —N(R$^z$)—S(O)—N(R$^z$)$_2$, and —N(R$^z$)—S(O)$_2$—N(R$^z$)$_2$, wherein any C$_{1-6}$alkyl, C$_{2-6}$alkenyl, C$_{2-6}$alkynyl, C$_{1-6}$haloalkyl, carbocyclyl, or heterocyclyl is optionally substituted with one or more groups independently selected from oxo, halo, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —C(O)—R$^z$, —C(O)—O—R$^z$, —S(O)—R$^z$, —S(O)$_2$—R$^z$, —C(O)—N(R$^z$)$_2$, —N(R$^z$)—C(O)—R$^z$, —N(R$^z$)—S(O)—R$^z$, —N(R$^z$)—S(O)$_2$—R$^z$, C$_{1-6}$alkyl that is optionally substituted with one or more groups independently selected from oxo and halo, and heterocyclyl that is optionally substituted with one or more groups independently selected from oxo, halo, and C$_{1-6}$alkyl;

each R$^v$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, —N(R$^{va}$)$_2$, hydroxyl, cyano, C$_1$-C$_6$alkoxy, carbocyclyl, heterocyclyl, and C$_1$-C$_6$alkyl that is optionally substituted with one or more groups independently selected from oxo and halo; or two R$^v$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo, —N(R$^{va}$)$_2$ and halo;

each R$^w$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, —N(R$^{wa}$)$_2$, hydroxyl, and C$_1$-C$_6$ alkyl that is optionally substituted with one or more groups independently selected from oxo and halo; or two R$^w$ are taken together with the nitrogen to which they are attached to form a heterocyclyl that is optionally substituted with one or more groups independently selected from oxo, halo and C$_{1-3}$alkyl that is optionally substituted with one or more groups independently selected from oxo and halo;

each R$^x$ is independently selected from hydrogen, C$_{1-6}$alkyl, C$_{2-6}$alkenyl, and C$_{2-6}$alkynyl, wherein each C$_{1-6}$alkyl, C$_{2-6}$alkenyl, or C$_{2-6}$alkynyl is optionally substituted with one or more groups independently selected from oxo, halo, amino, hydroxyl, and C$_1$-C$_6$ alkyl;

each R$^y$ is independently selected from hydrogen, C$_{1-6}$alkyl, C$_{2-6}$alkenyl, and C$_{2-6}$alkynyl, wherein each C$_{1-6}$alkyl, C$_{2-6}$alkenyl, or C$_{2-6}$alkynyl is optionally substituted with one or more groups independently selected from oxo, halo, amino, hydroxyl, and C$_1$-C$_6$ alkyl;

each R$^z$ is independently selected from hydrogen, C$_{1-6}$alkyl, C$_{2-6}$alkenyl, C$_{2-6}$alkynyl, carbocyclyl, and heterocyclyl, wherein each C$_{1-6}$alkyl, C$_{2-6}$alkenyl, C$_{2-6}$alkynyl, carbocyclyl, or heterocyclyl is optionally substituted with one or more groups independently selected from oxo, halo, cyano, —N(R$^{za}$)$_2$, C$_1$-C$_6$alkoxy, carbocyclyl, —N(R$^{za}$)$_2$, —C(O)—N(R$^{za}$)$_2$, —O—C(O)—R$^{za}$, —C(O)—O—R$^{za}$, —N(R$^{za}$)—C(O)—R$^{za}$, and C$_1$-C$_6$ alkyl that is optionally substituted with one or more groups independently selected from oxo and halo; or two R$^z$ are taken together with the nitrogen to which they are attached to form a heterocyclyl that is optionally substituted with one or more groups independently selected from oxo, halo, —N(R$^{za}$)$_2$, —C(O)—N(R$^{za}$)$_2$, —O—C(O)—R$^{za}$, —C(O)—O—R$^{za}$, —N(R$^{za}$)—C(O)—R$^{za}$, and C$_{1-3}$alkyl that is optionally substituted with one or more groups independently selected from oxo and halo;

each R$^{va}$ is independently hydrogen or C$_{1-6}$alkyl, or two R$^{va}$ are taken together with a nitrogen to which they are attached to form a heterocyclyl;

each R$^{wa}$ is independently hydrogen or C$_{1-6}$alkyl, or two R$^{wa}$ are taken together with a nitrogen to which they are attached to form a heterocyclyl; and each R$^{za}$ is independently hydrogen or C$_{1-6}$alkyl, or two R$^{za}$ are taken together with a nitrogen to which they are attached to form a heterocyclyl;

provided that when R$^1$ is methyl; and R$^2$ is ethoxycarbonyl; then A is not 2-fluoro-5-(ethylsulfonyl)phenyl;

and provided that when R$^1$ is methyl; and R$^2$ is hydrogen; then A is not 2-(2,2-dimethylprop-1-yloxy)-5-aminophenyl;

and provided that when R$^1$ is methyl; and R$^2$ is hydrogen; then A is not 2-(2,2-dimethylprop-1-yloxy)-5-nitrophenyl;

and provided that when R$^1$ is methyl; and R$^2$ is hydrogen; then A is not 3-(ethylsulfonyl)-6-fluorophenyl;

and provided that when R$^1$ is methyl; and R$^2$ is hydrogen; then A is not 2-ethoxy-5-(methylsulfonyl) phenyl;

and provided that when R$^1$ is methyl; and R$^2$ is hydrogen; then A is not 4-bromo-2-methoxyphenyl;

and provided that when R$^1$ is methyl; and R$^2$ is hydrogen; then A is not 2-(2-tert-butoxy-1-methylethoxy)-5-methylsulfonylphenyl;

and provided that when R$^1$ is methyl; and R$^2$ is hydrogen; then A is not 2-iso-butoxy-5-methylsulfonylphenyl;

and provided that when R$^1$ is methyl; and R$^2$ is hydrogen; then A is not 2-(2-methylpropoxy)-5-ethylsulfonylaminophenyl.

2. The compound or salt of claim 1 wherein Q is a furyl, thienyl, pyrrolyl, imidazolyl, thiazolyl, oxazolyl, isoxazolyl, thiazolyl, isothiazolyl, or triazolyl that is optionally substituted with one or more groups R$^c$.

3. The compound or salt of claim 1 wherein Q is:

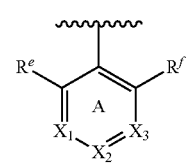

wherein ring A is optionally substituted with one or more groups R$^c$, or ring A is optionally fused with a carbocyclyl or a heterocyclyl to form a polycyclyl that is optionally substituted with one or more groups R$^g$.

4. The compound or salt of claim 1 wherein Q is:

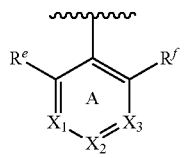

wherein ring A is optionally substituted with one or more groups R$^c$.

5. The compound or salt of claim 1 wherein Q is:

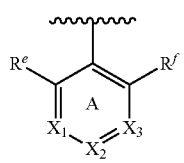

wherein ring A is fused with a carbocyclyl or a heterocyclyl to form a polycyclyl that is optionally substituted with one or more groups R$^g$.

6. The compound or salt of claim 1 wherein each R$^c$ is independently selected from hydrogen, C$_{1-6}$alkyl, heterocyclyl, —CN, —C(O)—N(R$^v$)$_2$, —N(R$^v$)—C(O)—OR$^v$ and —N(R$^v$)—C(O)—R$^v$, wherein any C$_{1-6}$alkyl, or heterocyclyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —N(R$^v$)—C(O)—R$^v$, —N(R$^v$)—S(O)—R$^v$, —N(R$^v$)—S(O)$_2$—R$^v$, 6-membered monocyclic heterocyclyl and C$_{1-6}$alkyl that is optionally substituted with one or more groups independently selected from oxo and halo, wherein the 6-membered monocyclic heterocyclyl is optionally substituted with C$_{1-6}$alkyl.

7. The compound or salt of claim 1 wherein each R$^c$ is independently selected from hydrogen, C$_{1-6}$alkyl, heterocyclyl, —CN, —C(O)—N(R$^v$)$_2$, —N(R$^v$)—C(O)—OR$^v$ and —N(R$^v$)—C(O)—R$^v$, wherein any C$_{1-6}$alkyl, or heterocyclyl is optionally substituted with one or more groups independently selected from —O—R$^v$, 6-membered monocyclic heterocyclyl and C$_{1-6}$alkyl that is optionally substituted with one or more groups independently selected from oxo and halo, wherein the 6-membered monocyclic heterocyclyl is optionally substituted with C$_{1-6}$alkyl.

8. The compound or salt of claim 1 wherein ring A is fused with a carbocyclyl to form a polycyclyl that is optionally substituted with one or more groups R$^g$.

9. The compound or salt of claim 1 wherein ring A is fused with a heterocyclyl to form a polycyclyl that is optionally substituted with one or more groups R$^g$.

10. The compound or salt of claim 1 wherein each R$^g$ is independently selected from oxo, carbocyclyl, heterocyclyl and —C(O)—O—W wherein any C$_{1-6}$alkyl, carbocyclyl or heterocyclyl is optionally substituted with one or more groups independently selected from oxo, halo, —NO$_2$, —N(R$^z$)$_2$, —CN, —C(O)—N(R$^z$)$_2$, —S(O)—N(R$^z$)$_2$, —S(O)$_2$—N(R$^z$)$_2$, —O—R$^z$, —S—R$^z$, —O—C(O)—R$^z$, —C(O)—R$^z$, —C(O)—O—R$^z$, —S(O)—R$^z$, —S(O)$_2$—R$^z$, —C(O)—N(R$^z$)$_2$, —N(R$^z$)—C(O)—R$^z$, —N(R$^z$)—S(O)—R$^z$, —N(R$^z$)—S(O)$_2$—R$^z$, C$_{1-6}$alkyl that is optionally substituted with one or more groups independently selected from oxo and halo, and heterocyclyl that is optionally substituted with one or more groups independently selected from oxo, halo, and C$_{1-6}$alkyl.

11. The compound or salt of claim wherein each R$^g$ is independently selected from oxo, carbocyclyl, heterocyclyl and —C(O)—O—R$^z$ wherein any C$_{1-6}$alkyl, carbocyclyl, or heterocyclyl is optionally substituted with one or more —O—R$^z$ groups.

12. The compound or salt of claim 1 wherein Q is selected from:
phenyl, 2-oxoindolin-5-yl, 1-tert-butoxycarbonyl-3,4-dihydro-2H-quinolin-6-yl, 2,3,3a,5-tetrahydropyrrolo[1,2-a]quinoxaline-1,4-dione-8-yl, 3-methyl-3,4-dihydro-1H-quinoxalin-2-one-6-yl, 1,3,4,5-tetrahydro-4-methyl-1,5-benzodiazepin-2-one-7-yl, 5,7,7a,8,9,10-hexahydropyrrolo[2,1-d][1,5]benzodiazepin-6-one-2-yl, 4-(2-thienyl)-1,3,4,5-tetrahydro-1,5-benzodiazepin-2-one-7-yl, 3-aminocarbonylphenyl, 3-cyanophenyl, 4-hydroxymethylphenyl, 4-(3-fluoroazetidin-1-ylcarbonyl)phenyl, 4-(1-pyrrolidinylcarbonyl)phenyl, 4-(4-methylpiperidine-1-ylcarbonyl)phenyl, 4-(4-acetylpiperazine-1-ylcarbonyl)phenyl, 4-(4-(aminocarbonyl)piperidin-1-ylcarbonyl)phenyl, 4-(N-(pyrid-3-yl)aminocarbonyl)phenyl, 4-(2-phenylpropanooyl)phenyl, 4-(N-methyl-N-(cyanomethyl)aminocarbonyl)phenyl, 4-(N-(2-methoxyethyl)aminocarbonyl)phenyl, 1-tert-butoxycarbonyl-3,4-dihydro-2H-quinolin-7-yl, 4-(tert-butoxycarbonylamino)phenyl, 1,3,4,5-tetrahydro-1,5-benzodiazepin-2-one-7-yl, 3-(N,N-dimethylaminocarbonyl)phenyl, 4-(1-hydroxy-1-methylethyl)phenyl, 4-(1methylpiperidin-4-yl)phenyl, 4-(1methylpiperidin-4-ylmethyl)phenyl, 4-(N-(2-methoxyethylcarbonyl)amino)phenyl, 2-methyl-4H-1,4-benzoxazin-3-one-7-yl, 4-(N,N-dimethylaminocarbonyl)phenyl, 4-(4-methyl-3-oxo-piperazine-1-ylcarbonyl)phenyl, 4-(3,3-difluoroazetidin-1-ylcarbonyl)phenyl, 4-(N-phenylaminocarbonyl)phenyl, 4-(2-methyl-3,4-dihydro-1H-isoquinolin-6-yl, 3-(N-methylaminocarbonyl)phenyl, 4-(morpholinocarbonyl)phenyl, 3-(N-benzylaminocarbonyl)phenyl, 3-(1-methylpiperidin-4-yl)phenyl, 3-(1-methylpiperidin-4-ylmethyl)phenyl, and 3-(2-hydroxyethyl)-3-phenylindan-5-yl.

13. The compound or salt of claim 1 that is selected from the group consisting of:
6-methyl-4-phenyl-1H-pyrrolo[2,3-c]pyridin-7(6H)-one;
6-methyl-4-(2-oxoindolin-5-yl)-1H-pyrrolo[2,3-c]pyridin-7-one;
N-(2-methoxyethyl)-4-(6-methyl-7-oxo-1H-pyrrolo[2,3-c]pyridin-4-yl)benzamide;
tert-butyl 6-(6-methyl-7-oxo-1H-pyrrolo[2,3-c]pyridin-4-yl)-3,4-dihydro-2H-quinoline-1-carboxylate;
tert-butyl 7-(6-methyl-7-oxo-1H-pyrrolo[2,3-c]pyridin-4-yl)-3,4-dihydro-2H-quinoline-1-carboxylate;
tert-butyl N-[4-(6-methyl-7-oxo-1H-pyrrolo[2,3-c]pyridin-4-yl)phenyl]carbamate;
3-methoxy-N-[4-(6-methyl-7-oxo-1H-pyrrolo[2,3-c]pyridin-4-yl)phenyl]propanamide;
4-(3-(2-hydroxyethyl)-3-phenyl-2,3-dihydro-1H-inden-5-yl)-6-methyl-1H-pyrrolo[2,3-c]pyridin-7(6H)-one;
8-(6-methyl-7-oxo-6,7-dihydro-1H-pyrrolo[2,3-c]pyridin-4-yl)-3,3a-dihydropyrrolo[1,2-a]quinoxaline-1,4(2H,5H)-dione;

3-methyl-6-(6-methyl-7-oxo-1H-pyrrolo[2,3-c]pyridin-4-yl)-3,4-dihydro-1H-quinoxalin-2-one;
3-methyl-7-(6-methyl-7-oxo-1H-pyrrolo[2,3-c]pyridin-4-yl)-1,3,4,5-tetrahydro-1,5-benzodiazepin-2-one;
7-(6-methyl-7-oxo-1H-pyrrolo[2,3-c]pyridin-4-yl)-1,3,4,5-tetrahydro-1,5-benzodiazepin-2-one;
4-methyl-7-(6-methyl-7-oxo-1H-pyrrolo[2,3-c]pyridin-4-yl)-1,3,4,5-tetrahydro-1,5-benzodiazepin-2-one;
3-isopropyl-6-(6-methyl-7-oxo-1H-pyrrolo[2,3-c]pyridin-4-yl)-1H-quinoxalin-2-one;
2-(6-methyl-7-oxo-1H-pyrrolo[2,3-c]pyridin-4-yl)-5,7,7a,8,9,10-hexahydropyrrolo[2,1-d][1,5]benzodiazepin-6-one;
2-methyl-7-(6-methyl-7-oxo-1H-pyrrolo[2,3-c]pyridin-4-yl)-4H-1,4-benzoxazin-3-one;
7-(6-methyl-7-oxo-1H-pyrrolo[2,3-c]pyridin-4-yl)-4-(2-thienyl)-1,3,4, 5-tetrahydro-1,5-benzodiazepin-2-one;
N,N-dimethyl-4-(6-methyl-7-oxo-1H-pyrrolo[2,3-c]pyridin-4-yl)benzamide;
3-(6-ethyl-7-oxo-1H-pyrrolo[2,3-c]pyridin-4-yl)-N,N-dimethyl-benzamide;
3-(6-methyl-7-oxo-1H-pyrrolo[2,3-c]pyridin-4-yl)benzamide;
N,N-dimethyl-3-(6-methyl-7-oxo-1H-pyrrolo[2,3-c]pyridin-4-yl)benzamide;
3-(6-methyl-7-oxo-1H-pyrrolo[2,3-c]pyridin-4-yl)benzonitrile;
N-methyl-3-(6-methyl-7-oxo-1H-pyrrolo[2,3-c]pyridin-4-yl)benzamide;
4-[4-(hydroxymethyl)phenyl]-6-methyl-1H-pyrrolo[2,3-c]pyridin-7-one;
6-methyl-4-(4-(4-methyl-3-oxopiperazine-1-carbonyl)phenyl)-1H-pyrrolo[2,3-c]pyridin-7(6H)-one;
4-[4-(3-fluoroazetidine-1-carbonyl)phenyl]-6-methyl-1H-pyrrolo[2,3-c]pyridin-7-one;
4-[4-(3,3-difluoroazetidine-1-carbonyl)phenyl]-6-methyl-1H-pyrrolo[2,3-c]pyridin-7-one;
6-methyl-4-[4-(pyrrolidine-1-carbonyl)phenyl]-1H-pyrrolo[2,3-c]pyridin-7-one;
6-methyl-4-[4-(morpholine-4-carbonyl)phenyl]-1H-pyrrolo[2,3-c]pyridin-7-one;
6-methyl-4-[4-(4-methylpiperidine-1-carbonyl)phenyl]-1H-pyrrolo[2,3-c]pyridin-7-one;
4-[4-(4-acetylpiperazine-1-carbonyl)phenyl]-6-methyl-1H-pyrrolo[2,3-c]pyridin-7-one,
1-[4-(6-methyl-7-oxo-1H-pyrrolo[2,3-c]pyridin-4-yl)benzoyl]piperidine-4-carboxamide;
4-(6-methyl-7-oxo-1H-pyrrolo[2,3-c]pyridin-4-yl)-N-(3-pyridyl)benzamide;
4-(6-methyl-7-oxo-1H-pyrrolo[2,3-c]pyridin-4-yl)-N-phenyl-benzamide;
N-methyl-4-(6-methyl-7-oxo-1H-pyrrolo[2,3-c]pyridin-4-yl)-N-phenyl-benzamide;
N-benzyl-4-(6-methyl-7-oxo-1H-pyrrolo[2,3-c]pyridin-4-yl)benzamide;
N-(cyanomethyl)-N-methyl-4-(6-methyl-7-oxo-1H-pyrrolo[2,3-c]pyridin-4-yl)benzamide;
4-[4-(1-hydroxy-1-methyl-ethyl)phenyl]-6-methyl-1H-pyrrolo[2,3-c]pyridin-7-one;
6-methyl-4-[4-(1-methyl-4-piperidyl)phenyl]-1H-pyrrolo[2,3-c]pyridin-7-one;
6-methyl-4-[3-(1-methyl-4-piperidyl)phenyl]-1H-pyrrolo[2,3-c]pyridin-7-one;
6-methyl-4-(2-methyl-3,4-dihydro-1H-isoquinolin-6-yl)-1H-pyrrolo[2,3-c]pyridin-7-one;
6-methyl-4-[4-[(1-methyl-4-piperidyl)methyl]phenyl]-1H-pyrrolo[2,3-c]pyridin-7-one;
6-methyl-4-[3-[(1-methyl-4-piperidyl)methyl]phenyl]-1H-pyrrolo[2,3-c]pyridin-7-one; and
3-(2,6-dimethyl-7-oxo-1H-pyrrolo[2,3-c]pyridin-4-yl)-N,N-dimethyl-benzamide
and salts thereof.

14. A composition comprising a compound of formula (I) as described in claim 1, or a pharmaceutically acceptable salt thereof, and a pharmaceutically acceptable adjuvant, carrier, or vehicle.

* * * * *

UNITED STATES PATENT AND TRADEMARK OFFICE
CERTIFICATE OF CORRECTION

PATENT NO. : 10,150,767 B2
APPLICATION NO. : 15/592017
DATED : December 11, 2018
INVENTOR(S) : Brian K. Albrecht et al.

Page 1 of 1

It is certified that error appears in the above-identified patent and that said Letters Patent is hereby corrected as shown below:

In the Claims

Column 118, Line 41, Claim 1, please delete "-S(O)$_2$-N(R$^V$)$_2$, -S-R," and insert
-- -S(O)$_2$-N(R$^V$)$_2$, -O-R$^V$, -S-R$^V$, --;

Column 118, Line 41, Claim 1, please delete "-O-C(O)-R," and insert -- -O-C(O)-R$^V$,--;

Column 120, Line 14, Claim 1, please delete "(R$^{za}$)$_2$, -O-C(O)-R$^{za}$," and insert
-- (R$^{za}$)$_2$, -O-R$^{za}$, -O-C(O)-R$^{za}$, --;

Column 120, Line 20, Claim 1, please delete "-C(O)-N(R$^{za}$)$_2$, -O-C(O)-R$^{za}$," and insert
-- -C(O)-N(R$^{za}$)$_2$, -O-R$^{za}$, -O-C(O)-R$^{za}$, --;

Column 121, Line 37, Claim 6, please delete "(R$^v$)$_2$, -S-R$^v$," and insert -- (R$^v$)$_2$, -O-R$^v$, -S-R$^v$, --;

Column 121, Line 62, Claim 10, please delete "oxo, carbocyclyl," and insert
-- oxo, C$_1$-C$_6$alkyl, carbocyclyl, --;

Column 121, Line 63, Claim 10, please delete "-C(O)-O-W" and insert -- -C(O)-O-R$^z$ --;

Column 122, Line 9, Claim 10, please delete "oxo, carbocyclyl," and insert -- oxo, C$_1$-C$_6$alkyl, carbocyclyl, -- therefor.

Signed and Sealed this
Fifth Day of March, 2019

Andrei Iancu
*Director of the United States Patent and Trademark Office*